United States Patent
Ohkawa et al.

(10) Patent No.: US 7,008,950 B1
(45) Date of Patent: Mar. 7, 2006

(54) BENZOFURANS AS SUPPRESSORS OF NEURODEGENERATION

(75) Inventors: Shigenori Ohkawa, Osaka (JP); Masaki Setoh, Osaka (JP); Mitsuru Kakihana, Hyogo (JP); Masahiro Okura, Osaka (JP)

(73) Assignee: Takeda Chemical Industries, Ltd., Osaka (JP)

(*) Notice: Subject to any disclaimer, the term of this patent is extended or adjusted under 35 U.S.C. 154(b) by 0 days.

(21) Appl. No.: 09/445,193

(22) PCT Filed: Jun. 4, 1998

(86) PCT No.: PCT/JP98/02482

§ 371 (c)(1),
(2), (4) Date: Dec. 2, 1999

(87) PCT Pub. No.: WO98/55454

PCT Pub. Date: Dec. 10, 1998

(30) Foreign Application Priority Data

Jun. 5, 1997 (JP) .............................. 9/148325

(51) Int. Cl.
*A61K 31/44* (2006.01)
*A61K 31/34* (2006.01)
*C07D 421/00* (2006.01)
*C07D 307/78* (2006.01)

(52) U.S. Cl. .................. 514/278; 514/469; 514/345; 514/348; 514/349; 514/350; 514/351; 514/352; 514/357; 514/356; 514/354; 546/196; 549/469

(58) Field of Classification Search ............... 549/467, 549/469; 546/196; 514/278, 469, 345, 348, 514/349, 350, 351, 352, 357, 356, 354, 409
See application file for complete search history.

(56) References Cited

U.S. PATENT DOCUMENTS

| 4,426,385 A | 1/1984 | Cain |
| 4,659,360 A | 4/1987 | Baum et al. |
| 5,593,989 A | 1/1997 | Peglion et al. |
| 5,668,142 A | 9/1997 | Peglion et al. |
| 5,681,842 A | 10/1997 | Dellaria et al. |
| 5,747,508 A | 5/1998 | Richter et al. |
| 2004/0034049 A1 * | 2/2004 | Okawa et al. |

FOREIGN PATENT DOCUMENTS

| DE | 19602095 A1 | 7/1997 |
| EP | 0054924 A2 | 6/1982 |
| EP | 0165810 A2 | 12/1985 |
| EP | 0224816 A1 | 6/1987 |
| EP | 0273647 A1 | 7/1988 |
| EP | 0277842 A1 | 8/1988 |
| EP | 0281261 A2 | 9/1988 |
| EP | 0345592 A1 | 12/1989 |
| EP | 0345593 A1 | 12/1989 |
| EP | 0365925 A1 | 5/1990 |
| EP | 0383281 A1 | 8/1990 |
| EP | 0394043 A1 | 10/1990 |
| EP | 0445073 A1 | 9/1991 |
| EP | 0483772 A1 | 5/1992 |
| EP | 0526951 A1 | 2/1993 |
| EP | 0686637 A1 | 12/1995 |
| EP | 0722726 A1 | 7/1996 |
| EP | 0729956 A1 | 9/1996 |
| EP | 0733631 A1 | 9/1996 |
| EP | 0778274 A1 | 6/1997 |
| JP | 01199957 | 8/1989 |
| JP | 2-233679 | 9/1990 |
| JP | 3-151311 | 6/1991 |
| JP | 3-161405 | 7/1991 |
| JP | 03261778 | 11/1991 |
| JP | 4-95070 | 3/1992 |
| JP | 4-193803 | 7/1992 |
| JP | 6-239853 | 8/1994 |
| JP | 6312976 | 11/1994 |
| JP | 7145147 | 6/1995 |

(Continued)

OTHER PUBLICATIONS

CA 109:149335, "Preparation of 5–hydroxycoumaran derivatives as cardiovascular and antiallergy agents", Terao et. al., EP 273647.*

A. Ratnakar et al., "Synthesis of a New Type of 5–Heteroaryl–3– . . . " *Asian J. of Chemistry* vol. 4, No. 2, (1992), pp. 197–200.

Z.M. Wang et al., "The Revised Structure of Gnetifolin A" *Chinese Chemical Letters* vol. 6, No. 8, pp. 683–686.

K. Clarke et al., "Substitution Reactions of Benzo[b] thiophen Derivatives. Part VII . . . " *J.C.S. Perkin I*, (1973), pp. 1196–1200.

D. Kemp and D. Buckler, "New Templates for Prior Thiol Capture . . . " *Tetrahedron Letters*, vol. 32, No. 26, pp. 3009–3012, (1991).

(Continued)

*Primary Examiner*—Cecilia J. Tsang
*Assistant Examiner*—Binta Robinson
(74) *Attorney, Agent, or Firm*—Elaine M. Ramesh; Mark Chao

(57) ABSTRACT

A compound of the formula:

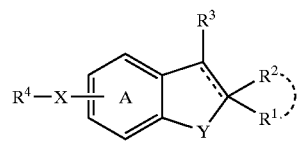

wherein $R^1$ and $R^2$ each is H or a hydrocarbon group which may be substituted, or $R^1$ and $R^2$ form a 3- to 8-membered carbo or heterocyclic ring which may be substituted; $R^3$ is H, a lower alkyl which may be substituted or an aromatic group which may be substituted; $R^4$ is (1) an aromatic group which may be substituted, (2) an aliphatic hydrocarbon group substituted by an aromatic group which may be substituted, which hydrocarbon group may be further substituted or (3) an acyl; X and Y each is oxygen or sulfur which may be oxidized; and ring A is a benzene ring which may be further substituted, or a salt thereof, is useful for an agent for suppressing neurodegeneration.

6 Claims, No Drawings

FOREIGN PATENT DOCUMENTS

| JP | 7-179856 | 7/1995 |
|----|----------|--------|
| JP | 7-247263 | 9/1995 |
| WO | WO 84/02131 | 6/1984 |
| WO | WO 87/00840 | 2/1987 |
| WO | WO 91/05474 | 5/1991 |
| WO | WO 94/14434 | 7/1994 |
| WO | WO 95/09159 | 4/1995 |
| WO | WO 95/17095 | 6/1995 |
| WO | WO 95/29907 | 11/1995 |
| WO | WO 96/04251 | 2/1996 |
| WO | WO 96/10999 | 4/1996 |
| WO | WO 96/11192 | 4/1996 |
| WO | WO 96/20925 | 7/1996 |
| WO | WO 97/25033 | 7/1997 |
| WO | WO 97/34869 | 9/1997 |
| WO | WO 98/05292 | 2/1998 |

OTHER PUBLICATIONS

M. Iwasaki et al., "Palladium–Catalyzed Cyclocarbonylation of 3–(Heteroary)allyl Acetates" J. Org. Chem. (1991), vol. 56, pp. 1922–1927.

M. Shipchandler et al., "Coumarins XI: A Total Synthesis of . . . " J. Pharmaceutical Science, vol. 59, No. 1, (Jan. 1970) pp. 67–71.

E. Campaigne and R. Rogers, "Benzo[b]thiophene Derivatives. XIX. The Sulfur Isosteres of . . . " J. Heterocycl. Chem., vol. 10, No. 3, (1973) pp. 297–305.

XP002074285 Chemical Abstracts, vol. 110, No. 19, (May 8, 1989) pp. 762, abstract No. 173099g.

XP002074286 Chemical Abstracts, vol. 126, No. 17, (Apr. 28, 1997) pp. 570, abstract No. 225226y.

M. David et al., "Une nouvelle voie d'accés courte . . ." Bull. Soc. Chim. Fr., vol. 130, No. 4, 1993, pp. 527–534, with its English abstract.

JS Kaltenbronn et al., "Benzofuran derivatives a ETA–selective, non–peptide endothelin antagonists" Eur. J. Med. Chem. (1997), vol. 32, pp. 425–431.

M. David et al., "Evaluation of Antiviral Activity of Chromane Diols and their Synthetic Analogues" Pharmaceutical Sciences (1997), vol. 3, pp. 305–309.

B. Snider et al, "Synthesis of 2,3–Dihydrobenzofurans by $Mn(Oac)_3$–Based . . . " J. Org. Chem. (1997), vol. 62, pp. 6978–6984.

M. Miyake et al., "Synthesis and Biological Activity of Arthrographol and Related Compounds" Heterocyoles, vol. 43, No. 3, 1996, pp. 665–674.

H. Matsutani et al., "Synthesis of Ferroelectric Liquid Crystals Having Chiral . . . " Mol. Cryst. Ltq. Cryst. 1995, vol. 263, pp. 131–138.

M. Ponpipom et al., "Structure–Activity Relationships of Kadsurenone Analogues" J. Med. Chem. 1987, vol. 30, pp. 136–142.

R. Cline et al., "Gas Chromatographic and Spectral Properties of . . . " J. Chromatographic Science, vol. 28, (Apr. 1990), pp. 167–172.

* cited by examiner

BENZOFURANS AS SUPPRESSORS OF NEURODEGENERATION

TECHNICAL FIELD

The present invention relates to heterocyclic compounds, their production and use, which compounds suppress cell toxicities caused by β-amyloid protein, protect nerve cells, and are useful for preventing and/or treating neurodegenerative diseases by protecting nerve cells from other inducers of cell death.

BACKGROUND ART

Neurodegenerative diseases are progressive disorders that cause fatal damage to, or nerve cell death. As principal neurodegenerative diseases, known are Alzheimer's disease, Parkinson's disease, amyotrophic lateral sclerosis (ALS), Huntington's chorea, peripheral nervous system disorders such as typically diabetic neuropathy, etc. Most of those are related to aging, and, in fact, cases that present the symptoms of those diseases increase with aging. However, middle-aged and even young-aged cases may often present the symptoms of those diseases.

As a result of studies relating to the structure and function of brains, the roles of neurotransmitters and neurotrophins are being gradually clarified, but for the most part the causes of neurodegenerative diseases are still unknown. Only for Parkinson's disease, has the relation between it and a specific neurotransmitter, dopamine has been clarified. L-dopa, which is a precursor of dopamine, is used as a medicine for Parkinson's disease. L-dopa relieves the neuropathic manifestation of Parkinson's disease, and maintains function. However, L-dopa does not suppress the progress of neurodegeneration in cases of Parkinson's disease, and it gradually loses its potency with the progress of the manifestation of the disease, or that is, with the degeneration and death of dopamine-based nerve cells. Alzheimer's disease results in the degeneration and death of many types of nerve cells such as acetylcholine-based nerve cells and monoamine-based nerve cells. For this disease, some cholinesterase inhibitors are commercially available and some others are in the development stage. However, those are still within the range of symptomatic treatment for temporarily relieving the neuropathic manifestation of Alzheimer's disease, like L-dopa for Parkinson's disease.

As has been mentioned above, no medicines have been reported for protecting nerve cells from the toxicity of factors causing cell death thereby to suppress the progress of neurodegenerative diseases including Alzheimer's disease and Parkinson's disease.

It is said that the cell death in neurodegenerative diseases is caused by the toxicity of factors that are intrinsic to the respective diseases. For Alzheimer's disease, for example, it is believed that the intrinsic β-amyloid in the disease is a factor which causes cell death. β-amyloid is a protein seen in the brains of cases of Alzheimer's disease, constitutes senile lentigines that are characteristic of the disease in neuropathology, and is composed of from 40 to 43 amino acids. It has been clarified that, when β-amyloid is added to the primary culture of hippocampus nerve cells, this kills the cells (see Science, Vol. 245, pp. 417–420, 1989); and it has been reported that the coagulation of β-amyloid is indispensable for the expression of its toxicity (see Neurobiology of Aging, Vol. 13, pp. 587–590, 1992; and Journal of Molecular Biology, Vol. 218, pp. 149–163, 1991). For the toxicity expression mechanism of β-amyloid, the following (1) to (4) may be taken into consideration: (1) β-amyloid forms ion channels, through which calcium ions run into nerve cells. (2) β-amyloid promotes the generation of free radicals.

(3) β-amyloid activates tau-protein kinase I (TPK-I) whereby phosphorylation of tau is promoted. (4) β-amyloid activates microglia, which thereby secretes neurotoxin. However, no one has as yet confirmed this.

Recently, it has been clarified that neurotrophins such as IGF-1 (insulin-like growth factor) and NGF (nerve growth factor) inhibit the apoptosis of nerve cells by β-amyloid or the like, and that, for its mechanism, the apoptosis inhibition is related to the inhibition of TPK-I/GSK-3β (glycogen synthase kinase 3) through activation of PI-3 kinase (see J. Neurosci., Vol. 11, pp. 2552–2563, 1991; Science, Vol. 267, pp. 2003–2006, 1995; and J. Biol. Chem., Vol. 272, pp. 154–161, 1997). When PI-3 kinase is inhibited by β-amyloid and TPK-I/GSK-3β is activated, then pyruvate dehydrogenase (PDH) is inhibited, while having an influence on the synthesis of acetylcholine, to thereby lower the acetylcholine content. This is supported by the decrease in the acetylcholine content of the brains of cases of Alzheimer's disease. On the contrary, when PI-3 kinase is activated, then it is expected that not only the nerve cell death is prevented but also the intracerebral acetylcholine content is increased to improve the nervous system condition. In addition, it is also expected that the inhibition of TPK-I/GSK-3β results in the increase in the intracerebral glucose utilization which is lowered in cases of Alzheimer's disease (see J. Biol. Chem., Vol. 269, pp. 3568–3573, 1994; and Endocrinology, Vol. 125, pp. 314–320, 1989). Accordingly, low-molecular compounds having good permeability to the brain and having neurotrophic action may inhibit nerve cell death in cases of neurodegenerative diseases such as Alzheimer's disease, while improving the nervous system condition in those cases.

Known are the following dihydrobenzofuran compounds which are effective for neurodegenerative diseases (e.g., Parkinson's disease, Alzheimer's disease, etc.).

1) A compound of the formula:

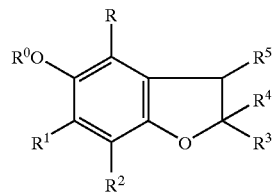

wherein R is a lower alkyl, $R^0$ is hydrogen or an acyl; $R^1$ and $R^2$ are the same or different and are a lower alkyl which may be substituted, or $R^1$ and $R^2$, taken together, are a butadienylene which may be substituted; $R^3$ and $R^4$ each is hydrogen or an alkyl which may be substituted, or $R^3$ and $R^4$, taken together, are a polymethylene; $R^5$ is a lower alkyl, an aromatic group or heterocyclic group which may be substituted (EP-A-273647, JP-A-1-272578).

2) A compound of the formula:

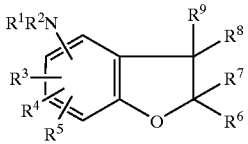

wherein $R^1$ and $R^2$ are the same or different and are a hydrogen atom, an acyl, an alkoxycarbonyl, an optionally substituted aliphatic group or an optionally substituted aromatic group; $R^3$, $R^4$ and $R^5$ are the same or different and are an optionally acylated hydroxy, an optionally substituted amino, an optionally substituted alkoxy or an optionally substituted aliphatic group, or two of $R^3$, $R^4$ and $R^5$ may be linked together to form an optionally substituted carbocyclic group: $R^6$ and $R^7$ are the same or different and are an optionally substituted aliphatic group, provided that at least one of $R^6$ and $R^7$ has methylene at α-position; and $R^8$ and $R^9$ are the same or different and are a hydrogen atom, an optionally substituted aliphatic group or an optionally substituted aromatic group, or a salt thereof (EP-A-483772, JP-A-5-140142).

Also known are the following benzofuran compounds and dihydrobenzofuran compounds.

3) A compound of the formula:

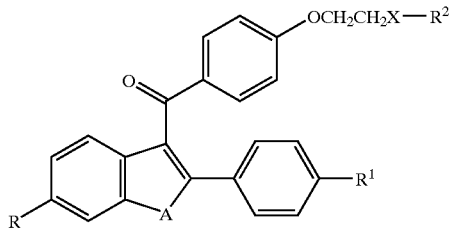

wherein A is —O—, —S(O)m—, —N($R^{11}$)—, —CH$_2$CH$_2$-, or —CH=CH—; m is 0, 1, or 2; X is a bond or $C_{1-4}$, alkylidenyl: $R^2$ is a group of the formula: —N$R^4R^5$ wherein $R^4$ and $R^5$ are independently $C_{1-6}$ alkyl, etc.); R is hydroxy, halo, $C_{3-8}$ cycloalkyl, $C_{2-7}$ alkanoyloxy, $C_{1-6}$ alkoxy, phenyl, etc.; $R^1$ is hydroxy, halo, hydrogen, $C_{3-8}$ cycloalkyl, $C_{2-7}$, alkanoyloxy, $C_{1-6}$ alkoxy, phenyl, etc., or a pharmaceutically acceptable salt, which is useful for the prevention and treatment of physiological disorder associated with an β-amyloid such as Alzheimer's disease and Down's syndrome (WO 95/17095).

4) A compound of the formula:

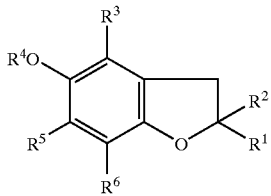

wherein $R^1$ is hydrogen or a lower alkyl; $R^2$ is a methyl substituted by carboxy, alkoxycarbonyl, cyano, halogen, aryl or heterocyclic group, or $C_{2-15}$ chain-like hydrocarbon residue having no lower alkyl at α-position which may be substituted by carboxy, alkoxycarbonyl, cyano, halogen, aryl or a heterocyclic group; $R^3$ is a lower alkyl: $R^4$ is hydrogen of an acyl; $R^5$ and $R^6$ each is a lower alkyl of a lower alkoxy, or $R^5$ and $R^6$, taken together, are butadienylene, or a salt thereof, which has 5- or 12-lipoxygenase inhibiting actions (EP-A-345593, JP-A-2-76869).

5) A compound of the formula:

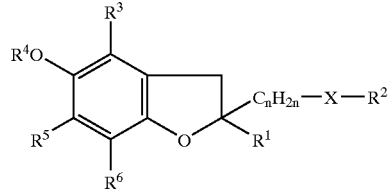

wherein $R^1$ is hydrogen or a lower alkyl; n is 1 to 6; X is sulfur which may be oxidized, oxygen or imino which may be substituted; $R^2$ is methyl or an organic residue bonded through methylene, methylene or quaternary carbon; $R^3$ is a lower alkyl; $R^4$ is hydrogen or an acyl; $R^5$ and $R^6$ each is a lower alkoxy or a lower alkyl, or $R^5$ and $R^6$, taken together, are butadienylene, or a salt thereof, which has a 5-lipoxygenase inhibiting action (EP-A-345592, JP-A-2-76870).

6) A compound of the formula:

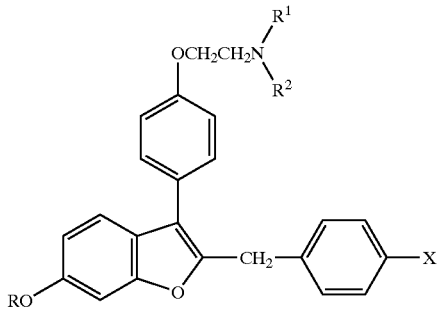

wherein R is hydrogen or methyl; $R^1$ and $R^2$ each are methyl or ethyl, or $R^1$ and $R^2$ taken together are a saturated heterocyclic group; and X is bromo, chloro, fluoro or hydrogen, or a pharmaceutically acceptable salt thereof, which is useful for inhibiting bone loss (EP-A-722726).

Known are the following indole compounds.

7) A compound of the formula:

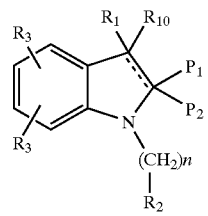

wherein $R_1$ is —X(CH$_2$)nAr, —X(CH$_2$)n$R_8$ etc., $R_2$ is hydrogen or Ar etc., $P_1$ is —X(CH$_2$)n$R_8$, $P_2$ is —X(CH$_2$)n$R_8$ etc., $R_3$ is hydrogen, $R_{11}$, OH, $C_{1-8}$ alkoxy, S(O)q $R_{11}$, N($R_6$)$_2$, Br, F, I, Cl, CF$_3$, NHCOR$_6$, —R$_{11}$CO$_2$R$_7$, —XR$_9$—Y, XY or —X(CH$_2$)n$R_8$, wherein methylene of the —X(CH$_2$)n$R_8$ may be unsubstituted or substituted by one more —(CH$_2$)nAr, $R_8$ is hydrogen, $R_{11}$ etc., $R_9$ is $C_{1-10}$ alkyl, $C_{2-10}$ alkenyl, phenyl, etc., $R_{11}$ is $C_{1-8}$ alkyl, $C_{2-8}$ alkenyl, $C_{2-8}$ alkynyl, etc., X is (CH$_2$)$_n$, O, S(O)$_q$, Y is CH, or —X(CH$_2$)nAr, Ar is phenyl, naphthyl, etc., q is 0, 1 or 2, n is an integer of 0 to 6, or a pharmaceutically acceptable salt thereof, which is useful for antagonizing endothelin receptors and treating cerebrovascular diseases (WO 94/14434, JP-A-8-504826).

8) A compound of the formula:

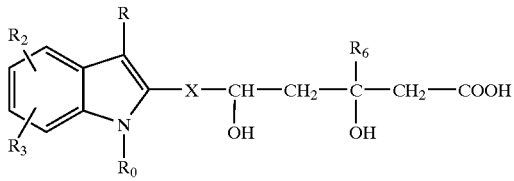

wherein one of R and $R_0$ is

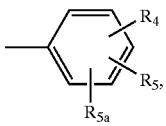

and the other is $C_{1-6}$ alkyl, $C_{1-6}$ cycloalkyl or phenyl-$(CH_2)_m$- wherein $R_4$, $R_5$ and $R_{5a}$ are hydrogen, etc.; m is 1, 2 or 3; $R_2$ is hydrogen, $C_{1-4}$ alkyl, $C_{3-6}$ cycloalkyl, $C_{1-4}$ alkoxy, phenoxy, benzyloxy, etc.; $R_3$ is hydrogen, $C_{1-3}$ alkyl, $C_{1-3}$ alkoxy, phenoxy, benzyloxy, etc.; X is —$(CH_2)_n$— or —CH=CH—; n is 0, 1, 2 or 3; $R_6$ is hydrogen or $C_{1-3}$ alkyl, or a salt thereof, which has cholesterol biosynthesis inhibiting activity (WO 84/02131).

DISCLOSURE OF INVENTION

We, the present inventors have studied various compounds and, as a result, have succeeded in the creation of a novel compound of the formula:

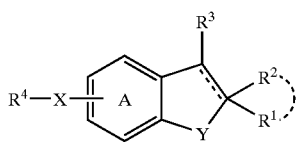

wherein $R^1$ and $R^2$ each represents a hydrogen atom or a hydrocarbon group which may be substituted, or $R^1$ and $R^2$ form, taken together with the adjacent carbon atom, a 3- to 8-membered carbo or heterocyclic ring which may be substituted;
$R^3$ represents a hydrogen atom, a lower alkyl which may be substituted or an aromatic group which may be substituted;
$R^4$ represents (1) an aromatic group which may be substituted, (2) an aliphatic hydrocarbon group substituted by an aromatic group which may be substituted, which hydrocarbon group may be further substituted or (3) an acyl;
X and Y each represents an oxygen atom or a sulfur atom which may be oxidized;
═══ represents a single bond or a double bond; and ring A represents a benzene ring which may be further substituted apart from the group of the formula: —X—$R^4$ wherein each symbol is as defined above,
provided that when X and Y are oxygen atoms and ═══ is a single bond, $R^4$ is not an acyl,
or a salt thereof [hereinafter sometimes referred to briefly as compound (I)], which compound is structurally characterized in that the benzene ring which is condensed with a 5-membered heterocyclic ring is substituted by a group of the formula: —X—$R^4$ wherein each symbol is as defined above.

We have found for the first time that compound (I), being based on its specific chemical structure, and a compound of the formula:

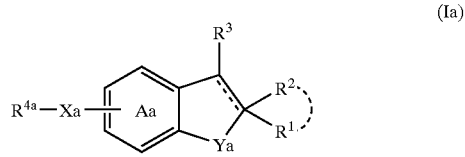

wherein $R^{4a}$ represents an aromatic group which may be substituted, an aliphatic hydrocarbon group which may be substituted or an acyl:
Xa represents an oxygen atom or a sulfur atom which may be oxidized;
Ya represents an oxygen atom, a sulfur atom which may be oxidized or an imino which may be substituted;
═══ represents a single bond or a double bond;
ring Aa represents a benzene ring which may be further substituted apart from (i) the group of the formula: —Xa-$R^{4a}$ wherein each symbol is as defined above, and (ii) an amino which may be substituted, and the other symbols are defied as above, provided that when Xa and Ya are oxygen atoms and ═══ is a single bond, $R^4$ is not an acyl, or a salt thereof [hereinafter sometimes referred to briefly as compound (Ia)], have an unexpected, excellent suppressive effect on neurodegeneration, low toxicity, excellent permeability to the brain and are therefore satisfactory as medicines for suppressing neurodegeneration. Compound (I) is within the scope of compound (Ia). On the basis of these findings, the inventors have completed the present invention.

Specifically, the present invention relates to:
1) compound (I);
2) a compound of the above 1), wherein $R^1$ and $R^2$ each is
   (i) a hydrogen atom or
   (ii) a $C_{1-6}$ alkyl, $C_{2-6}$ alkenyl, $C_{2-6}$ alkynyl, $C_{3-6}$ cycloalkyl or $C_{6-14}$ aryl group which may be substituted by 1 to 5 substituents selected from the group consisting of (1) halogen atoms, (2) $C_{1-3}$ alkylenedioxy, (3) nitro, (4) cyano, (5) optionally halogenated $C_{1-6}$ alkyl, (6) optionally halogenated $C_{2-6}$ alkenyl, (7) optionally halogenated $C_{2-6}$ alkynyl, (8) optionally halogenated $C_{1-6}$ cycloalkyl, (9) $C_{6-14}$ aryl, (10) optionally halogenated $C_{1-6}$ alkoxy, (11) optionally halogenated $C_{1-6}$ alkylthio, (12) hydroxy, (13) amino,
   (14) mono-$C_{1-6}$ alkylamino, (15) mono-$C_{6-14}$ arylamino, (16) di-$C_{1-6}$ alkylamino, (17) di-$C_{6-14}$ arylamino, (18) acyl selected from the group consisting of formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$ arylcarbonyl, $C_{7-16}$ aralkyl-carbonyl, $C_{6-14}$ aryloxycarbonyl, $C_{1-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-14}$ aryl-carbamoyl, 5- or 6-membered heterocycle carbamoyl, $C_{1-6}$ alkylsulfonyl, $C_{6-14}$ arylsulfonyl, $C_{1-6}$ alkylsulfinyl and $C_{6-14}$ arylsulfinyl, (19) acylamino selected from the group consisting of formylamino, $C_{1-6}$ alkyl-carboxamido, $C_{6-14}$ aryl-carboxamido, $C_{1-6}$ alkoxy-carboxamido, $C_{1-6}$ alkylsulfonylamino and $C_{6-14}$ arylsulfonylamino, (20) acyloxy selected from the group consisting of $C_{1-6}$ alkyl-carbonyloxy, $C_{6-4}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy and nicotinoyloxy, (21) 5- to 7-membered saturated cyclic amino which may be substituted by 1 to 3 substituents selected from the group consisting of $C_{1-6}$ alkyl, $C_{6-14}$ aryl and 5- to 10-membered aromatic heterocyclic group, (22) 5- to 10-membered aromatic heterocyclic group and (23) sulfo, or $R^1$ and $R^2$ form, taken together with the adjacent carbon atom, a $C_{3-8}$ cycloalkane or a 3- to 8-membered heterocyclic ring, each of which may be substituted by 1 to 3 substituents selected from the group consisting of $C_{1-6}$ alkyl, $C_{6-14}$ aryl, $C_{7-16}$, aralkyl, amino, mono-$C_{1-6}$ alkylamino, mono-$C_{6-14}$ arylamino, di-$C_{1-6}$ alkylamino, di-$C_{6-14}$ arylamino and 5- to 10-membered aromatic heterocyclic group;

$R^3$ is (i) a hydrogen atom, (ii) a $C_{1-6}$ alkyl which may be substituted by 1 to 5 substituents selected from the group consisting of (1) halogen atoms, (2) $C_{1-3}$ alkylenedioxy, (3) nitro, (4) cyano, (5) optionally halogenated $C_{1-6}$ alkyl, (6) optionally halogenated $C_{2-6}$ alkenyl, (7) optionally halogenated $C_{2-6}$ alkynyl, (8) optionally halogenated $C_{3-6}$ cycloalkyl, (9) $C_{1-4}$ aryl, (10) optionally halogenated $C_{1-6}$ alkoxy, (11) optionally halogenated $C_{1-6}$ alkylthio, (12) hydroxy, (13) amino, (14) mono-$C_{1-6}$ alkylamino, (15) mono-$C_{6-14}$ arylamino, (16) di-$C_{1-6}$ alkylamino, (17) dl-$C_{6-14}$ arylamino, (18) acyl selected from the group consisting of formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-14}$ aryl-carbamoyl, 5- or 6-membered heterocycle carbamoyl, $C_{1-6}$ alkylsulfonyl, $C_{6-14}$, arylsulfonyl, $C_{1-6}$ alkylsulfinyl and $C_{6-14}$, arylsulfinyl, (19) acylamino selected from the group consisting of formylamino, $C_{1-6}$ alkyl-carboxamido, $C_{6-14}$ aryl-carboxamido, $C_{1-6}$ alkoxy-carboxamido, $C_{1-6}$ alkylsulfonylamino and $C_{6-14}$, arylsulfonylamino, (20) acyloxy selected from the group consisting of $C_1$, alkyl-carbonyloxy, $C_{6-14}$, aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy and nicotinoyloxy, (21) 5- to 7-membered saturated cyclic amino which may be substituted by 1 to 3 substituents selected from the group consisting of $C_{1-6}$ alkyl, $C_{6-14}$ aryl and 5- to 10-membered aromatic heterocyclic group, (22) 5- to 10-membered aromatic heterocyclic group and (23) sulfo, or (iii) a $C_{6-14}$, aryl or a 5- to 14-membered aromatic heterocyclic group containing 1 to 4 hetero atoms selected from the group consisting of nitrogen, sulfur and oxygen atoms in addition to carbon atoms, each of which may be substituted by 1 to 3 substituents selected from the group consisting of (1) halogen atoms, (2) $C_{1-3}$ alkylenedioxy, (3) nitro, (4) cyano, (5) optionally halogenated $C_{1-6}$ alkyl, (6) optionally halogenated $C_{1-6}$ alkenyl, (7) optionally halogenated $C_{2-6}$ alkynyl, (8) optionally halogenated $C_{3-6}$ cycloalkyl, (9) optionally halogenated $C_{1-6}$ alkoxy, (10) optionally halogenated $C_{1-6}$ alkylthio, (11) hydroxy, (12) amino, (13) mono-$C_{1-6}$ alkylamino, (14) di-$C_{1-6}$ alkylamino, (15) 5- to 7-membered saturated cyclic amino which may be substituted by 1 to 3 substituents selected from the group consisting of $C_{1-4}$, alkyl, $C_{6-14}$, aryl and 5- to 10-membered aromatic heterocyclic group, (16) acyl selected from the group consisting of formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$, aryl-carbonyl, $C_{7-16}$ aralkyl-carbonyl, $C_{6-14}$, aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-14}$ aryl-carbamoyl, 5- or 6-membered heterocycle carbamoyl, $C_{1-6}$ alkylsulfonyl, $C_{6-14}$ arylsulfonyl, $C_{1-6}$ alkylsulfinyl and $C_{6-14}$ arylsulfinyl, (17) acylamino selected from the group consisting of formylamino, $C_{1-6}$ alkyl-carboxamido, $C_{6-14}$ aryl-carboxamido, $C_{1-6}$ alkoxy-carboxamido, $C_{1-6}$ alkylsulfonylamino and $C_{6-14}$ arylsulfonylamino, (18) acyloxy selected from the group consisting of $C_{1-6}$ alkyl-carbonyloxy, $C_{6-14}$, aryl-carbonyloxy, $C_{1-6}$-alkoxy-carbonyloxy, mono-$C_{1-6}$ alkyl-carbamoyloxy, di-$C_{1-6}$ alkyl-carbamoyloxy, $C_{6-14}$ aryl-carbamoyloxy and nicotinoyloxy, (19) sulfo, (20) $C_{6-14}$ aryl and (21) $C_{6-14}$, aryloxy; $R^4$ is (i) a $C_{6-14}$ aryl or a 5- to 14-membered aromatic heterocyclic group containing 1 to 4 hetero atoms selected from the group consisting of nitrogen, sulfur and oxygen atoms in addition to carbon atoms, each of which may be substituted by 1 to 3 substituents selected from the group consisting of (1) halogen atoms, (2) $C_{1-3}$ alkylenedioxy, (3) nitro, (4) cyano, (5) optionally halogenated $C_{1-6}$ alkyl, (6) optionally halogenated $C_{2-6}$ alkenyl, (7) optionally halogenated $C_{2-6}$ alkynyl, (8) optionally halogenated $C_{1-6}$ cycloalkyl, (9) optionally halogenated $C_{1-6}$ alkoxy, (10) optionally halogenated $C_{1-6}$ alkylthio, (11) hydroxy, (12) amino, (13) mono-$C_{1-6}$ alkylamino, (14) di-$C_{1-6}$ alkylamino, (15) 5- to 7-membered saturated cyclic amino which may be substituted by 1 to 3 substituents selected from the group consisting of $C_{1-6}$ alkyl, $C_{6-14}$ aryl and 5- to 10-membered aromatic heterocyclic group, (16) acyl selected from the group consisting of formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$, aryl-carbonyl, $C_{7-16}$ aralkyl-carbonyl, $C_{1-6}$ aryloxy-carbonyl, $C_{1-6}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-14}$ aryl-carbamoyl, 5- or 6-membered heterocycle carbamoyl, $C_{1-6}$ alkylsulfonyl, $C_{6-14}$ arylsulfonyl, $C_{1-6}$ alkylsulfinyl and $C_{6-14}$ arylsulfinyl, (17) acylamino selected from the group consisting of formylamino, $C_{1-6}$ alkyl-carboxamido, $C_{6-14}$ aryl-carboxamido, $C_{1-6}$ alkoxy-carboxamido, $C_{1-6}$ alkylsulfonylamino and $C_{6-14}$ arylsulfonylamino, (18) acyloxy selected from the group consisting of $C_{1-6}$ alkyl-carbonyloxy, $C_{6-14}$, aryl-carbonyloxy, $C_{1-6}$-alkoxy-carbonyloxy, mono-$C_{1-6}$ alkyl-carbamoyloxy, di-$C_{1-6}$ alkyl-carbamoyloxy, $C_{6-14}$ aryl-carbamoyloxy and nicotinoyloxy, (19) sulfo, (20) $C_{6-14}$ aryl and (21) $C_{6-14}$, aryloxy, (ii) an aliphatic hydrocarbon group selected form the group consisting of $C_{1-6}$ alkyl, $C_{2-6}$ alkenyl, $C_{2-6}$ alkynyl and $C_{3-6}$ cycloalkyl, which hydrocarbon group substituted by 1 to 3 $C_{6-14}$ aryl or 5- to 14-membered aromatic heterocyclic group containing 1 to 4 hetero atoms selected from the group consisting of nitrogen, sulfur and oxygen atoms in addition to carbon atoms, each of which may be substituted by 1 to 3 substituents selected from the group consisting of (1) halogen atoms, (2) $C_{1-3}$ alkylenedioxy, (3) nitro, (4) cyano, (5) optionally halogenated $C_{1-6}$ alkyl, (6) optionally halogenated $C_{2-6}$ alkenyl, (7) optionally halogenated $C_{2-6}$ alkynyl, (8) optionally halogenated $C_{3-6}$ cycloalkyl, (9) optionally halogenated $C_{1-6}$ alkoxy, (10) optionally halogenated $C_{1-6}$ alkylthio, (11) hydroxy, (12) amino, (13) mono-$C_{1-6}$ alkylamino, (14) di-$C_{1-6}$ alkylamino, (15) 5- to 7-membered saturated cyclic amino which may be substituted by 1 to 3 substituents selected from the group consisting of $C_{1-6}$ alkyl, $C_{6-14}$ aryl and 5- to 10-membered aromatic heterocyclic group, (16) acyl selected from the group consisting of formyl, carboxy, carbamoyl, $C_{1-5}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl., $C_{6-14}$, aryloxy-carbonyl, $C_{7-16}$ aralkyloxy-carbonyl, 5- or 6-membered heterocycle carbonyl, mono-$C_{1-6}$ alkyl-carbamoyl, di-$C_{1-4}$ alkyl-carbamoyl, $C_{6-14}$ aryl-carbamoyl, 5- or 6-membered heterocycle carbamoyl, $C_{1-6}$ alkylsulfonyl, $C_{6-14}$ arylsulfonyl, $C_{1-6}$ alkylsulfinyl and $C_{6-14}$, arylsulfinyl, (17) acylamino selected from the group consisting of formylamino, $C_{1-6}$ alkyl-carboxamido, $C_{6-14}$ aryl-carboxamido, $C_{1-6}$ alkoxy-carboxamido, $C_{1-6}$ alkylsulfonylamino and $C_{6-14}$ arylsulfonylamino, (18) acyloxy selected from the group consisting of $C_{1-6}$-alkyl-carbonyloxy, $C_{6-1-4}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy and nicotinoyloxy, (19) sulfo, (20) $C_{6-14}$, aryl and (21) $C_{6-14}$, aryloxy, which hydrocarbon group may be further substituted by 1 to 5 substituents selected from the group consisting of (1) halogen atoms, (2) $C_{1-3}$ alkylenedioxy, (3) nitro, (4) cyano, (5) optionally halogenated $C_{1-4}$ alkyl, (6) optionally halogenated $C_{1-6}$ alkenyl, (7) optionally halogenated $C_{2-6}$ alkynyl, (8) optionally halogenated $C_{1-6}$ cycloalkyl, (9) $C_{6-14}$ aryl, (10) optionally halogenated $C_{1-6}$ alkoxy, (11) optionally halogenated $C_{1-6}$ alkylthio, (12) hydroxy, (13) amino, (14) mono-$C_{1-6}$ alkylamino, (15) mono-$C_{6-14}$ arylamino, (16) di-$C_{1-6}$ alkylamino, (17) di-$C_{6-14}$ arylamino, (18) acyl selected from the group consisting of formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{1-6}$ aryl-carbamoyl, 5- or 6-membered heterocycle carbamoyl, $C_{1-6}$ alkylsulfonyl, $C_{6-14}$, arylsulfonyl, $C_{1-6}$ alkylsulfinyl and $C_{6-14}$ arylsulfinyl, (19) acylamino selected from the group consisting of formylamino, $C_{1-6}$ alkyl-carboxamido, $C_{6-14}$ aryl-carboxamido, $C_{1-6}$ alkoxy-carboxamido, $C_{1-6}$ alkylsulfonylamino and $C_{6-14}$, arylsulfonylamino, (20) acyloxy selected from the group consisting of $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy and nicotinoyloxy, (21) 5- to 7-membered saturated cyclic amino which may be substituted by 1 to 3 substituents selected from the group consisting of $C_{1-6}$ alkyl, $C_{6-14}$ aryl and 5- to 10-membered aromatic heterocyclic group, (22) 5- to 10-membered aromatic heterocyclic group and (23) sulfo, or (iii) an acyl of the formula: —(C=O)—$R^5$, —(C=O)—$OR^5$, (C=O)—$NR^5R^6$, —(C=S)—$NHR^5$, —$SO_2$—$R^{5a}$ or —SO—$R^{5a}$ wherein $R^5$ is (a) a hydrogen atom, (b) a $C_{6-14}$ aryl or a 5- to 14-membered aromatic heterocyclic group containing 1 to 4 hetero atoms selected from the group consisting of nitrogen, sulfur and oxygen atoms in addition to carbon atoms, each of which may be substituted by 1 to 3 substituents selected from the group consisting of (1) halogen atoms, (2) $C_{1-3}$ alkylenedioxy, (3) nitro, (4) cyano, (5) optionally halogenated $C_{1-6}$ alkyl, (6) optionally halogenated $C_{1-6}$ alkenyl, (7) optionally halogenated $C_{2-6}$ alkynyl, (8) optionally halogenated $C_{3-6}$ cycloalkyl, (9) optionally halogenated $C_{1-6}$ alkoxy, (10) optionally halogenated $C_{1-6}$ alkylthio, (11) hydroxy, (12) amino, (13) mono-$C_{1-6}$ alkylamino, (14) di-$C_{1-6}$ alkylamino, (15) 5- to 7-membered saturated cyclic amino which may be substituted by 1 to 3 substituents selected from the group consisting of $C_{1-6}$ alkyl, $C_{6-14}$ aryl and 5- to 10-membered aromatic heterocyclic group, (16) acyl selected from the group consisting of formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{1-6}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-14}$ aryl-carbamoyl, 5- or 6-membered heterocycle carbamoyl, $C_{1-6}$ alkylsulfonyl, $C_{6-14}$ arylsulfonyl, $C_{1-6}$ alkylsulfinyl and $C_{6-14}$ arylsulfinyl, (17) acylamino selected from the group consisting of formylamino, $C_{1-6}$ alkyl-carboxamido, $C_{6-14}$ aryl-carboxamido, $C_{1-6}$ alkoxy-carboxamido, $C_{1-6}$ alkylsulfonylamino and $C_{6-14}$, arylsulfonylamino, (18) acyloxy selected from the group consisting of $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy and nicotinoyloxy, (19) sulfo, (20) $C_{6-14}$ aryl and (21) $C_{6-14}$ aryloxy, or (c) a $C_{1-6}$ alkyl, $C_{2-6}$ alkenyl, $C_{2-6}$ alkynyl or $C_{3-6}$ cycloalkyl group which may be substituted by 1 to 5 substituents selected from the group consisting of (1) $C_{1-1}$, aryl or 5- to 14-membered aromatic heterocyclic group containing 1 to 4 hetero atoms selected from the group consisting of nitrogen, sulfur and oxygen atoms in addition to carbon atoms, each of which may be substituted by 1 to 3 substituents selected from the group consisting of (1') halogen atoms, (2') $C_{1-3}$ alkylenedioxy, (3') nitro, (4') cyano, (5') optionally halogenated $C_{1-6}$ alkyl, (6') optionally halogenated $C_{2-6}$ alkenyl, (7') optionally halogenated $C_{2-6}$ alkynyl, (8') optionally halogenated $C_{3-6}$ cycloalkyl, (9') optionally halogenated $C_{1-6}$ alkoxy, (10') optionally halogenated $C_{1-6}$ alkylthio, (11') hydroxy, (12') amino, (13') mono-$C_{1-6}$ alkylamino, (14') di-$C_{1-6}$ alkylamino, (15') 5- to 7-membered saturated cyclic amino which may be substituted by 1 to 3 substituents selected from the group consisting of $C_{1-6}$ alkyl, $C_{6-14}$ aryl and 5- to 10-membered aromatic heterocyclic group, (16') acyl selected from the group consisting of formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-14}$ aryl-carbamoyl, 5- or 6-membered heterocycle carbamoyl, $C_{1-6}$ alkylsulfonyl, $C_{6-14}$, arylsulfonyl, $C_{1-6}$ alkylsulfinyl and $C_{6-14}$ arylsulfinyl, (17') acylamino selected from the group consisting of formylamino, $C_{1-6}$ alkyl-carboxamido, $C_{6-14}$, aryl-carboxamido, $C_{1-6}$ alkoxy-carboxamido, $C_{1-6}$ alkylsulfonylamino and $C_{6-14}$, arylsulfonylamino, (18') acyloxy selected from the group consisting of $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy and nicotinoyloxy, (19') sulfo, (20') $C_{6-14}$ aryl and (21') $C_{6-14}$ aryloxy, (2) halogen atoms, (3) $C_{1-3}$ alkylenedioxy, (4) nitro, (5) cyano, (6) optionally halogenated $C_{1-6}$ alkyl, (7) optionally halogenated $C_{2-6}$ alkenyl, (8) optionally halogenated $C_{2-6}$ alkynyl, (9) optionally halogenated $C_{3-6}$ cycloalkyl, (10) optionally halogenated $C_{1-6}$ alkoxy, (11)

optionally halogenated $C_{1-6}$ alkylthio, (12) hydroxy, (13) amino, (14) mono-$C_{1-6}$ alkylamino, (15) di-$C_{1-6}$ alkylamino, (16) 5- to 7-membered saturated cyclic amino which may be substituted by 1 to 3 substituents selected from the group consisting of $C_{1-6}$ alkyl, $C_{6-14}$ aryl and 5- to 10-membered aromatic heterocyclic group, (17) acyl selected from the group consisting of formyl, carboxy, carbamoyl, $C_{1-6}$ alkyl-carbonyl, $C_{3-6}$ cycloalkyl-carbonyl, $C_{1-6}$, alkoxy-carbonyl, $C_{6-14}$ aryl-carbonyl, $C_{7-16}$ aralkyl-carbonyl, $C_{4-14}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-14}$, aryl-carbamoyl, 5- or 6-membered heterocycle carbamoyl, $C_{1-6}$ alkylsulfonyl, $C_{6-14}$ arylsulfonyl, $C_{1-6}$ alkylsulfinyl and $C_{1-14}$, arylsulfinyl, (18) acylamino selected from the group consisting of formylamino, $C_{1-6}$ alkyl-carboxamido, $C_{6-14}$, aryl-carboxamido, $C_{1-6}$ alkoxy-carboxamido, $C_{1-6}$ alkylsulfonylamino and $C_{6-14}$, arylsulfonylamino, (19) acyloxy selected from the group consisting of $C_{1-6}$ alkyl-carbonyloxy, $C_{1-6}$ aryl-carbonyloxy, $C_{1-6}$ alkoxy-carbonyloxy, mono-$C_{6-14}$ alkyl-carbamoyloxy, di-$C_{1-6}$ alkyl-carbamoyloxy, $C_{6-14}$ aryl-carbamoyloxy and nicotinoyloxy and (20) sulfo;

$R^{5a}$ is (a) a $C_{6-14}$, aryl or a 5- to 14-membered aromatic heterocyclic group containing 1 to 4 hetero atoms selected from the group consisting of nitrogen, sulfur and oxygen atoms in addition to carbon atoms, each of which may be substituted by 1 to 3 substituents selected from the group consisting of (1) halogen atoms, (2) $C_{1-3}$ alkylenedioxy, (3) nitro, (4) cyano, (5) optionally halogenated $C_{1-6}$ alkyl, (6) optionally halogenated $C_{2-6}$ alkenyl, (7) optionally halogenated $C_2$, alkynyl, (8) optionally halogenated $C_{3-6}$ cycloalkyl, (9) optionally halogenated $C_{1-6}$ alkoxy, (10) optionally halogenated $C_{1-6}$ alkylthio, (11) hydroxy, (12) amino, (13) mono-$C_{1-6}$ alkylamino, (14) di-$C_{1-6}$ alkylamino, (15) 5- to 7-membered saturated cyclic amino which may be substituted by 1 to 3 substituents selected from the group consisting of $C_{1-6}$ alkyl, $C_{6-14}$, aryl and 5- to 10-membered aromatic heterocyclic group, (16) acyl selected from the group consisting of formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$, aryl-carbonyl, $C_{7-6}$ aralkyl-carbonyl, $C_{1-6}$ aryloxy-carbonyl, $C_{1-6}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-14}$ aryl-carbamoyl, 5- or 6-membered heterocycle carbamoyl, $C_{1-6}$ alkylsulfonyl, $C_{6-14}$, arylsulfonyl, $C_1$, alkylsulfinyl and $C_{6-14}$, arylsulfinyl, (17) acylamino selected from the group consisting of formylamino, $C_{1-6}$ alkyl-carboxamido, $C_{6-14}$ aryl-carboxamido, $C_{1-6}$ alkoxy-carboxamido, $C_{1-6}$, alkylsulfonylamino and $C_{6-14}$, arylsulfonylamino, (18) acyloxy selected from the group consisting of $C_{1-6}$ alkyl-carbonyloxy, $C_{6-14}$ aryl-carbonyloxy, $C_{1-6}$ alkoxy-carbonyloxy, mono-$C_{6-14}$ alkyl-carbamoyloxy, di-$C_{1-6}$ alkyl-carbamoyloxy, $C_{6-14}$, aryl-carbamoyloxy and nicotinoyloxy, (19) sulfo, (20) $C_{6-14}$, aryl and (21) $C_{6-14}$, aryloxy, or (b) a $C_{1-6}$ alkyl, $C_{2-14}$ alkenyl, $C_{2-6}$ alkynyl or $C_{1-6}$ cycloalkyl group which may be substituted by 1 to 5 substituents selected from the group consisting of (1) a $C_{6-14}$, aryl or 5- to 14-membered aromatic heterocyclic group containing 1 to 4 hetero atoms selected from the group consisting of nitrogen, sulfur and oxygen atoms in addition to carbon atoms, each of which may be substituted by 1 to 3 substituents selected from the group consisting of (1') halogen atoms, (2') $C_{1-3}$ alkylenedioxy, (3') nitro, (4') cyano, (5') optionally halogenated $C_{1-6}$ alkyl, (6') optionally halogenated $C_{2-6}$ alkenyl, (7') optionally halogenated $C_{2-6}$ alkynyl, (8') optionally halogenated $C_{3-6}$ cycloalkyl, (9') optionally halogenated $C_{1-6}$ alkoxy, (10') optionally halogenated $C_{1-6}$ alkylthio, (11') hydroxy, (12') amino, (13') mono-$C_{1-6}$ alkylamino, (14') di-$C_{1-6}$ alkylamino, (15') 5- to 7-membered saturated cyclic amino which may be substituted by 1 to 3 substituents selected from the group consisting of $C_{1-6}$ alkyl, $C_{6-14}$, aryl and 5- to 10-membered aromatic heterocyclic group, (16') acyl selected from the group consisting of formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{1-6}$, aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-14}$ aryl-carbamoyl, 5- or 6-membered heterocycle carbamoyl, $C_{1-6}$ alkylsulfonyl, $C_{6-14}$ arylsulfonyl, $C_{1-6}$ alkylsulfinyl and $C_{1-1}$, arylsulfinyl, (17') acylamino selected from the group consisting of formylamino, $C_{1-6}$ alkyl-carboxamido, $C_{6-14}$ aryl-carboxamido, $C_{1-6}$ alkoxy-carboxamido, $C_{1-6}$ alkylsulfonylamino and $C_{6-4}$ arylsulfonylamino, (18') acyloxy selected from the group consisting of $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{1-6}$ aryl-carbamoyloxy and nicotinoyloxy, (19') sulfo, (20') $C_{6-14}$ aryl and (21') $C_{6-14}$ aryloxy, (2) halogen atoms, (3) $C_{1-3}$ alkylenedioxy, (4) nitro, (5) cyano, (6) optionally halogenated $C_{1-6}$ alkyl, (7) optionally halogenated $C_{2-6}$ alkenyl, (8) optionally halogenated $C_{2-6}$ alkynyl, (9) optionally halogenated $C_{3-6}$ cycloalkyl, (10) optionally halogenated $C_{1-6}$ alkoxy, (11) optionally halogenated $C_{1-6}$ alkylthio, (12) hydroxy, (13) amino, (14) mono-$C_{1-6}$ alkylamino, (15) di-$C_{1-6}$ alkylamino, (16) 5- to 7-membered saturated cyclic amino which may be substituted by 1 to 3 substituents selected from the group consisting of $C_{1-6}$ alkyl, $C_{6-14}$ aryl and 5- to 10-membered aromatic heterocyclic group, (17) acyl selected from the group consisting of formyl, carboxy, carbamoyl, $C_{1-6}$ alkyl-carbonyl, $C_{1-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{1-6}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{1-1}$, aryl-carbamoyl, 5- or 6-membered heterocycle carbamoyl, $C_{1-6}$ alkylsulfonyl, C, arylsulfonyl, $C_{1-6}$ alkylsulfinyl and $C_{1-1}$, arylsulfinyl, (18) acylamino selected from the group consisting of formylamino, $C_{1-6}$ alkyl-carboxamido, $C_{6-14}$, aryl-carboxamido, $C_{1-6}$ alkoxy-carboxamido, $C_{1-6}$ alkylsulfonylamino and $C_{1-14}$ arylsulfonylamino, (19) acyloxy selected from the group consisting of $C_{1-6}$ alkyl-carbonyloxy, $C_{6-14}$, aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{1-6}$ aryl-carbamoyloxy and nicotinoyloxy and (20) sulfo; and $R^6$ is a hydrogen atom or a $C_{1-6}$ alkyl; and ring A is a benzene ring which may be further substituted by 1 to 3 substituents selected from the group consisting of (1) halogen atoms, (2) $C_{1-3}$ alkylenedioxy, (3) nitro, (4) cyano, (5) optionally halogenated $C_{1-6}$ alkyl, (6) optionally halogenated $C_{1-6}$ alkenyl, (7) optionally halogenated $C_{1-6}$ alkynyl, (8) optionally halogenated $C_{3-6}$ cycloalkyl, (9) optionally halogenated $C_{1-6}$ alkoxy, (10) optionally halogenated $C_{1-6}$ alkylthio, (11) hydroxy, (12) amino, (13) mono-$C_{1-6}$ alkylamino, (14) di-$C_{1-6}$ alkylamino, (15) 5- to 7-membered saturated cyclic amino which may be substituted by 1 to 3 substituents selected from the group consisting of $C_{1-6}$ alkyl, $C_{6-14}$, aryl and 5- to 10-membered aromatic heterocyclic group, (16) acyl selected from the group consisting of formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{1-6}$ aryloxy-carbonyl, $C_{3-6}$, aralkyloxy-carbonyl, 5- or 6-membered heterocycle carbonyl, mono-$C_{1-6}$ alkyl-carbamoyl, di-$C_{1-6}$ alkyl-carbamoyl, $C_{1-6}$ aryl-carbamoyl, 5- or 6-membered heterocycle carbamoyl, $C_{1-6}$ alkylsulfonyl, $C_{6-14}$ arylsulfonyl, $C_{1-6}$ alkylsulfinyl and $C_{6-14}$ arylsulfinyl, (17) acylamino selected from the group consisting of formylamino, $C_{1-6}$ alkyl-carboxamido, $C_{6-14}$ aryl-carboxamido, $C_{1-6}$ alkoxy-carboxamido, $C_{1-6}$ alkylsulfonylamino and $C_{6-14}$ arylsulfonylamino, (18) acyloxy selected from the group consisting of $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy and nicotinoyloxy, (19) sulfo, (20) $C_{6-14}$ aryl and (21) $C_{6-14}$ aryloxy.

3) a compound of the above 1), wherein $R^1$ and $R^2$ each is a $C_{1-6}$ alkyl which may be substituted, or $R^1$ and $R^2$ form, taken together with the adjacent carbon atom, a 3- to 8-membered carbo or heterocyclic ring which may be substituted;

4) a compound of the above 1), wherein $R^3$ is an aromatic group which may be substituted;

5) a compound of the above 1), wherein $R^4$ is (i) an aliphatic hydrocarbon group substituted by an aromatic group which may be substituted, which hydrocarbon group may be further substituted or (ii) an acyl;

6) a compound of the above 1), wherein X is an oxygen atom;

7) a compound of the above 1), wherein Y is an oxygen atom;

8) a compound of the above 7), wherein a group of the formula: —X—$R^4$ is substituted on the 5-position of the benzofuran ring;

9) a compound of the above 1), which is a compound of the formula:

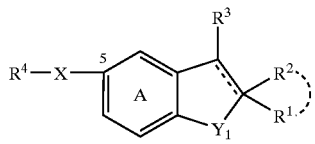

wherein each symbol is as defined above, or a salt thereof;

10) a compound of the above 1), wherein $R^1$ and $R^2$ each is a $C_{1-6}$ alkyl which may be substituted by 1 to 3 substituents selected from the group consisting of (1) $C_{6-14}$ aryl, (2) $C_{1-6}$ alkoxy, (3) $C_{1-6}$ alkylthio, (4) hydroxy, (5) amino, (6) mono-$C_{1-6}$ alkylamino, (7) mono-$C_{6-14}$ arylamino, (8) di-$C_{1-6}$ alkylamino, (9) di-$C_{6-14}$ arylamino, (10) carboxy, (11) $C_{1-6}$ alkylsulfonyl, (12) $C_{6-14}$ arylsulfonyl, (13) $C_{1-6}$ alkylsulfinyl, (14) $C_{6-14}$ arylsulfinyl and (15) 5- to 7-membered saturated cyclic amino which may be substituted by 1 to 3 substituents selected from the group consisting of $C_{1-6}$ alkyl, $C_{6-14}$, aryl and 5- to 10-membered aromatic group, or $R^1$ and $R^2$ form, taken together with the adjacent carbon atom, a 3- to 8-membered carbo or heterocyclic ring which may be substituted by 1 to 3 substituents selected from the group consisting of $C_{1-6}$ alkyl, $C_{6-14}$ aryl, $C_{7-16}$ aralkyl and 5- to 10-membered aromatic heterocyclic group;

$R^3$ is a phenyl, 1-naphthyl, 2-naphthyl, 2-thienyl, 3-thienyl, 2-pyridyl, 3-pyridyl, 4-pyridyl, 2-quinolyl, 3-quinolyl, 1-isoquinolyl, 1-indolyl, 2-indolyl or 2-benzothiazolyl group, each of which may be substituted by 1 to 3 substituents selected from the group consisting of (1) halogen atoms, (2) $C_{1-6}$ alkyl, (3) $C_{1-6}$ alkoxy, (4) mono-$C_{1-6}$ alkylamino, (5) di-$C_{1-6}$ alkylamino and (6) 5- to 7-membered saturated cyclic amino which may be substituted by 1 to 3 substituents selected form the group consisting of $C_{1-6}$ alkyl, $C_{6-14}$ aryl and 5- to 10-membered aromatic group;

$R^4$ is (i) $C_{1-6}$ alkyl substituted by a phenyl, 1-naphthyl, 2-naphthyl, 2-thienyl, 3-thienyl, 2-pyridyl, 3-pyridyl, 4-pyridyl, 2-quinolyl, 3-quinolyl, 1-isoquinolyl, 1-indolyl, 2-indolyl or 2-benzothiazolyl group, each of which may be substituted by 1 to 3 substituents selected from the group consisting of (1) halogen atoms, (2) $C_{1-6}$ alkyl, (3) $C_{1-6}$ alkoxy, (4) hydroxy, (5) amino, (6) mono-$C_{1-6}$ alkylamino, (7) di-$C_{1-6}$ alkylamino, (8) carboxy and (9) 5- to 7-membered saturated cyclic amino which may be substituted by 1 to 3 substituents selected from the group consisting of $C_{1-6}$ alkyl, $C_{6-14}$ aryl and 5- to 10-membered aromatic group, which $C_{1-6}$ alkyl may be further substituted by carboxy or $C_{1-6}$ alkoxy-carbonyl, or (ii) a $C_{1-6}$alkyl-carbonyl, $C_{3-6}$ cycloalkyl-carbonyl, $C_{6-14}$ aryl-carbonyl or $C_{7-16}$ aralkyl-carbonyl group, each of which may be substituted by 1 to 3 substituents selected from the group consisting of halogen atoms, $C_{1-6}$ alkyl, $C_{1-6}$ alkoxy, hydroxy, amino, mono-$C_{1-6}$ alkylamino, di-$C_{1-6}$ alkylamino and carboxy;

X is an oxygen atom;

Y is an oxygen atom; and ring A is a benzene ring which may be further substituted by 1 to 3 substituents selected from the group consisting of halogen atoms, optionally halogenated $C_{1-6}$ alkyl, optionally halogenated $C_{1-6}$ alkoxy, amino, mono-$C_{1-6}$ alkylamino and di-$C_{1-6}$ alkylamino;

11) a compound of the above 1), wherein $R^1$ and $R^2$ each is a $C_{1-6}$ alkyl which may be substituted by 1 to 3 substituents selected from the group consisting of $C_{6-1}$ aryl, $C_{1-6}$ alkoxy, $C_{1-6}$ alkylthio, hydroxy, amino, mono-$C_{6-14}$ alkylamino, mono-$C_{1-6}$ arylamino, di-$C_{1-6}$ alkylamino, di-$C_{6-14}$ arylamino, carboxy, $C_{1-6}$ alkylsulfonyl, $C_{6-14}$ arylsulfonyl, $C_{1-6}$ alkylsulfinyl and $C_{6-14}$ arylsulfinyl, or $R^1$ and $R^2$ form, taken together with the adjacent carbon atom, a piperidine which may be substituted by 1 to 3 substituents selected from the group consisting of $C_{1-6}$ alkyl, $C_{6-14}$ aryl and $C_{7-16}$ aralkyl;

$R^3$ is a phenyl which may be substituted by 1 to 3 substituents selected from the group consisting of halogen atoms, $C_{1-6}$ alkyl, $C_{1-6}$ alkoxy, amino, mono-$C_{1-6}$ alkylamino and di-$C_{1-6}$ alkylamino:

$R^4$ is (i) $C_{1-6}$ alkyl substituted by a phenyl or pyridyl, each of which may be substituted by 1 to 3 substituents selected from the group consisting of halogen atoms, $C_{1-6}$ alkyl, $C_{1-6}$ alkoxy, hydroxy, amino, mono-$C_{1-6}$ alkylamino, di-$C_{1-6}$ alkylamino and carboxy, or (ii) an acyl of the formula: —(C=O)—$R^{5'}$ wherein $R^{5'}$ is a phenyl or phenyl-$C_{1-6}$ alkyl, each of which may be substituted by 1 to 3 substituents selected from the group consisting of halogen atoms, $C_{1-6}$ alkyl, $C_{1-6}$ alkoxy, hydroxy, amino, mono-$C_{1-6}$ alkylamino, di-$C_{1-6}$ alkylamino and carboxy;

X is an oxygen atom;

Y is an oxygen atom; and ring A is a benzene ring which may be further substituted by 1 to 3 substituents selected from the group consisting of halogen atoms, optionally halogenated $C_{1-6}$ alkyl, optionally halogenated $C_{1-6}$ alkoxy, amino, mono-$C_{1-6}$ alkylamino and di-$C_{1-6}$ alkylamino;

12) a compound of the above 1) which is a compound of the formula:

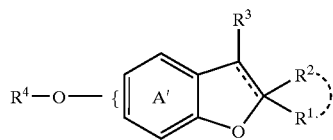

wherein $R^1$ and $R^2$ each is $C_{1-6}$ alkyl which may be substituted by 6-membered saturated cyclic amino substituted by a phenyl, or $R^1$ and $R^2$ form, taken together with the adjacent carbon atom, a piperidine substituted by a $C_{1-6}$ alkyl or a $C_{7-16}$ aralkyl:

$R^3$ is (i) a hydrogen atom, or (ii) a phenyl which may be substituted by 1 to 3 substituents selected from the group consisting of (1) $C_{1-6}$ alkyl, (2) di-$C_{1-6}$ alkylamino and (3) 6-membered saturated cyclic amino which may be substituted by a $C_{1-6}$ alkyl, $R^4$ is (i) a phenyl which may be substituted by 1 to 3 substituents selected from the group consisting of nitro and $C_{1-6}$ alkyl-carboxamido, (ii) a $C_{1-6}$ alkyl or $C_{2-6}$ alkenyl group substituted by 1 to 3 of phenyl, quinolyl or pyridyl, each of which may be substituted by 1 to 3 substituents selected from the group consisting of $C_{1-6}$ alkoxy, $C_{1-6}$ alkylthio, $C_{1-6}$ alkoxy-carbonyl, $C_{1-6}$ alkylsulfonyl and $C_{1-6}$ alkylsulfinyl, which $C_{1-6}$ alkyl or $C_2$, alkenyl group may be further substituted by a phenyl, carboxy or $C_{1-6}$ alkoxy-carbonyl, or (iii) an acyl of the formula: —(C=O)—$R^5$ wherein $R^{5''}$ is phenyl substituted by a $C_{1-6}$ alkoxy; and ring A' is a benzene ring which may be further substituted by 1 to 3 $C_{1-6}$ alkyl;

13) a compound of the above 1) which is 3-(4-isopropylphenyl)-5-(4-methoxybenzyloxy)-2,2,4,6,7-pentamethyl-2,3-dihydrobenzofuran, 3-(4-isopropylphenyl)-2,4,6,7-tetramethylbenzofuran-5-yl 4-methoxybenzoate, 3-(4-isopropylphenyl)-5-(4-methoxybenzyloxy)-2,4,6,7-tetramethylbenzofuran, 3-(4-isopropylphenyl)-5-(4-methoxybenzyloxy)-1',4,6,7-tetramethylspiro[benzofuran-2(3H),4'-piperidine], or a salt thereof;

14) a process for producing compound (I), which comprises reacting a compound of the formula:

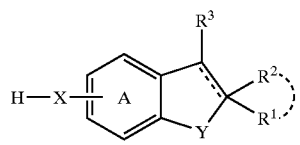

wherein each symbol is as defined above, or a salt thereof with a compound of the formula: $R^4$-L wherein L represents a leaving group and $R^4$ is as defined above, or salt thereof;

15) a pharmaceutical composition which comprises compound (I);

16) a composition of the above 15) which is an agent for suppressing neurodegeneration;

17) a composition of the above 15) which is an agent for suppressing β-amyloid toxicity;

18) a composition of the above 15) which is an agent for preventing and/or treating neurodegenerative diseases;

19) an agent for preventing and/or treating neurodegenerative diseases which comprises compound (Ia);

20) an agent of the above 19) which is an agent for suppressing β-amyloid toxicity;

21) an agent of the above 19) which is an agent for preventing and/or treating neurodegenerative diseases;

22) a method for suppressing neurodegeneration in mammal, which comprises administering to said mammal an effective amount of compound (Ia) with a pharmaceutically acceptable excipient, carrier or diluent;

23) use of compound (Ia) for manufacturing a pharmaceutical composition for suppressing neurodegeneration; and so forth.

In the formulae, the "hydrocarbon group" of the "hydrocarbon group which may be substituted" for $R^1$ or $R^2$ includes, for example, an acyclic or cyclic hydrocarbon group such as alkyl, alkenyl, alkynyl, cycloalkyl, aryl, etc. Among them, $C_{1-16}$ acyclic or cyclic hydrocarbon group is preferable.

The preferred "alkyl" is for example $C_{1-6}$ alkyl such as methyl, ethyl, propyl, isopropyl, butyl, isobutyl, sec-butyl, tert-butyl, pentyl, hexyl, etc.

The preferred "alkenyl" is for example $C_{2-6}$ alkenyl such as vinyl, allyl, isopropenyl, butenyl, isobutenyl, sec-butenyl, etc.

The preferred "alkynyl" is for example $C_{2-6}$ alkynyl such as ethynyl, propargyl, butynyl, 1-hexynyl, etc.

The preferred "cycloalkyl" is for example $C_{3-6}$ cycloalkyl such as cyclopropyl, cyclobutyl, cyclopentyl, cyclohexyl, etc.

The preferred "aryl" is for example $C_{6-14}$ aryl such as phenyl, 1-naphthyl, 2-naphthyl, biphenylyl, 2-anthryl, etc.

Examples of the "substituents" of the "hydrocarbon group which may be substituted" include halogen atoms (e.g., fluoro, chloro, bromo, iodo, etc.), $C_{1-3}$ alkylenedioxy (e.g., methylenedioxy, ethylenedioxy, etc.), nitro, cyano, optionally halogenated $C_{1-6}$ alkyl, optionally halogenated $C_{2-6}$ alkenyl, optionally halogenated $C_{2-6}$ alkynyl, optionally halogenated $C_{1-6}$ cycloalkyl, $C_{6-14}$ aryl (e.g., phenyl, 1-naphthyl, 2-naphthyl, biphenylyl, 2-anthryl, etc.), optionally halogenated $C_{1-6}$ alkoxy, optionally halogenated $C_{1-6}$ alkylthio, hydroxy, amino, mono-$C_{1-6}$ alkylamino (e.g., methylamino, ethylamino, etc.), mono-$C_{6-14}$ arylamino (e.g., phenylamino, 1-naphthylamino, 2-naphthylamino, etc.), di-$C_{1-6}$ alkylamino (e.g., dimethylamino, diethylamino, etc.), di-$C_{6-14}$ arylamino (e.g., diphenylamino, etc.), acyl, acylamino, acyloxy, 5- to 7-membered saturated cyclic amino which may be substituted, 5- to 10-membered aromatic heterocyclic group (e.g., 2- or 3-thienyl, 2-, 3- or 4-pyridyl, 2-, 3-, 4-, 5- or 8-quinolyl, 1-, 3-, 4- or 5-isoquinolyl, 1-, 2- or 3-indolyl, 2-benzothiazolyl, 2-benzo[b]thienyl, benzo[b]furanyl, etc.), sulfo, and so forth.

The "hydrocarbon group" may have 1 to 5, preferably 1 to 3 substituents as mentioned above at possible positions of the hydrocarbon group and, when the number of substituents is two or more, those substituents may be the same as or different from one another.

The above-mentioned "optionally halogenated $C_{1-6}$ alkyl" includes, for example, $C_{1-6}$ alkyl (e.g., methyl, ethyl, propyl, isopropyl, butyl, isobutyl, sec-butyl, tert-butyl, pentyl, hexyl, etc.) which may have 1 to 5, preferably 1 to 3 halogen atoms (e.g., fluoro, chloro, bromo, iodo, etc.). Concretely mentioned is methyl, chloromethyl, difluoromethyl, trichloromethyl, trifluoromethyl, ethyl, 2-bromoethyl, 2,2,2- trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, etc.

The above-mentioned "optionally halogenated $C_{2-6}$ alkenyl" includes, for example, $C_{2-6}$ alkenyl (e.g. vinyl, allyl, isopropenyl, butenyl, isobutenyl, sec-butenyl, etc.) which may have 1 to 5, preferably 1 to 3 halogen atoms (e.g., fluoro, chloro, bromo, iodo, etc.). Concretely mentioned is vinyl, allyl, isopropenyl, butenyl, isobutenyl, sec-butenyl, 3,3,3-trifluoro-1-propenyl, 4,4,4-trifluoro-1-butenyl, etc.

The above-mentioned "optionally halogenated $C_{1-6}$ alkynyl" includes, for example, $C_{1-6}$ alkynyl (e.g., ethynyl, propargyl, butynyl, 1-hexynyl, etc.) which may have 1 to 5, preferably 1 to 3 halogen atoms (e.g., fluoro, chloro, bromo, iodo, etc.). Concretely mentioned is ethynyl, propargyl, butynyl, 1-hexynyl, 3,3,3-trifluoro-1-propynyl, 4,4,4-trifluoro-1-butynyl, etc.

The above-mentioned "optionally halogenated $C_{3-6}$ cycloalkyl" includes, for example, $C_{3-6}$ cycloalkyl (e.g., cyclopropyl, cyclobutyl, cyclopentyl, cyclohexyl, etc.) which may have 1 to 5, preferably 1 to 3 halogen atoms (e.g., fluoro, chloro, bromo, iodo, etc.). Concretely mentioned Is cyclopropyl, cyclobutyl, cyclopentyl, cyclohexyl. 4,4-dichlorocyclohexyl, 2,2,3,3-tetrafluorocyclopentyl, 4-chlorocyclohexyl, etc.

The above-mentioned "optionally halogenated $C_{1-6}$ alkoxy" includes, for example, $C_{1-6}$ alkoxy (e.g., methoxy, ethoxy, propoxy, isopropoxy, butoxy, isobutoxy, sec-butoxy, pentyloxy, hexyloxy, etc.) which may have 1 to 5, preferably 1 to 3 halogen atoms (e.g., fluoro, chloro, bromo, iodo, etc.). Concretely mentioned is methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, etc.

The above-mentioned "optionally halogenated $C_{1-6}$ alkylthio" includes, for example, $C_{1-6}$ alkylthio (e.g., methylthio, ethylthio, propylthio, isopropylthio, butylthio, sec-butylthio, tert-butylthio, etc.) which may have 1 to 5, preferably 1 to 3 halogen atoms (e.g., fluoro, chloro, bromo, iodo, etc.). Concretely mentioned is methylthio, difluoromethylthio, trifluoromethylthio, ethylthio, propylthio, isopropylthio, butylthio, 4,4,4-trifluorobutylthio, pentylthio, hexylthio, etc.

The above-mentioned "acyl" includes, for example, formyl, carboxy, carbamoyl, $C_{1-6}$ alkyl-carbonyl (e.g., acetyl, propionyl, etc.), $C_{3-6}$ cycloalkyl-carbonyl (e.g., cyclopropylcarbonyl, cyclopentylcarbonyl, cyclohexylcarbonyl, etc.), $C_{1-6}$ alkoxy-carbonyl (e.g., methoxycarbonyl, ethoxycarbonyl, propoxycarbonyl, tert-butoxycarbonyl, etc.), $C_{6-10}$ aryl-carbonyl (e.g., benzoyl. 1-naphthoyl, 2-naphthoyl, etc.), $C_{7-16}$ aralkyl-carbonyl (e.g., phenylacetyl, phenylpropionyl, etc.), $C_{6-14}$ aryloxy-carbonyl (e.g., phenoxycarbonyl, etc.), $C_{7-16}$ aralkyloxycarbonyl (e.g., benzyloxycarbonyl, phenethyloxycarbonyl, etc.), 5- or 6-membered heterocycle carbonyl (e.g., nicotinoyl, isonicotinoyl, 2-thenoyl, 3-thenoyl, 2-furoyl, 3-furoyl, morpholinocarbonyl, thiomorpholinocarbonyl, piperidinocarbonyl, 1-pyrrolidinylcarbonyl, etc.), mono-$C_{1-6}$ alkyl-carbamoyl (e.g., methylcarbamoyl, ethylcarbamoyl, etc.), di-$C_{1-6}$ alkyl-carbamoyl (e.g., dimethylcarbamoyl, diethylcarbamoyl, ethylmethylcarbamoyl, etc.), $C_{6-14}$ aryl-carbamoyl (e.g., phenylcarbamoyl, 1-naphthylcarbamoyl, 2-naphthylcarbamoyl, etc.), 5- or 6-membered heterocycle carbamoyl (e.g., 2-pyridylcarbamoyl, 3-pyridylcarbamoyl, 4-pyridylcarbamoyl, 2-thienylcarbamoyl, 3-thienylcarbamoyl, etc.). $C_{1-6}$ alkylsulfonyl (e.g., methylsulfonyl, ethylsulfonyl, etc.), $C_{6-14}$ arylsulfonyl (e.g., phenylsulfonyl, 1-naphthylsulfonyl, 2-naphthylsulfonyl, etc.), $C_{1-6}$ alkylsulfinyl (e.g., methylsulfinyl, ethylsulfinyl, etc.), $C_{6-14}$, arylsulfinyl (e.g., phenylsulfinyl, 1-naphthylsulfinyl, 2-naphthylsulfinyl, etc.), and so forth.

The above-mentioned "acylamino" includes, for example, formylamino, $C_{1-6}$ alkyl-carboxamido (e.g., acetamido, etc.), $C_{6-14}$, aryl-carboxamido (e.g., phenylcarboxamido, naphthylcarboxamido, etc.), $C_{1-6}$ alkoxy-carboxamido (e.g., methoxycarboxamido, ethoxycarboxamido, propoxycarboxamido, butoxycarboxamido, etc.). $C_{1-6}$ alkyl-sulfonylamino (e.g., methylsulfonylamino, ethylsulfonylamino, etc.), $C_{6-14}$ arylsulfonylamino (e.g., phenylsulfonylamino, 2-naphthylsulfonylamino, 1-naphthylsulfonylamino, etc.), and so forth.

The above-mentioned "acyloxy" includes, for example, $C_{1-6}$ alkyl-carbonyloxy (e.g. acetoxy, propionyloxy, etc.), $C_{6-14}$ aryl-carbonyloxy (e.g., benzoyloxy, naphthylcarbonyloxy, etc.), $C_{1-6}$ alkoxy-carbonyloxy (e.g., methoxycarbonyloxy, ethoxycarbonyloxy, propoxycarbonyloxy, butoxycarbonyloxy, etc.), mono-$C_{1-6}$ alkyl-carbamoyloxy (e.g., methylcarbamoyloxy, ethylcarbamoyloxy, etc.), di-$C_{1-6}$ alkyl-carbamoyloxy (e.g., dimethylcarbamoyloxy, diethylcarbamoyloxy, etc.), $C_{6-14}$, aryl-carbamoyloxy (e.g., phenylcarbamoyloxy, naphthylcarbamoyloxy, etc.), nicotinoyloxy, and so forth.

The above-mentioned "5- to 7-membered saturated cyclic amino" of the "5- to 7-membered saturated cyclic amino which may be substituted" includes, for example, morpholino, thiomorpholino, piperazin-1-yl, piperidino, pyrrolidin-1-yl, etc. The "substituents" of the "5- to 7-membered saturated cyclic amino which may be substituted" include, for example, 1 to 3 substituents selected from the group consisting of $C_1$, alkyl (e.g., methyl, ethyl, propyl, isopropyl, butyl, isobutyl, sec-butyl, tert-butyl, pentyl, hexyl, etc.), $C_{6-14}$ aryl (e.g., phenyl, 1-naphthyl, 2-naphthyl, biphenylyl, 2-anthryl, etc.) and 5- to 10-membered aromatic heterocyclic group (e.g., 2- or 3-thienyl, 2-, 3- or 4-pyridyl, 2-, 3-, 4-, 5- or 8-quinolyl, 1-, 3-, 4- or 5-isoquinolyl, 1-, 2- or 3-indolyl, 2-benzothiazolyl, 2-benzo[b]thienyl, benzo[b]furanyl, etc.).

The "3- to 8-membered carbocyclic ring" of the "3- to 8-membered carbocyclic ring which may be substituted" formed by $R^1$ and $R^2$ includes, for example, $C_{3-8}$ cycloalkane such as cyclopropane, cyclobutane, cyclopentane, cyclohexane, etc.

The "3- to 8-membered heterocyclic ring" of the "3- to 8-membered heterocyclic ring which may be substituted" formed by $R^1$ and $R^2$ includes, for example, aziridine, azetidine, morpholine, thiomorpholine, piperazine, piperidine, pyrrolidine, hexamethyleneimine, heptamethyleneimine, hexahydropyrimidine, etc.

The "substituents" of the "3- to 8-membered carbo or heterocyclic ring which may be substituted" formed by $R^1$ and $R^2$ include, for example, 1 to 3 substituents selected from the group consisting of $C_{1-6}$ alkyl (e.g., methyl, ethyl, propyl, isopropyl, butyl, isobutyl, sec-butyl, tert-butyl, pentyl, hexyl, etc.), $C_{6-14}$ aryl (e.g., phenyl, 1-naphthyl, 2-naphthyl, biphenylyl, 2-anthryl, etc.), $C_{7-16}$ aryl (e.g., benzyl, phenethyl, diphenylmethyl, 1-naphthylmethyl, 2-naphthylmethyl, 2,2-diphenylethyl, etc.), amino, mono-$C_{1-6}$ alkylamino (e.g., methylamino, ethylamino, etc.), mono-$C_{6-14}$ arylamino (e.g., phenylamino, 1-naphthylamino, 2-naphthylamino, etc.), di-$C_{1-6}$ alkylamino (e.g., dimethylamino, diethylamino, etc.), di-$C_{6-14}$ arylamino (e.g., diphenylamino, etc.) and 5- to 10-membered aromatic heterocyclic group (e.g., 2- or 3-thienyl, 2-, 3- or 4-pyridyl, 2-, 3-, 4-, 5- or 8-quinolyl, 1-, 3-, 4- or 5-isoquinolyl, 1-, 2- or 3-indolyl, 2-benzothiazolyl, 2-benzo[b]thienyl, benzo[b]furanyl, etc.).

The "lower alkyl" of the "lower alkyl which may be substituted" for R includes, for example, $C_{1-6}$ alkyl such as methyl, ethyl, propyl, isopropyl, butyl, isobutyl, sec-butyl, tert-butyl, pentyl, hexyl, etc.

The "substituents" of the "lower alkyl which may be substituted" for $R^3$ and their number are the same as those mentioned above for the "substituents" of the "hydrocarbon group which may be substituted" for $R^1$ or $R^2$.

The "aromatic group" of the "aromatic group which may be substituted" for $R^3$ includes, for example, an aromatic hydrocarbon group, an aromatic heterocyclic group, and so forth.

The "aromatic hydrocarbon group" includes, for example, a $C_{6-14}$ monocyclic or fused polycyclic (e.g., bi- or tricyclic) aromatic hydrocarbon group, etc. Concretely mentioned is $C_{6-14}$, aryl such as phenyl, 1-naphthyl, 2-naphthyl, biphenylyl, 2-anthryl, etc.

The "aromatic heterocyclic group" includes, for example, 5- to 14-membered, preferably 5- to 10-membered aromatic heterocyclic group containing one or more (e.g., 1 to 4) hetero atoms selected from the group consisting of nitrogen, sulfur and oxygen atoms in addition to carbon atoms, etc. Concretely mentioned is a monovalent group formed by removing an optional hydrogen atom from an aromatic heterocyclic ring such as thiophene, benzothiophene, benzofuran, benzimidazole, benzoxazole, benzothiazole, benzisothiazole, naphtho[2,3-b]thiophene, furan, isoindolidine, xanthrene, phenoxathiin, pyrrole, imidazole, pyrazole, pyridine, pyrazine, pyrimidine, pyridazine, indole, isoindole, 1H-indazole, purine, 4H-quinolizine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, oxazole, isoxazole, furazan, phenoxazine, etc.; or a ring as formed through condensation of the above aromatic heterocyclic ring, preferably monocyclic ring, with one or more, preferably one or two aromatic rings (e.g., benzene ring, etc.), etc.

The preferred example of the "aromatic heterocyclic group" is a 5- or 6-membered aromatic heterocyclic group which may be fused with one benzene ring. Concretely mentioned is 2-, 3- or 4-pyridyl, 2-, 3-, 4-, 5- or 8-quinolyl, 1-, 3-, 4- or 5-isoquinolyl, 1-, 2- or 3-indolyl, 2-benzothiazolyl, 2-benzo[b]thienyl, benzo[b]furanyl, 2- or 3-thienyl, etc. More preferred is 2- or 3-thienyl, 2-, 3- or 4-pyridyl, 2- or 3-quinolyl, 1-isoquinolyl, 1- or 2-indolyl, 2-benzothiazolyl, etc.

The "substituents" of the "aromatic heterocyclic group which may be substituted" include, for example, halogen atoms (e.g., fluoro, chloro, bromo, iodo, etc.), $C_{1-3}$ alkylenedioxy (e.g., methylenedioxy, ethylenedioxy, etc.), nitro, cyano, optionally halogenated $C_{1-6}$ alkyl, optionally halogenated $C_{1-6}$ alkenyl, optionally halogenated $C_{2-6}$ alkynyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino (e.g., methylamino, ethylamino, propylamino, isopropylamino, butylamino, etc.), di-$C_{1-6}$ alkylamino (e.g., dimethylamino, diethylamino, dipropylamino, dibutylamino, ethylmethylamino, etc.), 5- to 7-membered saturated cyclic amino which may be substituted, acyl, acylamino, acyloxy, sulfo, $C_{6-14}$ aryl (e.g., phenyl, 1-naphthyl, 2-naphthyl, etc.), $C_{6-14}$ aryloxy (e.g., phenyloxy, naphthyloxy, etc.), and so forth.

The "aromatic group" may have 1 to 3 substituents as mentioned above at possible positions of the aromatic group and, when the number of substituents is two or more, those substituents may be the same as or different from one another.

The above-mentioned "optionally halogenated $C_{1-6}$ alkyl", "optionally halogenated $C_{2-6}$ alkenyl", "optionally halogenated $C_{2-6}$ alkynyl", "optionally halogenated $C_{1-6}$ cycloalkyl", "optionally halogenated $C_{1-6}$ alkoxy", "optionally halogenated $C_{1-6}$ alkylthio", "5- to 7-membered saturated cyclic amino which may be substituted", "acyl", "acylamino" and "acyloxy" include, for example, those described in detail in the foregoing referring to the "substituents" of the "hydrocarbon group which may be substituted" for $R^1$ or $R^2$, respectively.

A preferred example of the "aromatic group which may be substituted" for R' is a phenyl, 2-, 3- or 4-pyridyl, 2- or 3-quinolyl or 1-isoquinolyl group, each of which may be substituted by 1 to 3 substituents selected from the group consisting of halogen atoms, $C_{1-3}$ alkylenedioxy, nitro, cyano, optionally halogenated $C_{1-6}$ alkyl, optionally halogenated $C_{2-6}$ alkenyl, optionally halogenated $C_{2-6}$ alkynyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, 5- to 7-membered saturated cyclic amino which may be substituted, acyl, acylamino, acyloxy, sulfo, $C_{6-14}$ aryl and $C_{6-14}$ aryloxy.

The "aromatic group which may be substituted" for $R^4$ includes, for example, 1 to 3, preferably 1 or 2 of the "aromatic group which may be substituted" for R' above mentioned.

The "aliphatic hydrocarbon group" of the "aliphatic hydrocarbon group substituted by an aromatic group which may be substituted, which hydrocarbon group may be further substituted" for $R^4$ includes, for example, alkyl, alkenyl, alkynyl, cycloalkyl, and so forth. Among others, preferred are $C_{1-10}$ alkyl, $C_{2-10}$ alkenyl, $C_{2-10}$ alkynyl and $C_{3-10}$ cycloalkyl.

The "alkyl" is preferably, for example, $C_{1-6}$ alkyl such as methyl, ethyl, propyl, isopropyl, butyl, isobutyl, sec-butyl, tert-butyl, pentyl, hexyl, etc.

The "alkenyl" is preferably, for example, $C_{2-6}$ alkenyl such as vinyl, allyl, isopropenyl, butenyl, isobutenyl, sec-butenyl, etc.

The "alkynyl" is preferably, for example, $C_{2-6}$ alkynyl such as ethynyl, propargyl, butynyl, 1-hexynyl, etc.

The "cycloalkyl" is preferably, for example, $C_{3-6}$ cycloalkyl such as cyclopropyl, cyclobutyl, cyclopentyl, cyclohexyl, etc.

Among others, preferred is $C_{1-6}$ alkyl.

The "aromatic group which may be substituted" which the above "aliphatic hydrocarbon group" have, includes, for example, 1 to 3 of the "aromatic group which may be substituted" for $R^3$.

A Preferred example of the above "aromatic group which may be substituted" is a phenyl, 2-, 3- or 4-pyridyl, 2- or 3-quinolyl or 1-isoquinolyl group, each of which may be substituted by 1 to 3 substituents selected from the group consisting of halogen atoms, $C_{1-3}$ alkylenedioxy, nitro, cyano, optionally halogenated $C_{1-6}$ alkyl, optionally halogenated $C_{1-6}$ alkenyl, optionally halogenated $C_{2-6}$ alkynyl, optionally halogenated $C_{1-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, 5- to 7-membered saturated cyclic amino which may be substituted, acyl, acylamino, acyloxy, sulfo, $C_{6-14}$ aryl and $C_{6-14}$, aryloxy.

The "substituents" which the above "aliphatic hydrocarbon group" may further have, and their number are the same as those mentioned above for the "substituents" of the "hydrocarbon group which may be substituted" for $R^1$ or $R^2$.

Among them, preferred are acyl such as carboxy, $C_{1-6}$ alkyl-carbonyl, $C_{1-6}$ alkoxy-carbonyl, $C_{6-14}$ aryl-carbonyl, etc.

The "acyl" for $R^4$ includes, for example, an acyl of the formula: —(C=O)—$R^5$, —(C=O)—$OR^5$, —(C=O)—$NR^5R^6$, —(C=S)—$NHR^5$, —$SO_2$—$R^{5a}$ or —SO—$R^5$ wherein R' is a hydrogen atom, an aromatic group which may be substituted or an aliphatic hydrocarbon group which may be substituted; $R^{5a}$ is an aromatic group which may be substituted or an aliphatic hydrocarbon group which may be substituted; and $R^6$ is a hydrogen atom or $C_{1-6}$ alkyl.

The "aromatic group which may be substituted" for $R^5$ or $R^{5a}$ includes, for example, the "aromatic group which may be substituted" for $R^3$ above.

The "aliphatic hydrocarbon group" of the "aliphatic hydrocarbon group which may be substituted" for $R^5$ or $R^{5a}$ includes, for example, the "aliphatic hydrocarbon group" of the "aliphatic hydrocarbon group substituted by an aromatic group which may be substituted, which hydrocarbon group may be further substituted" for $R^4$ above.

The "substituents" of the "aliphatic hydrocarbon group which may be substituted" for $R^5$ or $R^{5a}$ include, for example, (1) the "aromatic group which may be substituted" of the "aliphatic hydrocarbon group substituted by an aromatic group which may be substituted, which hydrocarbon group may be further substituted" for $R^4$ above, (2) halogen atoms (e.g., fluoro, chloro, bromo, iodo, etc.), (3) $C_{1-3}$ alkylenedioxy (e.g., methylenedioxy, ethylenedioxy, etc.), (4) nitro, (5) cyano, (6) optionally halogenated $C_{1-6}$ alkyl, (7) optionally halogenated $C_{2-6}$ alkenyl, (8) optionally halogenated $C_{2-6}$ alkynyl, (9) optionally halogenated $C_{1-6}$ cycloalkyl, (10) optionally halogenated $C_{1-6}$ alkoxy, (11) optionally halogenated $C_{1-6}$ alkylthio, (12) hydroxy, (13) amino, (14) mono-$C_{1-6}$ alkylamino (e.g., methylamino, ethylamino, etc.), (15) di-$C_{1-6}$ alkylamino (e.g., dimethylamino, diethylamino, etc.), (16) 5- to 7-membered saturated cyclic amino which may be substituted, (17) acyl, (18) acylamino, (19) acyloxy, (20) sulfo, and so forth.

The above-mentioned "optionally halogenated $C_{1-6}$ alkyl", "optionally halogenated $C_{2-6}$ alkenyl", "optionally halogenated $C_2$ alkynyl", "optionally halogenated $C_{3-6}$ cycloalkyl", "optionally halogenated $C_{1-6}$ alkoxy", "optionally halogenated $C_{1-6}$ alkylthio", "5- to 7-membered saturated cyclic amino which may be substituted", "acyl", "acylamino" and "acyloxy" include, for example, those described in detail in the foregoing referring to the "substituents" of the "hydrocarbon group which may be substituted" for $R^1$ or $R^2$, respectively.

The "aliphatic hydrocarbon group" may have 1 to 5, preferably 1 to 3 substituents as mentioned above at possible positions of the aliphatic hydrocarbon group and, when the number of substituents is two or more, those substituents may be the same as or different from one another.

Preferably, $R^5$ and $R^{5a}$ each is an aromatic group which may be substituted.

The "$C_{1-6}$ alkyl" for $R^6$ includes, for example, methyl, ethyl, propyl, isopropyl, butyl, isobutyl, sec-butyl, tert-butyl, pentyl, hexyl, etc.

The "sulfur atom which may be oxidized" for X or Y includes S, SO and $SO_2$.

The "substituents" which ring A may have apart from the group of the formula: —X—$R^4$, include, for example, the "substituents" of the "aromatic group which may be substituted" for $R^3$ above. Ring A may have 1 to 3 substituents as mentioned above at possible positions of the ring and, when the number of substituents is two or more, those substituents may be the same as or different from one another.

Preferably, the "substituents" which ring A may have apart from the group of the formula: —X—$R^4$, include, for example, halogen atoms, $C_{1-3}$ alkylenedioxy, nitro, cyano, optionally halogenated $C_{1-6}$ alkyl, optionally halogenated $C_{2-6}$ alkenyl, optionally halogenated $C_{1-6}$ alkynyl, optionally halogenated $C_{3-6}$ cycloalkyl, optionally halogenated $C_{1-6}$ alkoxy, optionally halogenated $C_{1-6}$ alkylthio, hydroxy, acyl, acyloxy, sulfo, $C_{6-14}$ aryl, $C_{6-14}$ aryloxy, and so forth.

The "aromatic group which may be substituted" and the "acyl" for $R^{4a}$ include, for example, the "aromatic group which may be substituted" and the "acyl" for $R^4$, respectively.

The "aliphatic hydrocarbon group which may be substituted" for $R^{4a}$ includes, for example, the "aliphatic hydrocarbon group which may be substituted" for $R^5$ or $R^{5a}$.

The "sulfur atom which may be oxidized" for Xa or Ya is same as the "sulfur atom which may be oxidized" for X above.

The "substituents" of the "imino which may be substituted" for Ya includes, for example, a hydrocarbon group which may be substituted, an acyl, and so forth.

The above "hydrocarbon group which may be substituted" includes, for example, the "hydrocarbon group which may be substituted" for $R^2$ or $R^2$.

The above "acyl" includes, for example, that described in detail in the foregoing referring to the "substituents" of the "hydrocarbon group which may be substituted" for $R^1$ or $R^2$.

The preferred examples of the "imino which may be substituted" for Ya includes imino, $C_{1-6}$ alkylimino (e.g., methylimino, ethylimino, etc.), $C_{6-14}$ arylimino (e.g., phenylimino, 1-naphthylimino, 2-naphthylimino, etc.), $C_{7-16}$ aralkylimino (e.g., benzylimino, etc.), etc.

The "substituents" which ring Aa may have apart from the group of the formula: —Xa-$R^{4a}$, include any substituent apart from an amino which may be substituted, for example, halogen atoms (e.g., fluoro, chloro, bromo, iodo, etc.), $C_{1-6}$ alkylenedioxy (e.g., methylenedioxy, ethylenedioxy, etc.), nitro, cyano, optionally halogenated $C_{1-6}$ alkyl, optionally halogenated $C_{2-6}$ alkenyl, optionally halogenated $C_{2-6}$ alkynyl, optionally halogenated $C_{3-6}$ cycloalkyl, optionally halogenated $C_{1-6}$ alkoxy, optionally halogenated $C_{1-6}$ alkylthio, hydroxy, acyl, acyloxy, sulfo, and so forth.

The above-mentioned "optionally halogenated $C_{1-6}$ alkyl", "optionally halogenated $C_{2-6}$ alkenyl", "optionally halogenated $C_{2-6}$ alkynyl", "optionally halogenated $C_{3-6}$ cycloalkyl", "optionally halogenated $C_{1-6}$ alkoxy", "optionally halogenated $C_{1-6}$ alkylthio", "acyl" and "acyloxy" include, for example, those described in detail in the foregoing referring to the "substituents" of the "hydrocarbon group which may be substituted" for $R^1$ or $R^2$, respectively.

Ring Aa may have 1 to 3 substituents as mentioned above at possible positions of the ring and, when the number of substituents is two or more, those substituents may be the same as or different from one another.

In the above formulae, preferably, $R^1$ and $R^2$ each is a $C_{1-6}$ alkyl which may be substituted, or $R^1$ and $R^2$ form, taken together with the adjacent carbon atom, a 3- to 8-membered carbo or heterocyclic ring which may be substituted.

Preferably, $R^3$ is an aromatic group which may be substituted.

Preferably, $R^4$ and $R^{4a}$ each is (1) an aliphatic hydrocarbon group substituted by an aromatic group which may be substituted, which hydrocarbon group may be further substituted or (2) an acyl.

Preferably, X and Xa each is an oxygen atom.
Preferably, Y and Ya each is an oxygen atom.
The group of the formula: —X—R⁴ is preferably substituted on the 5-position of the basic skeleton as follows.

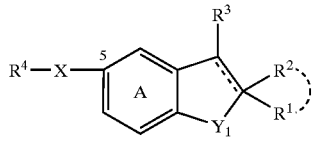

The group of the formula: —Xa-R⁴ᵃ is preferably substituted on the 5-position of the basic skeleton as follows.

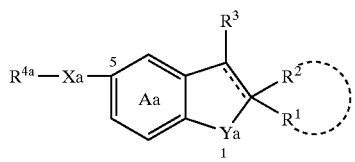

In compound (I), preferred is a compound wherein R¹ and R² each is a $C_{1-6}$ alkyl which may be substituted by 1 to 3 substituents selected from the group consisting of (1) $C_{6-14}$ aryl, (2) $C_{1-6}$ alkoxy, (3) $C_{1-6}$ alkylthio, (4) hydroxy, (5) amino, (6) mono-$C_{1-6}$ alkylamino, (7) mono-$C_{6-14}$ arylamino, (8) di-$C_{1-6}$ alkylamino, (9) di-$C_{6-14}$ arylamino, (10) carboxy, (11) $C_{1-6}$ alkylsulfonyl, (12) $C_{6-14}$ arylsulfonyl, (13) $C_{1-6}$ alkylsulfinyl, (14) $C_{6-4}$ arylsulfinyl and (15) 5- to 7-membered saturated cyclic amino which may be substituted by 1 to 3 substituents selected from the group consisting of $C_{1-6}$ alkyl, $C_{6-14}$ aryl and 5- to 10-membered aromatic group, or R¹ and R² form, taken together with the adjacent carbon atom, a 3- to 8-membered carbo or heterocyclic ring which may be substituted by 1 to 3 substituents selected from the group consisting of $C_{1-6}$ alkyl, $C_{6-14}$ aryl, $C_{7-16}$ aralkyl and 5- to 10-membered aromatic heterocyclic group;

R³ is a phenyl, 1-naphthyl, 2-naphthyl, 2-thienyl, 3-thienyl, 2-pyridyl, 3-pyridyl, 4-pyridyl, 2-quinolyl, 3-quinolyl, 1-isoquinolyl, 1-indolyl, 2-indolyl or 2-benzothiazolyl group, each of which may be substituted by 1 to 3 substituents selected from the group consisting of (1) halogen atoms, (2) $C_{1-6}$ alkyl, (3) $C_{1-6}$ alkoxy, (4) mono-$C_{1-6}$ alkylamino, (5) di-$C_{1-6}$ alkylamino and (6) 5- to 7-membered saturated cyclic amino which may be substituted by 1 to 3 substituents selected from the group consisting of $C_{1-6}$ alkyl, $C_{6-14}$ aryl and 5- to 10-membered aromatic group;

R⁴ is (i) $C_{1-6}$ alkyl substituted by a phenyl, 1-naphthyl, 2-naphthyl, 2-thienyl, 3-thienyl, 2-pyridyl, 3-pyridyl, 4-pyridyl, 2-quinolyl, 3-quinolyl, 1-isoquinolyl, 1-indolyl, 2-indolyl or 2-benzothiazolyl group, each of which may be substituted by 1 to 3 substituents selected from the group consisting of (1) halogen atoms, (2) $C_{1-6}$ alkyl, (3) $C_{1-6}$ alkoxy, (4) hydroxy, (5) amino, (6) mono-$C_{1-6}$ alkylamino, (7) di-$C_{1-6}$ alkylamino, (8) carboxy and (9) 5- to 7-membered saturated cyclic amino which may be substituted by 1 to 3 substituents selected from the group consisting of $C_{1-6}$ alkyl, $C_{6-14}$ aryl and 5- to 10-membered aromatic group, which $C_{1-6}$ alkyl may be further substituted by carboxy or $C_{1-6}$ alkoxy-carbonyl, or (ii) a $C_{1-6}$ alkyl-carbonyl, $C_{3-6}$ cycloalkyl-carbonyl, $C_{6-14}$ aryl-carbonyl or $C_{7-16}$ aralkyl-carbonyl group, each of which may be substituted by 1 to 3 substituents selected from the group consisting of halogen atoms, $C_{1-6}$ alkyl, $C_{1-6}$ alkoxy, hydroxy, amino, mono-$C_{1-6}$ alkylamino, di-$C_{1-6}$ alkylamino and carboxy;

X is an oxygen atom;

Y is an oxygen atom; and ring A is a benzene ring which may be further substituted by 1 to 3 substituents selected from the group consisting of halogen atoms, optionally halogenated $C_{1-6}$ alkyl, optionally halogenated $C_{1-6}$ alkoxy, amino, mono-$C_{1-6}$ alkylamino and di-$C_{1-6}$ alkylamino.

More preferred is a compound wherein R¹ and R² each is a $C_{1-6}$ alkyl which may be substituted by 1 to 3 substituents selected from the group consisting of $C_{6-14}$ aryl, $C_{1-6}$ alkoxy, $C_{1-6}$ alkylthio, hydroxy, amino, mono-$C_{1-6}$ alkylamino, mono-$C_{6-14}$ arylamino, di-$C_{1-6}$ alkylamino, di-$C_{6-14}$ arylamino, carboxy, $C_{1-6}$ alkylsulfonyl, $C_{6-14}$ arylsulfonyl, $C_{1-6}$ alkylsulfinyl and $C_{6-14}$, arylsulfinyl, or R¹ and R² form, taken together with the adjacent carbon atom, a piperidine which may be substituted by 1 to 3 substituents selected from group consisting of $C_{1-6}$ alkyl, $C_{6-14}$ aryl and $C_{7-16}$ aralkyl;

R³ is a phenyl which may be substituted by 1 to 3 substituents selected from the group consisting of halogen atoms, $C_{1-6}$ alkyl, $C_{1-6}$ alkoxy, amino, mono-$C_{1-6}$ alkylamino and di-$C_{1-6}$ alkylamino;

R⁴ is (i) $C_{1-6}$ alkyl substituted by a phenyl or pyridyl, each of which may be substituted by 1 to 3 substituents selected from the group consisting of halogen atoms, $C_{1-6}$ alkyl, $C_{1-6}$ alkoxy, hydroxy, amino, mono-$C_{1-6}$ alkylamino, di-$C_{1-6}$ alkylamino and carboxy, or (ii) an acyl of the formula: —(C=O)—R⁵' wherein R⁵' is a phenyl or phenyl-$C_{1-6}$ alkyl, each of which may be substituted by 1 to 3 substituents selected from the group consisting of halogen atoms, $C_{1-6}$ alkyl, $C_{1-6}$ $C_{1-6}$ alkoxy, hydroxy, amino, mono-$C_{1-6}$ alkylamino, di-$C_{1-6}$ alkylamino and carboxy;

X is an oxygen atom;

Y is an oxygen atom; and ring A is a benzene ring which may be further substituted by 1 to 3 substituents selected from the group consisting of halogen atoms, optionally halogenated $C_{1-6}$ alkyl, optionally halogenated $C_{1-6}$ alkoxy, amino, mono-$C_{1-6}$ alkylamino and di-$C_{1-6}$ alkylamino.

Furthermore the compound of the following formula is also preferred.

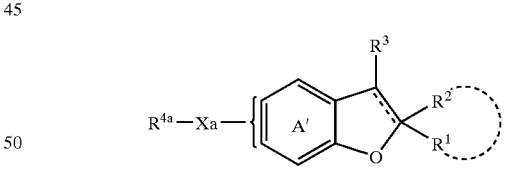

wherein R¹ and R² each is $C_{1-6}$ alkyl which may be substituted by 6-membered saturated cyclic amino substituted by a phenyl, or R¹ and R² form, taken together with the adjacent carbon atom, a piperidine substituted by a $C_{1-6}$ alkyl or a $C_{7-16}$ aralkyl;

R³ is (i) a hydrogen atom, or (ii) a phenyl which may be substituted by 1 to 3 substituents selected from the group consisting of (1) $C_{1-4}$ alkyl, (2) di-$C_{1-6}$ alkylamino and (3) 6-membered saturated cyclic amino which may be substituted by a $C_{1-6}$ alkyl, R⁴ is (i) a phenyl which may be substituted by 1 to 3 substituents selected from the group consisting of nitro and $C_{1-6}$ alkyl-carboxamido, (ii) a $C_{1-6}$ alkyl or $C_{2-6}$ alkenyl group substituted by 1 to 3 of phenyl, quinolyl or pyridyl, each of which may be substituted by 1 to 3 substituents selected from the group consisting of $C_{1-6}$ alkoxy, $C_{1-6}$ alkylthio, $C_{1-6}$ alkoxy-carbonyl, $C_{1-6}$ alkylsulfonyl and $C_{1-6}$ alkylsulfinyl, which $C_{1-6}$ alkyl or $C_{2-6}$ alkenyl group may be further substituted by a phenyl, carboxy or $C_{1-6}$ alkoxy-carbonyl, or (iii) an acyl of the formula: —(C=O)—$R^{5''}$ wherein $R^{5''}$ is phenyl substituted by a $C_{1-6}$ alkoxy; and ring A' is a benzene ring which may be further substituted by 1 to 3 $C_{1-6}$ alkyl.

In compound (Ia), preferred is a compound wherein $R^1$ and $R^2$ each is a $C_{1-6}$ alkyl which may be substituted by 1 to 3 substituents selected from the group consisting of (1) $C_{6-14}$ aryl, (2) $C_{1-6}$ alkoxy, (3) $C_{1-6}$ alkylthio, (4) hydroxy, (5)-amino, (6) mono-$C_{1-6}$ alkylamino, (7) mono-$C_{1-6}$ arylamino, (8) di-$C_{1-6}$ alkylamino, (9) di-$C_{6-14}$ arylamino, (10) carboxy, (11) $C_{1-6}$ alkylsulfonyl, (12) $C_6S_{14}$ arylsulfonyl, (13) $_{1-6}$ alkylsulfinyl, (14) $C_{6-14}$ arylsulfinyl and (15) 5- to 7-membered saturated cyclic amino which may be substituted by 1 to 3 substituents selected from the group consisting of $C_{1-6}$ alkyl, $C_{6-14}$ aryl and 5- to 10-membered aromatic group, or $R^1$ and $R^2$ form, taken together with the adjacent carbon atom, a 3- to 8-membered carbo or heterocyclic ring which may be substituted by 1 to 3 substituents selected form the group consisting of $C_{1-6}$ alkyl, $C_{6-14}$ aryl, $C_{7-16}$ aralkyl and 5- to 10-membered aromatic heterocyclic group;

$R^3$ is a phenyl, 1-naphthyl, 2-naphthyl, 2-thienyl, 3-thienyl, 2-pyridyl, 3-pyridyl, 4-pyridyl, 2-quinolyl, 3-quinolyl, 1-isoquinolyl, 1-indolyl, 2-indolyl or 2-benzothiazolyl group, each of which may be substituted by 1 to 3 substituents selected from the group consisting of (1) halogen atoms, (2) $C_{1-6}$ alkyl, (3) $C_{1-6}$ alkoxy, (4) mono-$C_{1-6}$ alkylamino, (5) di-$C_{1-6}$ alkylamino and (6) 5- to 7-membered saturated cyclic amino which may be substituted by 1 to 3 substituents selected from the group consisting of $C_{1-6}$ alkyl, $C_{6-14}$ aryl and 5- to 10-membered aromatic group;

$R^{4a}$ is (i) $C_{1-6}$ alkyl substituted by a phenyl, 1-naphthyl, 2-naphthyl, 2-thienyl, 3-thienyl, 2-pyridyl, 3-pyridyl, 4-pyridyl, 2-quinolyl, 3-quinolyl, 1-isoquinolyl, 1-indolyl, 2-indolyl or 2-benzothiazolyl group, each of which may be substituted by 1 to 3 substituents selected from the group consisting of (1) halogen atoms, (2) $C_{1-6}$ alkyl, (3) $C_{1-6}$ alkoxy, (4) hydroxy, (5) amino, (6) mono-$C_{1-6}$ alkylamino, (7) di-$C_{1-6}$ alkylamino, (8) carboxy and (9) 5- to 7-membered saturated cyclic amino which may be substituted by 1 to 3 substituents selected the group consisting of $C_{1-6}$ alkyl, $C_{6-14}$ aryl and 5- to 10-membered aromatic group, which $C_{1-6}$ alkyl may be further substituted by carboxy or $C_{1-6}$ alkoxy-carbonyl, or (ii) a $C_{1-6}$ alkyl-carbonyl, $C_{3-6}$ cycloalkyl-carbonyl, $C_{6-14}$ aryl-carbonyl or $C_{1-6}$ aralkyl-carbonyl group, each of which may be substituted by 1 to 3 substituents selected from the group consisting of halogen atoms, $C_{1-6}$ alkyl, $C_{1-6}$ alkoxy, hydroxy, amino, mono-$C_{1-6}$ alkylamino, di-$C_{1-6}$ alkylamino and carboxy; Xa is an oxygen atom;

Ya is an oxygen atom; and ring Aa is a benzene ring which may be further substituted by 1 to 3 substituents selected from the group consisting of halogen atoms, optionally halogenated $C_{1-6}$ alkyl and optionally halogenated $C_{1-6}$ alkoxy.

More preferred is a compound wherein $R^1$ and $R^2$ each is a $C_{1-6}$ alkyl which may be substituted by 1 to 3 substituents selected from the group consisting of $C_{6-14}$ aryl, $C_{1-6}$ alkoxy, $C_{1-6}$ alkylthio, hydroxy, amino, mono-$C_{1-6}$ alkylamino, mono-$C_{6-14}$ arylamino, di-$C_{1-6}$ alkylamino, di-$C_{6-14}$ arylamino, carboxy, $C_{1-6}$ alkylsulfonyl, $C_{6-14}$ arylsulfonyl, $C_{1-6}$ alkylsulfinyl and $C_{6-14}$ arylsulfinyl, or $R^1$ and $R^2$ form, taken together with the adjacent carbon atom, a piperidine which may be substituted by 1 to 3 substituents selected from the group consisting of $C_{1-6}$ alkyl, $C_{6-14}$ aryl and $C_{7-16}$ aralkyl;

$R^3$ is a phenyl which may be substituted by 1 to 3 substituents selected from the group consisting of halogen atoms, $C_{1-6}$ alkyl, $C_{1-6}$ alkoxy, amino, mono-$C_{1-6}$ alkylamino and di-$C_{1-6}$ alkylamino;

$R^{4a}$ is (i) $C_{1-6}$ alkyl substituted by a phenyl or pyridyl, each of which may be substituted by 1 to 3 substituents selected from the group consisting of halogen atoms, $C_{1-6}$ alkyl, $C_{1-6}$ alkoxy, hydroxy, amino, mono-$C_{1-6}$ alkylamino, di-$C_{1-6}$ alkylamino and carboxy, or (ii) an acyl of the formula: —(C=O)—$R^{5'}$ wherein $R^{5'}$ is a phenyl or phenyl-$C_{1-6}$ alkyl, each of which may be substituted by 1 to 3 substituents selected from the group consisting of halogen atoms, $C_{1-6}$ alkyl, $C_{1-6}$ alkoxy, hydroxy, amino, mono-$C_{1-6}$ alkylamino, di-$C_{1-6}$ alkylamino and carboxy;

Xa is an oxygen atom;

Ya is an oxygen atom; and ring Aa is a benzene ring which may be further substituted by 1 to 3 substituents selected from the group consisting of halogen atoms, optionally halogenated $C_{1-6}$ alkyl and optionally halogenated $C_{1-6}$ alkoxy.

As compound (I) or (Ia), concretely mentioned are 3-(4-isopropylphenyl)-5-(4-methoxybenzyloxy)-2,2,4,6,7-pentamethyl-2,3-dihydrobenzofuran, 3-(4-isopropylphenyl)-2,4,6,7-tetramethylbenzofuran-5-yl 4-methoxybenzoate, 3-(4-isopropylphenyl)-5-(4-methoxybenzyloxy)-2,4,6,7-tetramethylbenzofuran, 3-(4-isopropylphenyl)-5-(4-methoxybenzyloxy)-1',4,6,7-tetramethylspiro[benzofuran-2(3H),4'-piperidine], 3-(4-isopropylphenyl)-5-(3-pyridylmethyl)-2,2,4,6,7-pentamethyl-2,3-dihydrobenzofuran, and salts thereof.

More Preferred examples are 3-(4-isopropylphenyl)-5-(4-methoxybenzyloxy)-2,2,4,6,7-pentamethyl-2,3-dihydrobenzofuran, 3-(4-isopropylphenyl)-2,4,6,7-tetramethylbenzofuran-5-yl 4-methoxybenzoate, 3-(4-isopropylphenyl)-5-(4-methoxybenzyloxy)-2,4,6,7-tetramethylbenzofuran, 3-(4-isopropylphenyl)-5-(4-methoxybenzyloxy)-1',4,6,7-tetramethylspiro[benzofuran-2(3H),4'-piperidine], and salts thereof.

Salts of compound (I) or compound (Ia) include, for example, metal salts, ammonium salts, salts with organic bases, salts with inorganic acids, salts with organic acids, salts with basic or acidic amino acids, etc. Preferred examples of metal salts include alkali metal salts such as sodium salts, potassium salts; alkaline earth metal salts such as calcium salts, magnesium salts, barium salts; aluminium salts, etc. Preferred examples of salts with organic bases include salts with trimethylamine, triethylamine, pyridine, picoline, ethanolamine, diethanolamine, triethanolamine, dicyclohexylamine, N,N-dibenzylethylenediamine, etc. Preferred examples of salts with inorganic acids include hydrochlorides, hydrobromides, nitrates, sulfates, phosphates, etc. Preferred examples of salts with organic acids include formates, acetates, trifluoroacetates, fumarates, oxalates, tartrates, maleates, citrates, succinates, malates, methanesulfonates, benzenesulfonates, p-toluenesulfonates, etc. Preferred examples of salts with basic amino acids include salts with arginine, lysine, ornithine, etc. Preferred examples of salts with acidic amino acids include aspartates, glutamates, etc.

Among others, more preferred are pharmaceutically acceptable salts. For example, for compound (I) or (Ia) having an acidic functional group in the molecule, mentioned are their inorganic salts, such as alkali metal salts (e.g., sodium salts, potassium salts, etc.), and alkaline earth metal salts (e.g., calcium salts, magnesium salts, barium salts, etc.), ammonium salts, etc.; and for compound (I) or (Ia) having a basic functional group in the molecule, mentioned are their inorganic salts such as hydrochlorides, sulfates, phosphates, hydrobromides etc., and organic salts such as acetates, maleates, fumarates, succinates, methanesulfonates, p-toluenesulfonates, citrates, tartrates, etc.

Process for producing compound (I) and compound (Ia) is mentioned below.

Compound (I) of the present invention can be produced in any per se known manner, for example, according to the methods disclosed in EP-A-273647, JP-A-1-272578, EP-A-483772, JP-A-5-140142, EP-A-345593, JP-A-2-76869, EP-A-345592 and JP-A-2-76870, or analogous methods thereto, as well as according to the methods of the following process. Compound (Ia) can be produced in the same manner as in the production of compound (I), or in any other per se known manner, for example, according to the methods disclosed in WO 94/14434, JP-A-8-504826 and WO 84/02131, or analogous methods thereto.

Each symbol in the compounds in the following process is same as defined above. Compounds (II) and (III) described in the following process include their salts. For their salts, for example, referred to are the same as the salts of compound (I).

Process 1

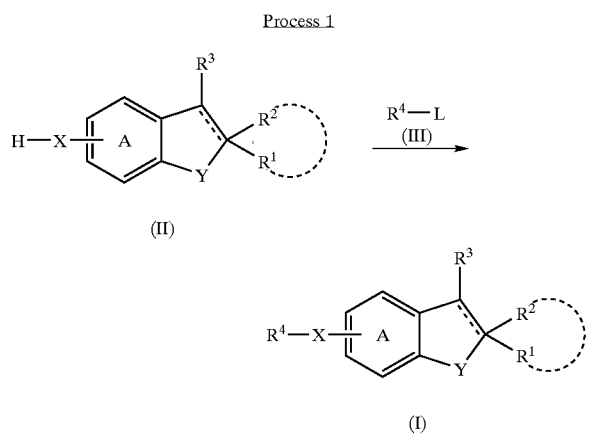

Compound (I) is produced by reacting compound (II) with a compound of the formula: $R^4$-L wherein L represents a leaving group and $R^4$ is as defined above [compound (III)].

The "leaving group" for L includes, for example, hydroxy, halogen atoms (e.g., fluoro, chloro, bromo, iodo, etc.), optionally halogenated $C_{1-5}$ alkylsulfonyloxy (e.g., methanesulfonyloxy, ethanesulfonyloxy, trichloromethanesulfonyloxy, etc.), $C_{6-10}$ arylsulfonyloxy which may be substituted. The "$C_{6-10}$ arylsulfonyloxy which may be substituted" includes, for example, $C_{6-10}$ arylsulfonyloxy (e.g. phenylsulfonyloxy, naphthylsulfonyloxy, etc.) which may be substituted by 1 to 3 substituents selected from the group consisting of $C_{1-6}$ alkyl, $C_{1-6}$ alkoxy and nitro. Concretely mentioned is benzenesulfonyloxy, m-nitrobenzenesulfonyloxy and p-toluenesulfonyloxy, and so forth.

(1) Hereinunder mentioned is the case where $R^4$ is "an aromatic group which may be substituted" or "an aliphatic hydrocarbon group substituted by an aromatic group which may be substituted, which hydrocarbon group may be further substituted".

Compound (II) is reacted with compound (III) optionally in the presence of a base.

The amount of compound (III) to be reacted is from 1.0 to 5.0 mol or so, preferably from 1.0 to 2.0 mol or so, relative to one mol of compound (II).

The "base" includes, for example, basic salts such as sodium carbonate, potassium carbonate, cesium carbonate, sodium hydrogencarbonate, etc.; aromatic amines such as pyridine, lutidine, etc.; tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc.; alkali metal hydrides such as sodium hydride, potassium hydride, etc.; metal amides such as sodium amide, lithium diisopropylamide, lithium hexamethyldisilazide, etc.; metal alkoxides such as sodium methoxide, sodium ethoxide, potassium tert-butoxide, etc. The amount of the base to be used is from 1.0 to 5.0 mol or so, preferably from 1.0 to 2.0 mol or so, relative to one mol of compound (II).

In this reaction, advantageously used is a solvent inert to the reaction. There is no particular limitation on the kind of solvent that can be used unless the reaction is interfered with. For example, preferably used are alcohols such as methanol, ethanol, propanol, etc.; ethers such as diethyl ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; halogenated hydrocarbons such as dichloromethane, chloroform, carbon tetrachloride, 1,2-dichloroethane, etc.; nitrites such as acetonitrile, propionitrile, etc.; sulfoxides such as dimethylsulfoxide, etc.; and mixtures of those solvents.

The reaction time is generally from 30 minutes to 48 hours, preferably from 1 hour to 24 hours. The reaction temperature is generally from −20 to 200° C., preferably from 0 to 150° C.

In place of the reaction mentioned above, also employable herein is Mitsunobu reaction (see Synthesis, pp. 1–27, 1981).

In this reaction, compound (II) is reacted with compound (III) wherein L is OH in the presence of an azodicarboxylate compound (e.g., diethylazo dicarboxylate, etc.) and a phosphine compound (e.g., triphenylphosphine, tributylphosphine, etc.).

The amount of compound (III) wherein L is OH to be reacted is from 1.0 to 5.0 mol or so, preferably from 1.0 to 2.0 mol or so, relative to one mol of compound (II).

The amount of the "azodicarboxylate compound" and that of the "phosphine compound" to be used are from 1.0 to 5.0 mol or so, preferably from 1.0 to 2.0 mol or so, relative to one mol of compound (II), respectively.

In this reaction, advantageously used is a solvent inert to the reaction. There is no particular limitation on the kind of solvent that can be used unless the reaction is interfered with. For example, preferably used are ethers such as diethyl ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; halogenated hydrocarbons such as dichloromethane, chloroform, carbon tetrachloride, 1,2-dichloroethane, etc.; nitrites such as acetonitrile, propionitrile, etc.; sulfoxides such as dimethylsulfoxide, etc.; and mixtures of those solvents.

The reaction time is generally from 5 minutes to 48 hours, preferably from 30 minutes to 24 hours. The reaction temperature is generally from −20 to 200° C., preferably from 0 to 100° C.

(2) The case where $R^4$ is "an acyl" is mentioned below.

Compound (II) is reacted with compound (III) optionally in the presence of a base or acid.

The amount of compound (III) to be reacted is from 1.0 to 5.0 mol or so, preferably from 1.0 to 2.0 mol or so, relative to one mol of compound (II).

The "base" includes, for example, aromatic amines such as triethylamine, pyridine, etc.

The "acid" includes, for example, methanesulfonic acid, p-toluenesulfonic acid, camphor-sulfonic acid, etc.

The amount of the "base" to be used is from 1.0 to 10 equivalents or so, preferably from 0.8 to 2 equivalents or so, relative to compound (II).

The amount of the "acid" to be used is from 0.1 to 10 equivalents or so, preferably from 0.8 to 3 equivalents or so, relative to compound (II).

This reaction is advantageously effected in the absence of a solvent or in the presence of a solvent inert to the reaction. There is no particular limitation on the kind of solvent that can be used unless the reaction is interfered with. For example, preferably used are ethers such as diethyl ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; halogenated hydrocarbons such as dichloromethane, chloroform, carbon tetrachloride, 1,2-dichloroethane, etc.; nitrites such as acetonitrile, propionitrile, etc.; sulfoxides such as dimethylsulfoxide, etc.; nitrogen-containing aromatic hydrocarbons such as pyridine, lutidine, quinoline, etc.; and mixtures of those solvents.

The reaction temperature is generally from −20 to 150° C. or so, preferably from 0 to 100° C. The reaction time is generally from 5 minutes to 24 hours, preferably from 10 minutes to 5 hours.

The product (I) as produced in the manner mentioned above may be applied to the next reaction while it is still crude in the reaction mixture, or may be isolated from the reaction mixture in any ordinary manner. This can be easily purified through separation means such as recrystallization, distillation, chromatography and the like.

Compound (II) can be produced in any per se known manner, for example, by the methods disclosed in EP-A-273647, JP-A-1-272578, EP-A-483772, JP-A-5-140142, EP-A-345593, JP-A-2-76869, EP-A-345592, JP-A-2-76870 and JP-A-57-122080, or analogous methods thereto.

Compound (III) can be purchased from a commercial market or produced in any per se known manner.

In the case that Compound (II) is a benzofuran [compound (IIa)], it can be also obtained according to the methods of the following process.

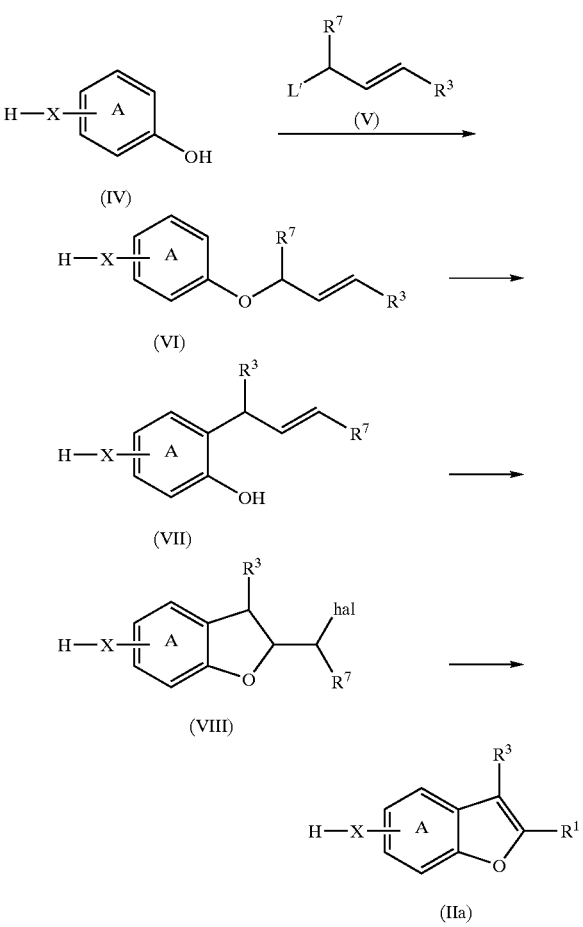

Process 2

In above formulae, L' represents a leaving group, $R^7$ represents a hydrogen atom or a group formed by removing a methylene from $R^1$ and hal represents halogen atoms (e.g., fluoro, chloro, bromo, iodo, etc).

The "leaving group" for L' includes, for example, hydroxy, halogen atoms (e.g. fluoro, chloro, bromo, iodo, etc.), $C_{1-6}$ alkylsulfonyloxy (e.g. methanesulfonyloxy, ethanesulfonyloxy, etc.), $C_{6-10}$ arylsulfonyloxy which may be substituted, etc. The "$C_{6-10}$ arylsulfonyloxy which may be substituted" includes, for example, $C_{6-10}$ arylsulfonyloxy (e.g. phenylsulfonyloxy, naphthylsulfonyloxy, etc.) which may be substituted by 1 to 3 substituents selected from the group consisting of $C_{1-6}$ alkyl, $C_{1-6}$ alkoxy and nitro. Concretely mentioned is benzenesulfonyloxy, m-nitrobenzenesulfonyloxy, p-toluenesulfonyloxy, and so forth.

Compound (IV) can be purchased from a commercial market or produced in any per se known manner.

Compound (VI) can be produced by reacting a phenolate anion, which is produced by treating compound (IV) with a base, and a compound of the formula: $R^7$—CHL'—CH=CH—$R^3$ [compound (V)].

The "base" includes, for example, inorganic bases such as alkali metal hydroxides such as sodium hydroxide, potassium hydroxide, etc.; alkali metal alkoxides such as sodium methoxide, sodium ethoxide, potassium tert-butoxide, etc.; alkali metal hydrides such as sodium hydride, potassium hydride, etc.; metal amides such as sodium amide, lithium diisopropylamide, lithium hexamethyldisilazide, etc.; and basic salts such as potassium hydrogen carbonate, sodium carbonate, potassium carbonate, sodium acetate, etc. The amount of the base is generally about from 0.5 to 5 mol, preferably about 1 to 3 mol, per mol of compound (IV).

This reaction is advantageously effected in the presence of a solvent inert to the reaction. There is no particular limitation on the kind of solvent that can be used unless the reaction is interfered with. For example, preferably used are alcohols such as methanol, ethanol, propanol, etc.; hydrocarbons such as cyclohexane, hexane, benzene, toluene, xylene, etc.; ethers such as tetrahydrofuran, dioxane, 1,2-dimethoxyethane, diethyl ether, diisopropyl ether, etc.; amides such as N,N-dimethylformamide, N,N-dimethylacetamide, hexamethylphosphoric triamide, etc.; sulfoxides such as dimethyl sulfoxide etc.; halogenated hydrocarbons such as dichloromethane, chloroform, carbon tetrachloride, 1,2-dichloroethane, etc.; ketones such as acetone, methyl ethyl ketone, etc.; water; and mixtures of these solvents.

The reaction time is generally from 10 minutes to 8 hours, preferably from 30 minutes to 3 hours. The reaction temperature is generally from 0 to 120° C., preferably from 25 to 100° C.

The reaction product can be directly used, either as the reaction mixture as such or in a partially purified form, in the next reaction. If desired, however, the product compound can be isolated from the reaction mixture in the routine manner and expediently purified by the conventional purification procedure (e.g. recrystallization, distillation, chromatography, etc.).

Compound (VII) can be produced by subjecting compound (VI) to Claisen rearrangement.

This reaction is advantageously effected in the absence of a solvent or in the presence of a solvent inert to the reaction. There is no particular limitation on the kind of solvent that can be used unless the reaction is interfered with. For example, preferably used are alcohols such as methanol, ethanol, propanol, etc.; hydrocarbons such as cyclohexane, hexane, benzene, toluene, xylene, mesitylene etc.; ethers such as tetrahydrofuran, dioxane, 1,2-dimethoxyethane, diethyl ether, diisopropyl ether, etc.; amides such as N,N-dimethylformamide, N,N-dimethylacetamide, hexamethylphosphoric triamide, etc.; sulfoxides such as dimethyl sulfoxide etc.; halogenated hydrocarbons such as dichloromethane, chloroform, carbon tetrachloride, 1,2-dichloroethane, etc.; and mixtures of these solvents.

If desired, this reaction can be conducted with acid catalyst.

The "acid catalyst" includes, for example, Lewis acid such as aluminium chloride, boron trifluoride etc. The amount of the acid catalyst is generally from about 0.1 to 20 mol, preferably from about 0.1 to 5 mol, per mol of compound (VI).

The reaction time is generally from 10 minutes to 8 hours, preferably from 30 minutes to 3 hours. The reaction temperature is from generally −70 to 300° C., preferably from 150 to 250° C.

Thus obtained compound can be submitted to the next reaction either as the reaction mixture or after partial purification, but can be easily isolated by per se known method and purified by the routine purification procedures such as recrystallization, distillation, chromatography, etc.

Compound (VIII) can also be produced by treating compound (VII) with a halogenation reagent.

The "halogenation reagent" includes, for example, halogens such as bromine, chlorine, iodine, etc.; imides such as N-bromosuccinimide, etc.; halogen adducts such as benzyltrimethylammonium dichloroiodate, benzyltrimethylammonium tribromide, etc.

The amount of the halogenation reagent is from about 1.0 to 5.0 mol, preferably from about 1.0 to 2.0 mol, per mol of compound (VII).

This reaction is advantageously effected in the presence of a solvent inert to the reaction. There is no particular limitation on the kind of solvent that can be used unless the reaction is interfered with. For example, preferably used are ethers such as diethyl ether, tetrahydrofuran, dioxane, 1,2-dimethoxyethane, etc.; alcohols such as methanol, ethanol, propanol, etc.; hydrocarbons such as benzene, toluene, cyclohexane, hexane, etc.; amides such as N,N-dimethylformamide, N,N-dimethylacetamide, etc.: halogenated hydrocarbons such as dichloromethane, chloroform, carbon tetrachloride, 1,2-dichloroethane, etc.; nitrites such as acetonitrile, propionitrile, etc.; sulfoxides such as dimethyl sulfoxide etc.; organic acids such as acetic acid, propionic acid, etc.; nitroalkanes such as nitromethane, etc.; aromatic amines such as pyridine, lutidine, quinoline, etc.; and mixtures of these solvents.

This reaction can be conducted with a base or a radical initiator, or under light exposure, where necessary.

The "base" includes, for example, basic salts such as sodium carbonate, potassium carbonate, cesium carbonate, sodium hydrogen carbonate, sodium, acetate, potassium acetate, etc; aromatic amines such as pyridine, lutidine, etc.; tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc. The amount of the bases is from about 0.8 to 10 mol, per mol of compound (VII).

The "radical initiator" includes, for example, benzoyl peroxide, azobisisobutyronitrile, etc. The amount of the radical initiator is from about 0.01 to 1 mol, per mol of compound (VII).

In the case of the light exposure, halogen lamp can be used.

The reaction temperature is about from −50 to 150° C., preferably from 0 to 100° C. The reaction time is generally from 5 minutes to 24 hours, preferably from 10 minutes to 12 hours.

Thus obtained compound can be submitted to the next reaction either as the reaction mixture or after partial purification, but can be easily isolated by per se known method and purified by the routine purification procedures such as recrystallization, distillation, chromatography, etc.

Compound (IIa) can be produced by treating compound (VIII) with a base.

The "base" includes, for example, inorganic bases such as alkali metal hydroxides e.g., sodium hydroxide, potassium hydroxide, etc.; organic bases such as trlethylamine. 1,8-diazabicyclo[5,4,0]-7-undecene, pyridine, etc.; alkali metal alkoxides such as sodium methoxide, sodium ethoxide, potassium tert-butoxide, etc.; alkali metal hydrides such as sodium hydride, potassium hydride, etc.; metal amides such as sodium amide, lithium diisopropylamide, lithium hexamethyldisilazide, etc.; basic salts such as potassium hydrogen carbonate, sodium carbonate, potassium carbonate, sodium acetate, etc.

The amount of the base is generally from about 0.5 to 10 mol, preferably about from 1 to 5 mol, per mole of compound (VIII).

This reaction is advantageously effected in the presence of a solvent inert to the reaction. There is no particular limitation on the kind of solvent that can be used unless the reaction is interfered with. For example, preferably used are alcohols such as methanol, ethanol, propanol, etc.; hydrocarbons such as cyclohexane, hexane, benzene, toluene, xylene, etc.; ethers such as tetrahydrofuran, dioxane, 1,2-dimethoxyethane, diethyl ether, diisopropyl ether, etc.; amides such as N,N-dimethylformamide, N,N-dimethylacetamide, hexamethylphosphoric triamide, etc.; sulfoxides such as dimethyl sulfoxide etc.; halogenated hydrocarbons such as dichloromethane, chloroform, carbon tetrachloride, 1,2-dichloroethane, etc.; ketones such as acetone, methyl ethyl ketone, etc.; water; and mixtures of these solvents.

The reaction time is generally from 10 minutes to 24 hours, preferably from 30 minutes to 12 hours. The reaction temperature is generally from 0 to 120° C., preferably from 25 to 100° C.

Thus obtained compound can be submitted to the next reaction either as the reaction mixture or after partial purification, but can be easily isolated by per se known method and purified by the routine purification procedures such as recrystallization, distillation, chromatography, etc.

In the above-mentioned reactions where the starting compounds are substituted by any of amino, carboxy or hydroxy, those groups may be protected by ordinary protective groups which are generally used in peptide chemistry. The protective groups may be removed after the reaction to give the intended products.

The amino-protecting group includes, for example, formyl, $C_{1-6}$ alkyl-carbonyl (e.g., acetyl, propionyl, etc.) which may be substituted, phenylcarbonyl which may be substituted, $C_{1-6}$ alkoxy-carbonyl (e.g., methoxycarbonyl, ethoxycarbonyl, etc.) which may be substituted, phenyloxycarbonyl which may be substituted, $C_{7-10}$ aralkyloxycarbonyl (e.g., benzyloxycarbonyl, etc.) which may be substituted, trityl which may be substituted, phthaloyl which may be substituted, etc. These substituents include, for example, halogen atoms (e.g., fluoro, chloro, bromo, iodo, etc.), $C_{1-6}$ alkyl-carbonyl (e.g., acetyl, propionyl, valeryl, etc.), nitro, etc. The number of those substituents is 1 to 3.

The carboxy-protecting group includes, for example, $C_{1-6}$ alkyl (e.g., methyl, ethyl, propyl, isopropyl, butyl, tert-butyl, etc.) which may be substituted, phenyl which may be substituted, trityl which may be substituted, silyl which may be substituted, etc. These substituents includes, for example, halogen atoms (e.g., fluoro, chloro, bromo, iodo, etc.), formyl, $C_{1-6}$ alkyl-carbonyl (e.g., acetyl, propionyl, butylcarbonyl, etc.), nitro, $C_{1-6}$ alkyl (e.g., methyl, ethyl, tert-butyl, etc.), $C_{6-10}$ aryl (e.g., phenyl, naphthyl, etc.), etc. The number of those substituents is 1 to 3.

The hydroxy-protecting group includes, for example, $C_{1-6}$ alkyl (e.g., methyl, ethyl, propyl, isopropyl, butyl, tert-butyl, etc.) which may be substituted, phenyl which may be substituted, $C_{7-11}$ aralkyl (e.g., benzyl, etc.) which may be substituted, formyl which may be substituted, $C_{1-6}$ alkyl-carbonyl (e.g., acetyl, propionyl, etc.) which may be substituted, phenyloxycarbonyl which may be substituted, $C_{7-11}$ aralkyl-oxycarbonyl (e.g., benzyloxycarbonyl, etc.) which may be substituted, tetrahydropyranyl which may be substituted, tetrahydrofuranyl which may be substituted, silyl which may be substituted, etc. Those substituents include, for example, halogen atoms (e.g., fluoro, chloro, bromo, iodo, etc.), $C_{1-6}$ alkyl (e.g., methyl, ethyl, tert-butyl, etc.), $C_{7-11}$ aralkyl (e.g., benzyl, etc.), $C_{6-10}$ aryl (e.g., phenyl, naphthyl, etc.), nitro, etc. The number of those substituents is 1 to 4.

Those protective groups may be removed by any per se known methods or analogous methods thereto, such as methods using acids, bases, ultraviolet rays, hydrazine, phenylhydrazine, sodium N-methyldithiocarbamate, tetrabutylammonium fluoride, palladium acetate, etc.; and reduction, etc.

The starting compounds for compound (I) include their salts, which are not specifically defined provided that the reaction with those salts gives the intended products. The above salts include, for example, the salts of compound (I) above.

For configurational isomers (E- and Z-forms) of compound (1), they may be isolated and purified through any ordinary separation means of, for example, extraction, recrystallization, distillation, chromatography and the like, to give pure products in any time when the isomers are formed. By the methods described in "Shin Jikken Kagaku Kouza (New Edition of Lectures of Experimental Chemistry)" 14, edited by the Chemical Society of Japan, pp. 251–253, and in Fourth Edition of "Shin Jikken Kagaku Kouza (Lectures of Experimental Chemistry)" 19, edited by the Chemical Society of Japan, pp. 273–274, or analogous methods thereto, the products of compound (I) being produced are specifically isomerized at the position of the double bond by heating, or with acid catalysts, transition metal catalysts or radical species catalysts, or through exposure to light, or with strong base catalysts or the like, to thereby obtain the intended pure isomers.

Compound (I) includes stereoisomers, depending on the type of the substituents therein, and both single isomers and mixtures of different isomers are within the scope of the present invention.

Compounds (I) and (Ia) may be in any form of their hydrates and non-hydrates.

In any case, products formed in the reaction mixtures may be subjected to deprotection, acylation, alkylation, hydrogenation, oxidation, reduction, chain extension, substituents-exchange reaction and combined reactions thereof, to obtain compound (I).

Where the products are formed in their free form in the reaction, they may be converted into their salts in any ordinary manner. Where they are formed in the form of their salts, they may be converted into free compounds or other salts in any ordinary manner. The thus-obtained compound (I) may be isolated and purified from the reaction mixtures through any ordinary means of, for example, trans-solvation, concentration, solvent extraction, fractionation, crystallization, recrystallization, chromatography and the like.

Where compound (I) exists in the reaction mixtures in the form of its configurational isomers, diastereomers, conformers or the like, they may be optionally isolated into single isomer through the separation and isolation means mentioned above. Where compound (I) is in the form of its racemates, they may be resolved into d- and l-forms through any ordinary optical resolution.

As compound (I) of the present invention and compound (Ia) have an suppressive effect on neurodegeneration, an activity of suppressing nerve cell death to be caused by β-amyloid, and an activity of neurotrophic factors, while having low toxicity and few side effects, they are useful as medicines.

Compound (I) of the present invention and compound (Ia) act on mammals (e.g., mouse, rat, hamster, rabbit, feline, canine, bovine, sheep, monkey, human, etc.) as neurodegeneration inhibitors and neurotrophic factor-like substances, or as β-amyloid toxicity inhibitors, and suppress the nerve cell death in those mammals. In addition, as having an activity of activating cholinergic neurons (e.g., elevation of choline acetyltransferase activity, etc.), compounds (I) and (Ia) increase the acetylcholine content of subjects to which they are administered while activating the function of the central nervous systems of the subjects. Accordingly, compounds (I) and (Ia) are effective for neurodegenerative diseases (e.g., Alzheimer's disease, Parkinson's disease, amyotrophic lateral sclerosis (ALS), Huntington's chorea, etc.), peripheral nervous system disorders (e.g., diabetic neuropathy, etc.) and the like, and are used as medicines for preventing and/or treating those diseases and disorders.

As their toxicity is low, compound (I) of the present invention and compound (Ia) are, either directly as they are or after having been formulated into pharmaceutical compositions along with pharmaceutically acceptable carriers in any per se known manner, for example, into tablets (including sugar-coated tablets, film-coated tablets), powders, granules, capsules (including soft capsules), liquid preparations, injections, suppositories, sustained release preparations, cataplasms, chewing gums, etc., safely administered orally or parenterally (e.g., locally, rectally, intravenously, etc.). In the pharmaceutical composition of the present invention, the amount of compound (I) or (Ia) is from 0.01 to 100% by weight or so of the total weight of the composition. The dose of the composition varies, depending on the subject to which the composition is administered, the administration route employed, the disorder of the subject, etc. For example, for the peroral composition for treating Alzheimer's disease, its dose to adults may be from 0.1 to 20 mg/kg of body weight or so, preferably from 0.2 to 10 mg/kg of body weight or so, more preferably from 0.5 to 10 mg/kg of body weight or so, in terms of the active ingredient of compound (I) or (Ia), and this may be administered once or several times a day. Compounds (I) and (Ia) may be combined with any other active ingredients, for example, cholinesterase inhibitor (e.g., Aricept (donepezil), etc.), brain function activator (e.g., idebenone, vinpocetine, etc.), medicine for Parkinson's disease (e.g., L-dopa, etc.), neurotrophic factors, and so forth. For example, compound (I) or (Ia) is mixed with any of those other active ingredients in any known manner, and formulated into one pharmaceutical composition (for example, in the form of tablets, powders, granules, capsules including soft capsules, liquid preparations, injections, suppositories, sustained-release preparations, etc.); or they may be formulated into separate compositions and administered to the same subject simultaneously or at time intervals.

Any ordinary organic and inorganic carrier substances that are generally used in formulating medicines are usable as the carriers for formulating the pharmaceutical compositions of the present invention. For example, employable are ordinary excipients, lubricants, binders, disintegrators, etc. for formulating solid preparations; and solvents, solubilizers, suspending agents, isotonizing agents, buffers, soothing agents, etc. for formulating liquid preparations. If desired, further employable are other additives such as preservatives, antioxidants, colorants, sweeteners, adsorbents, wetting agents, etc.

The excipients include, for example, lactose, white sugar, D-mannitol, starch, corn starch, crystalline cellulose, light silicic anhydride, etc.

The lubricants include, for example, magnesium stearate, calcium stearate, talc, colloidal silica, etc.

The binders include, for example, crystalline cellulose, white sugar, D-mannitol, dextrin, hydroxypropyl cellulose, hydroxypropylmethyl cellulose, polyvinyl pyrrolidone, starch, sucrose, gelatin, methyl cellulose, carboxymethyl cellulose sodium, etc.

The disintegrators include, for example, starch, carboxymethyl cellulose, carboxymethyl cellulose calcium, croscarmellose sodium, carboxymethyl starch sodium, L-hydroxypropyl cellulose, etc.

The solvents include, for example, water for injections, alcohol, propylene glycol, macrogol, sesame oil, corn oil, olive oil, etc.

The solubilizers include, for example, polyethylene glycol, propylene glycol, D-mannitol, benzyl benzoate, ethanol, trisaminomethane, cholesterol, triethanolamine, sodium carbonate, sodium citrate, etc.

The suspending agents include, for example, surfactants such as stearyl triethanolamine, sodium lauryl sulfate, lauryl aminopropionic acid, lecithin, benzalkonium chloride, benzethonium chloride, glycerin monostearate, etc.; hydrophilic polymers such as polyvinyl alcohol, polyvinyl pyrrolidone, carboxymethyl cellulose sodium, methyl cellulose, hydroxymethyl cellulose, hydroxyethyl cellulose, hydroxypropyl cellulose, etc.

The isotonizing agents include, for example, glucose, D-sorbitol, sodium chloride, glycerin, D-mannitol, etc.

The buffers include, for example, liquid buffers of phosphates, acetates, carbonates, citrates, etc.

The soothing agents include, for example, benzyl alcohol, etc.

The preservatives include, for example, parahydroxybenzoates, chlorobutanol, benzyl alcohol, phenethyl alcohol, dehydroacetic acid, sorbic acid, etc.

The antioxidants include, for example, sulfites, ascorbic acid, etc.

BEST MODE FOR CARRYING OUT THE INVENTION

The invention will be described in more detail hereinunder, with reference to the following Reference Examples, Examples, Formulation Examples and Experimental Examples, which, however, are to concretely illustrate some embodiments of the invention and are not intended to restrict the scope of the invention. Various changes and modifications can be made within the range that does not deviate the scope of the invention.

"Room temperature" as referred to in the following Reference Examples and Examples is meant to indicate a temperature falling between 10° C. and 35° C. Unless otherwise specifically indicated, "%" is by weight.

The meanings of the abbreviations used hereinunder are as follows:

s: singlet d: doublet t: triplet q: quartet septet:septet m: multiplet br: broad J: coupling constant Hz: Hertz $CDCl_3$: deuterated chloroform $d_6$-DMSO: deuterated dimethylsulfoxide $^1$H-NMR; proton nuclear magnetic resonance spectrum

EXAMPLES

Reference Example 1

Methyl α-bromophenylacetate

Concentrated sulfuric acid (0.5 mL) was added to a solution of α-bromophenylacetic acid (3.00 g, 13.9 mmol) in ethanol (30 mL) at room temperature, and the mixture was heated under reflux for 1 hour. The reaction mixture was cooled, and extracted twice with ethyl acetate. The organic layers were combined, washed with an aqueous saturated sodium hydrogencarbonate, then dried over magnesium sulfate, filtered, and concentrated under reduced pressure to obtain the title compound (2.50 g, yield 79%). This was oily.

$^1$H-NMR (CDCl$_3$) δ: 3.78 (3H, s), 5.36 (1H, s), 7.29–7.42 (3H, m), 7.48–7.61 (2H, m).

Reference Example 2

1-Bromo-4-(4-morpholinyl)benzene

Bromine (10.8 g, 67.4 mmol) was added to a solution of 4-(4-morpholinyl)benzene (10.0 g, 61.3 mmol) in ethanol (100 mL) at 0° C., and the mixture was stirred for 1 hour at room temperature. Water (100 mL) was poured into the reaction mixture, which was then extracted twice with ethyl acetate. The organic layers were combined, washed with an aqueous saturated sodium hydrogencarbonate and water, then dried over magnesium sulfate, filtered, and concentrated under reduced pressure. The residue was crystallized from ethyl acetate-hexane to obtain the title compound (10.7 g, yield 72%).

m.p.: 118–120° C.

$^1$H-NMR (CDCl$_3$) δ: 2.98–3.22 (4H, m), 3.71–3.92 (4H, m), 6.72–6.83 (2H, m), 7.31–7.42 (2H, m).

Reference Example 3

1-Bromo-4-(4-methyl-1-piperazinyl)benzene

Sodium hydride (60% liquid paraffin dispersion, 2.70 g, 67.8 mmol) was added to a solution of 1-phenylpiperazine (10.0 g, 61.6 mmol) in N,N-dimethylformamide (80 mL) at 0° C., and the mixture was stirred for 10 minutes at the same temperature. To the reaction mixture was added Iodomethane (8.74 g, 67.8 mmol), and the mixture was stirred for 30 minutes at room temperature. The reaction mixture was poured into water (80 mL), and extracted twice with ethyl acetate. The organic layers were combined, washed with water, dried over magnesium sulfate, filtered, and concentrated under reduced pressure. The residue was crystallized from hexane-isopropyl ether to obtain 1-methyl-4-phenylpiperazine (7.40 g). Bromine (7.00 g, 43.8 mmol) was added to a solution of this compound in ethanol (80 mL) at 0° C., and the mixture was stirred for 1 hour at room temperature. Water (80 mL) was poured into the reaction mixture, which was then extracted twice with ethyl acetate. The organic layer was combined, washed with an aqueous saturated sodium hydrogencarbonate and water, then dried over magnesium sulfate, filtered, and concentrated under reduced pressure. The residue was crystallized from ethyl acetate-hexane to obtain the title compound (8.1 g, yield 52%).

m.p.: 78–80° C.

$^1$H-NMR (CDCl$_3$) δ: 2.35 (3H, s), 2.52–2.63 (4H, m), 3.13–3.26 (4H, m), 6.78 (2H, d, J=8.8 Hz), 7.33 (2H, d, J=8.8 Hz).

Reference Example 4

2-Methyl-1-[4-(4-morpholinyl)phenyl]propan-1-one n-Butyllithium (1.6 M, 25.8 mL, 41.3 mmol) was added to a solution of 1-bromo-4-(4-morpholinyl)benzene (10.0 g, 41.3 mmol) in tetrahydrofuran (100 mL) at −78° C., and the mixture was stirred for 20 minutes at the same temperature. To the reaction mixture was added N-isobutyrylpropyleneimine (5.77 g, 45.4 mmol), and the mixture was stirred for 30 minutes at room temperature. Water (40 mL) was poured into the reaction mixture, which was then extracted twice with ethyl acetate. The organic layers were combined, washed with water, dried over magnesium sulfate, filtered, and concentrated under reduced pressure. The residue was crystallized from hexane to obtain the title compound (6.50 g, yield 67%).

m.p.: 75–77° C.

$^1$H-NMR (CDCl$_3$) δ: 1.19 (6H, d, J=7.0 Hz), 3.22–3.33 (4H, m), 3.50 (1H, septet, J=7.0 Hz), 3.81–3.92 (4H, m), 6.81–6.92 (2H, m), 7.85–8.95 (2H, m).

Reference Example 5

2-Methyl-1-[4-(4-methyl-1-piperazinyl)phenyl]propan-1-one

Using 1-bromo-4-(4-methyl-1-piperazinyl)benzene the title compound was obtained in the same manner as in Reference Example 4.

Yield: 81%.

m.p.: 74–76° C. (from methanol).

$^1$H-NMR (CDCl$_3$) δ: 1.19 (6H, d, J=6.6 Hz), 2.35 (3H, s), 2.46–2.63 (4H, m), 3.32–3.41 (4H, m), 3.50 (1H, septet, J=7.0 Hz), 6.84–6.92 (2H, m), 7.85–7.95 (2H, m).

Reference Example 6

1-(2,5-Dimethoxy-3,4,6-trimethylphenyl)-2-methyl-1-[4-(4-morpholinyl)phenyl]propan-1-ol n-Butyllithium (1.6 M, 18.1 mL, 29.0 mmol) was added to a solution of 1-bromo-2,5-dimethoxy-3,4,6-trimethylbenzene (7.52 g, 29.0 mmol) in tetrahydrofuran (50 mL) at −78° C., and the mixture was stirred for 20 minutes at the same temperature. To the reaction mixture was added 2-methyl-1-[4-(4-morpholinyl)phenyl] propan-1-one (6.15 g, 26.4 mmol), and the mixture was stirred for 30 minutes at room temperature. Water (40 mL) was poured into the reaction mixture, which was then extracted three times with ethyl acetate. The organic layers were combined, washed with water, dried over magnesium sulfate, filtered, and concentrated under reduced pressure. The residue was crystallized from ethanol to obtain the title compound (8.40 g, yield 90%).

m.p.: 191–193° C.

$^1$H-NMR (CDCl$_3$) δ: 0.87–1.10 (6H, m), 2.11 (3H, s), 2.18 (3H, s), 2.45 (3H, s), 2.80–3.18 (8H, m), 3.62 (3H, s), 3.75–3.90 (4H, m), 6.41 (1H, br s), 6.82 (2H, d, J=8.8 Hz), 7.34 (2H, d, J=8.8 Hz).

Reference Example 7

1-(2,5-Dimethoxy-3,4,6-trimethylphenyl)-2-methyl-1-[4-(4-methyl-1-piperazinyl)phenyl]propan-1-ol Using 2-methyl-1-[4-(4-methyl-1-piperazinyl)phenyl] propan-1-one, the title compound was obtained in the same manner as in Reference Example 6.

Yield: 43%.

m.p.: 114–116° C. (from methanol).

$^1$H-NMR (CDCl$_3$) δ: 0.97 (6H, t, J=6.6 Hz), 2.11 (3H, s), 2.18 (3H, s), 2.34 (3H, s), 2.45 (3H, s), 2.50–2.62 (4H, m), 2.76–3.00 (1H, m), 3.02 (3H, s), 3.10–3.28 (4H, m), 3.62 (3H, s), 6.40 (1H, br s), 6.84 (2H, d, J=8.8 Hz), 7.33 (2H, d, J=8.8 Hz).

Reference Example 8

3-(4-Isopropylphenyl)-2,2-dimethyl-2,3-dihydrobenzofuran-5-ol n-Butyllithium (1.6 M, 20.8 mL, 33.2 mmol) was added to a solution of 1-bromo-2,5-dimethoxybenzene (7.2 g, 33.2 mmol) in tetrahydrofuran (20 mL) at −78° C., and the mixture was stirred for 20 minutes at the same temperature. To the reaction mixture was added 1-(4-isopropylphenyl)-2-methylpropan-1-one (5.70 g, 30.0 mmol), and the mixture was stirred for 30 minutes at room temperature. Water (30 mL) was poured into the reaction mixture, which was then extracted three times with ethyl acetate. The organic layers were combined, washed with water, dried over magnesium sulfate, filtered, and concentrated under reduced pressure. A mixture of the residue and 48% hydrobromic acid (30 mL) was heated under reflux for 24 hours in an argon atmosphere. After cooling, water (30 mL) was added to the reaction mixture, which was then extracted twice with ethyl acetate. The organic layers were combined, washed with water, dried over magnesium sulfate, filtered, and concentrated under reduced pressure. The residue was crystallized from isopropyl ether-hexane to obtain the title compound (2.1 g, yield 70%).

m.p.: 102–104° C.

$^1$H-NMR (CDCl$_{31}$) δ: 0.96 (3H, s), 1.25 (6H, d, J=7.0 Hz), 1.57 (3H, s), 2.90 (1H, septet, J=7.0 Hz), 4.28 (1H, s), 4.67 (1H, s), 6.53–6.85 (3H, m), 7.02 (2H, d, J=8.0 Hz), 7.16 (2H, d, J=8.0 Hz).

Reference Example 9

2,2,4,6,7-Pentamethyl-3-[4-(4-morpholinyl)phenyl]-2,3-dihydrobenzofuran-5-ol

A mixture of 1-(2,5-dimethoxy-3,4,6-trimethylphenyl)-2-methyl-1-[4-(4-morpholinyl)phenyl]propan-1-ol (8.00 g, 19.3 mmol) and 48% hydrobromic acid (100 mL) was heated under reflux for 3 hours in an argon atmosphere. After cooling, an aqueous saturated sodium hydrogencarbonate (30 mL) was added to the reaction mixture, which was then extracted twice with ethyl acetate. The organic layers were combined, washed with water, dried over magnesium sulfate, filtered, and concentrated under reduced pressure. The residue was crystallized from isopropyl ether-hexane to obtain the title compound (6.40 g, yield 90. %).

m.p.: 91–93° C.

$^1$H-NMR (CDCl$_3$) δ: 1.00 (3H, s), 1.46 (3H, s), 1.82 (3H, s), 2.15 (3H, s), 2.17 (3H, s), 2.98–3.24 (4H, m), 3.71–3.99 (4H, m), 4.04 (1H, s), 4.18 (1H, s), 6.44–7.10 (4H, m).

Reference Example 10

2,2,4,6,7-Pentamethyl-3-[4-(4-methyl-1-piperazinyl)phenyl]-2,3-dihydrobenzofuran-5-ol Using 1-(2,5-dimethoxy-3,4,6-trimethylphenyl)-2-methyl-1-[4-(4-methyl-1-piperazinyl)phenyl]propan-1-ol the title compound was obtained in the same manner as in Reference Example 9.

Yield: 55%.

m.p.: 159–161° C. (from ethyl acetate-hexane).

$^1$H-NMR (CDCl$_3$) δ: 1.00 (3H, s), 1.46 (3H, s), 1.81 (3H, s), 2.17 (6H, s), 2.34 (3H, s), 2.48–2.65 (4H, m), 3.08–3.22 (4H, m), 4.03 (1H, s), 6.58–7.20 (4H, m), 1H not confirmed.

Reference Example 11

1-(4-Isopropylphenyl)propan-1-ol

Propionyl chloride (11.6 g, 125 mmol) was dropwise added to a suspension of aluminium chloride (16.7 g, 125 mmol) and cumene (18.0 g, 150 mmol) in carbon disulfide (30 mL) at −5° C., and the mixture was stirred for 30 minutes at room temperature. The reaction mixture was poured into water with ice, and the organic layer was separated, washed with an aqueous saturated sodium hydrogencarbonate and water, dried over magnesium sulfate, filtered, and concentrated under reduced pressure to obtain 1-(4-isopropylphenyl)propan-1-one (24.7 g). Sodium borohydride (1.29 g, 34.2 mmol) was added to a solution of the thus-obtained compound (13.0 g, 68.4 mmol) in ethanol (80 mL) with cooling with ice, and the mixture was stirred for 30 minutes at room temperature. Water was added to the reaction mixture, which was then extracted with ethyl acetate. The organic layer was washed with water, dried over magnesium sulfate, filtered, and concentrated under reduced pressure to obtain the title compound (11.5 g, yield 79%). This was oily.

$^1$H-NMR (CDCl$_3$) δ: 0.91 (3H, t, J=7.4 Hz), 1.25 (6H, d, J=7.0 Hz), 1.63–1.92 (2H, m), 1.94 (1H, br s), 2.90 (1H, septet, J=7.0 Hz), 4.47–4.61 (1H, m), 7.16–7.29 (4H, m).

Reference Example 12

2-[1-(4-Isopropylphenyl)propyl]-3,5,6-trimethyl-1,4-benzoquinone

Boron trifluoride/ethyl ether complex (1.30 g, 9.33 mmol) was dropwise added to a suspension of 1-(4-isopropylphenyl)propan-1-ol (5.00 g, 28.0 mmol) and trimethylhydroquinone (4.30 g, 28.0 mmol) in 1,2-dichloroethane (100 mL) at 60° C. in a nitrogen atmosphere, and the mixture was stirred for 3 hours at the same temperature. After cooling, the reaction mixture was washed with an aqueous solution of iron(III) chloride and water, dried over magnesium sulfate, filtered, and concentrated under reduced pressure. The residue was subjected to silica gel column chromatography (hexane/ethyl acetate=30/1) to obtain the title compound (5.40 g, yield 62%).

m.p.: 61–63° C. (from methanol).

$^1$H-NMR (CDCl$_3$) δ: 0.91 (3H, t, J=7.4 Hz), 1.22 (6H, d, J=6.8 Hz), 1.83–2.11 (11H, m), 2.85 (1H, septet, J=6.8 Hz), 4.02–4.23 (1H, m), 7.02–4.24 (4H, m).

Reference Example 13

3-(4-Isopropylphenyl)-2,4,6,7-tetramethylbenzofuran-5-ol

A solution of 2-[1-(4-isopropylphenyl)propyl]-3,5,6-trimethyl-1,4-benzoquinone (1.00 g, 0.324 mmol) in ethanol (1.00 liter) was stirred for 5 hours while cooling it with ice-water to keep the solution at room temperature and while exposing it to light from 400 W Bromcinelight Deluxe (manufactured by LPL Co.). The solvent was removed under reduced pressure, and the residue was subjected to silica gel column chromatography (hexane/ethyl acetate=20/1) to obtain the title compound (0.90 g, yield 90%). This was oily.

$^1$H-NMR (CDC$_3$) δ: 1.31 (6H, d, J=7.0 Hz), 1.98 (3H, s), 2.28 (3H, s), 2.30 (3H, s), 2.43 (3H, s), 2.97 (1H, septet, J=7.0 Hz), 4.43 (1H, s), 7.26 (4H, s).

Reference Example 14

2,3,6-Trimethyl-4-[(3-phenyl-2-propenyl)oxy]phenyl acetate

To a solution of 4-hydroxy-2,3,6-trimethylphenyl acetate (10.0 g, 51.5 mmol) in N,N-dimethylformamide (100 mL)

was added 1-chloro-3-phenyl-2-propene (7.86 g, 51.5 mmol) and potassium carbonate (7.10 g, 51.5 mmol) and the mixture was stirred under an argon atmosphere at 60° C. for 2 hours. This reaction mixture was poured into water and extracted twice with ethyl acetate. The combined extract was washed with water, dried over magnesium sulfate, and concentrated under reduced pressure. The residue was crystallized from methanol to obtain the title compound (13.0 g, yield 81%).

m.p.: 104–107° C.

$^1$H-NMR (CDCl$_3$) δ: 2.06 (3H, s), 2.13 (3H, S), 2.18 (3H, s), 2.34 (3H, s), 4.66 (2H, dd, J=5.6, 1.2 Hz), 6.43 (1H, dt, J=16.2, 5.6 Hz), 5.63 (1H, s), 6.74 (1H, d, J=16.2 Hz), 7.24–7.46 (5H, m).

Reference Example 15

4-Hydroxy-2,3,6-trimethyl-5-(1-phenyl-2-propenyl) phenyl acetate

A solution of 2,3,6-trimethyl-4-((3-phenyl-2-propenyl)oxy]phenyl acetate (10.0 g, 32.2 mmol) in N,N-dimethylaniline (70 mL) was stirred under an argon atmosphere at 200° C. for 3 h. After the reaction mixture was cooled, it was diluted with ethyl acetate, washed with 2N hydrochloric acid, and water, and dried over magnesium sulfate, and concentrated under reduced pressure. The residue was recrystallized from ethyl acetate-hexane to obtain the title compound (7.80 g, yield 78%).

m.p.: 136–138° C.

$^1$H-NMR (CDCl$_3$) δ: 2.06 (6H, s), 2.11 (3H, s), 2.33 (3H, s), 4.83–5.18 (2H, m), 5.36 (1H, d, J=10.0 Hz), 6.32–6.58 (1H, m), 7.18–7.37 (5H, m), 1H not confirmed.

Reference Example 16

2,4,6,7-Tetramethyl-3-phenylbenzofuran-5-yl acetate

To a suspension of 4-hydroxy-2,3,6-trimethyl-5-(1-phenyl-2-propenyl)phenyl acetate (5.10 g, 16.4 mmol) and calcium carbonate (2.13 g, 21.3 mmol) in tetrahydrofuran (20 mL) and methanol (20 mL) was added benzyltrimethylammonium dichloroiodate (6.28 g, 18.0 mmol) slowly. The mixture was stirred at room temperature for 30 minutes. The insoluble material was removed by filtration and the filtrate was concentrated under reduced pressure. To the residue was added ethyl acetate and water. The organic layer was separated and the aqueous layer was extracted twice with ethyl acetate. The combined organic layer was washed with 10% aqueous sodium hydrogen sulfite, water, an aqueous saturated solution of sodium bicarbonate and brine. The organic layer was dried over magnesium sulfate, treated with activated carbon, filtrated and the filtrate was concentrated in vacuo to provide 5.30 g of 2-iodomethyl-4,6,7-trimethyl-3-phenyl-2,3-dihydrobenzofuran-5-yl acetate. A mixture of this compound (5.30 g, 12.1 mmol) and 1,8-diazabicyclo[5,4,0]-7-undecene (9.0 m, 60.0 mmol) in toluene (20 mL) was stirred under an argon atmosphere at 100° C. for 3 hours. To that mixture was added water, and the mixture was extracted with ethyl acetate. The extract was washed with 2N hydrochloric acid, and water, dried over magnesium sulfate, and concentrated under reduced pressure. The residue was purified by silica gel column chromatography (hexane/ethyl acetate=20/1) to obtain the title compound (4.0 g, yield 79%). This was oily.

$^1$H-NMR (CDCl$_3$) δ: 1.85 (3H, s), 2.15 (3H, s), 2.30 (3H, s), 2.33 (3H, s), 2.44 (3H, s), 7.32–7.48 (5H, m).

Reference Example 17

2,4,6,7-Tetramethyl-3-phenylbenzofuran-5-ol

To a solution of 2,4,6,7-tetramethyl-3-phenylbenzofuran-5-yl acetate (4.00 g, 13.0 mmol) in a mixture of tetrahydrofuran (32 mL) and methanol (8 mL) was added 8N sodium hydroxide solution (2.0 mL) dropwise and the mixture was stirred at 40° C. for 1 hour. The solvent was then distilled off under reduced pressure. To the residue was added 2N hydrochloric acid, and the mixture was extracted with ethyl acetate. The extract was washed with water and brine, dried over magnesium sulfate, and concentrated under reduced pressure. The residue was recrystallized from isopropyl ether-hexane to obtain the title compound (3.0 g, yield 87%).

m.p.: 102–104° C.

$^1$H-NMR (CDCl$_3$) δ: 1.96 (3H, s), 2.28 (3H, s), 2.29 (3H, s), 2.44 (3H, s), 4.42 (1H, s), 7.28–7.43 (5H, m).

Reference Example 18

1-(2,4-Dimethoxyphenyl)-1-(4-isopropylphenyl)-2-methylpropan-1-ol

Using 1-bromo-2,4-dimethoxybenzene and 1-(4-isopropylphenyl)-2-methylpropan-1-one the title compound was obtained in the same manner as in Reference Example 6. Yield 56%.

m.p.: 80–81° C. (from methanol).

$^1$H-NMR(CDCl$_3$) δ: 0.75 (3H, d, J=6.6 Hz), 1.08 (3H, d, J=6.6 Hz), 1.20 (6H, d, J=7.0 Hz), 2.66 (1H, septet, J=7.0 Hz), 2.80 (1H, septet, J=6.6 Hz), 3.48 (3H, s), 3.79 (3H, s), 4.71 (1H, s), 6.39–6.40 (1H, m), 6.50–6.56 (1H, m), 7.04–7.08 (2H, m), 7.19–7.23 (2H, m), 7.40–7.44 (1H, m).

Reference Example 19

3-(4-Isopropylphenyl)-2,2-dimethyl-2,3-dihydrobenzofuran-6-ol

A mixture of 1-(2,4-dimethoxyphenyl)-1-(4-isopropylphenyl)-2-methylpropan-1-ol (5.58 g, 17.0 mmol) and 48% hydrobromic acid (30 mL) was heated under reflux for 24 hours in an argon atmosphere. After the reaction mixture was cooled, an aqueous saturated sodium hydrogencarbonate was added to the mixture, which was then extracted twice with ethyl acetate. The organic layers were combined, washed with brine, dried over magnesium sulfate, filtered, and concentrated under reduced pressure. The residue was subjected to silica gel column chromatography (hexane/ethyl acetate=20/1 to 10/1) to obtain the title compound (2.43 g, yield 51%).

m.p.: 114–115° C. (from hexane).

$^1$H-NMR(CDCl) δ: 0.95 (3H, s), 1.24 (6H, d, J=7.0 Hz), 1.57 (3H, s), 2.89 (1H, septet, J=7.0 Hz), 4.25 (1H, s), 6.15 (1H, br), 6.34–6.38 (2H, m), 6.84–6.88 (1H, m), 6.99–7.03 (2H, m), 7.13–7.17 (2H, m).

Reference Example 20

4-(4-Isopropylbenzoyl)piperidine

To 1-acetylisonipecotic acid (41.74 g, 243.8 mmol) was added thionyl chloride (200 mL), and the resulting mixture was stirred for 30 minutes. The mixture was diluted with petroleum ether. The precipitated solid was collected and washed with petroleum ether to afford 1-acetylisonipecotoyl chloride. This was added to a stirring mixture of cumene (120 mL) and aluminium chloride (69.6 g, 522 mmol) and the resulting mixture was stirred at 110° C. for 1 hour. The mixture was poured into ice, and extracted twice with ethyl acetate. The organic layers were combined, washed with brine, a dried over magnesium sulfate, filtered, and concentrated under reduced pressure. To the residue was added concentrated hydrochloric acid (100 mL), and the mixture was refluxed for 12 hours. The mixture was cooled to room temperature and was washed twice with diethyl ether. The aqueous solution was made basic with 8N sodium hydroxide solution and then extracted twice with ethyl acetate. The organic layers were combined, washed with an aqueous saturated sodium hydrogencarbonate, dried over magnesium sulfate, filtered, and concentrated under reduced pressure. The residue was crystallized from ethyl acetate-hexane to obtain the title compound (23.5 g, yield 41%).

m.p.: 55–57° C.

$^1$H-NMR(CDCl$_3$) δ: 1.27 (6H, d, J=6.8 Hz), 1.57–2.70 (5H, m), 2.70–2.83 (2H, m),2.97 (1H, septet, J=6.8 Hz), 3.16–3.22 (2H, m), 3.34–3.46 (1H, m), 7.30–7.34 (2H, m), 7.87–7.91 (2H, m).

Reference Example 21

1-Benzyl-4-(4-isopropylbenzoyl)piperidine

To a solution of 4-(4-isopropylbenzoyl)piperidine in N,N-dimethylformamide (100 mL), potassium carbonate (9.60 g, 69.5 mmol) and benzyl bromide (8.50 g, 71.5 mmol) were added, and the resulting mixture was stirred for 20 hours at room temperature. The mixture was poured into water, and extracted twice with ethyl acetate. The organic layers were combined, washed with an aqueous saturated sodium hydrogencarbonate, dried over magnesium sulfate, filtered, and concentrated under reduced pressure. The residue was crystallized from hexane to obtain the title compound (13.53 g, yield 66%).

m.p.: 76–77° C.

$^1$H-NMR(CDCl$_3$) δ: 1.26 (6H, d. J=7.0 Hz), 1.79–1.90 (4H, m), 2.07–2.20 (2H, m), 2.92–2.99 (3H, m), 3.15–3.30 (1H, m), 3.55 (2H, s), 7.24–7.32 (7H, m), 7.85–7.89 (2H, m).

Reference Example 22

(1-Benzyl-4-piperidyl)(2,5-dimethoxy-3,4,6-trimethylphenyl)(4-isopropylphenyl)methanol n-Butyllithium (1.6 M, 12.0 mL, 19.2 mmol) was added to a solution of 1-bromo-2,5-dimethoxy-3,4,6-trimethylbenzene (4.89 g, 18.87 mmol) in tetrahydrofuran (100 mL) at −78° C., and the mixture was stirred for 30 minutes at the same temperature. To the reaction mixture was added 1-benzyl-4-(4-isopropylbenzoyl)piperidine (5.02 g, 15.6 mmol). The mixture was stirred for 30 minutes at the same temperature, then poured into the water, and extracted twice with ethyl acetate. The organic layers were combined, washed with an aqueous saturated sodium hydrogencarbonate, dried over magnesium sulfate, filtered, and concentrated under reduced pressure. The residue was crystallized from ethyl acetate-hexane to obtain the title compound (6.54 g, yield 83%).

m.p.: 105–108° C.

$^1$H-NMR(CDCl$_3$) δ: 1.19 (6H, d, J=6.6 Hz), 1.2–1.5 (2H, m), 1.8–2.0 (4H, m), 2.09 (3H, s), 2.17 (3H, s), 2.39 (3H, s), 2.4–2.5 (1H, m), 2.78–2.88 (3H, m), 2.97 (3H, s), 3.51 (2H, s), 3.60 (3H, s), 6.37 (1H, br), 7.08–7.12 (2H, m), 7.26–7.34 (7H, m).

Reference Example 23

1'-Benzyl-3-(4-isopropylphenyl)-4,6,7-trimethylspiro[benzofuran-2(3H),4'-piperidine]-5-ol To a solution of (1-benzyl-4-piperidyl)(2,5-dimethoxy-3,4-trimethylphenyl)(4-isopropylphenyl)methanol (6.41 g, 12.8 mmol) in acetic acid (50 mL) was added 48% hydrobromic acid (60 mL), and the mixture was heated under reflux for 15 hours in an argon atmosphere. The reaction mixture was cooled to room temperature, made basic with 8N sodium hydroxide solution, and extracted twice with ethyl acetate. The organic layers were combined, washed with an aqueous saturated sodium hydrogencarbonate, dried over magnesium sulfate, filtered, and concentrated under reduced pressure. The residue was crystallized from ethyl acetate-hexane to obtain the title compound (4.44 g, yield 76%).

m.p.: 190–192° C.

$^1$H-NMR(CDCl$_3$) δ: 1.19 (6H, d, J=7.0 Hz), 1.21–1.41 (2H, m), 1.71–2.00 (5H, m), 2.17 (3H, s), 2.20 (3H, s), 2.27–2.90 (5H, m), 2.97 (3H, s), 3.54 (2H, s), 4.02 (1H, s), 6.6–7.1 (4H, m), 7.20–7.32 (5H, m), 1H not confirmed.

Reference Example 24

3-(4-Isopropylphenyl)-4,6,7-trimethylspiro[benzofuran-2(3H),4'-piperidine]-5-ol hydrochloride To a solution of 1'-benzyl-3-(4-isopropylphenyl)-4,6,7-trimethylspiro[benzofuran-2(3H),4'-piperidine]-5-ol (3.51 g, 7.70 mmol) and triethylamine (1.1 mL, 7.9 mmol) in chloroform (40 mL) α-chloroethyl chloroformate (2.30 g, 16.1 mmol) was added at 0° C. The mixture was refluxed for 1 hour and concentrated under reduced pressure. The residue was refluxed in methanol (20 mL) for 1 hour and concentrated under reduced pressure. The residue was crystallized from ethanol-ethyl acetate to obtain the title compound (2.80 g, yield 90%).

m.p.: >245° C. (dec.)

$^1$H-NMR(d$_6$-DMSO) δ: 1.18 (6H, d, J=6.6 Hz), 1.34 (2H, br), 1.71 (3H, s), 1.97 (2H, br), 2.08 (3H, s), 2.11 (3H, s), 2.8–3.3 (5H, m), 4.26 (1H, s). 6.6–7.2 (4H, m), 7.53 (1H, s), 8.78 (1H, s), 1H not confirmed.

Reference Example 25

3-(4-Isopropylphenyl)-1',4,6,7-tetramethylspiro[benzofuran-2(3H), 4'-piperidine]-5-ol A mixture of 3-(4-isopropylphenyl)-4,6,7-trimethylspiro[benzofuran-2(3H),4'-piperidine]-5-ol hydrochloride (2.80 g, 6.97 mmol), formic acid (30 mL) and 37% formalin (30 mL) was stirred for 15 hours at 100° C. The reaction mixture was cooled to room temperature, made basic with 8N sodium hydroxide solution, and extracted twice with ethyl acetate. The organic layers were combined, washed with an aqueous saturated sodium hydrogencarbonate, dried over magnesium sulfate, filtered, and concentrated under reduced pressure. The residue was subjected to silica gel column chromatography (Chromatorex NH DM1020, Fuji Silysia Chemical LTD) (hexane/ethyl acetate=1/1) to obtain the title compound (2.05 g, yield 77%).

m.p.: 114–117° C. (from ethyl acetate-hexane).

$^1$H-NMR(CDCl$_3$) δ: 1.18–1.39 (8H, m), 1.72–2.91 (19H, m), 4.02 (1H, m), 6.6–7.1 (4H, m), 1H not confirmed.

Reference Example 26

(1-Benzyl-4-piperidyl)(2.5-dimethoxy-3,4,6-trimethylphenyl)methanol n-Butyllithium (1.6 M, 19.5 mL, 31.2 mmol) was added to a solution of 1-bromo-2,5-dimethoxy-3,4,6-trimethylbenzene (8.00 g, 30.87 mmol) in tetrahydrofuran (80 mL) at −78° C., and the mixture was stirred for 30 minutes at the same temperature. To the reaction mixture was added 1-benzyl-4-formylpiperidine (6.23 g, 30.65 mmol). The mixture was stirred for 30 minutes at room temperature, then poured into water, and extracted twice with ethyl acetate. The organic layers were combined, washed with an aqueous saturated sodium hydrogencarbonate, dried over magnesium sulfate, filtered, and concentrated under reduced pressure. The residue was subjected to silica gel column chromatography (ethyl acetate) to obtain the title compound (6.17 g, yield 52%). This was oily.

$^1$H-NMR(CDCl$_3$) δ: 1.17–2.05 (7H, m), 2.16 (3H, s), 2.17(3H, s), 2.24 (3H, s), 2.79–2.85 (1H, m), 2.98–3.05 (1H, m), 3.48 (2H, s), 3.61 (3H, s), 3.75 (3H, s), 4.59 (1H, m), 7.23–7.32 (5H, m), 1H not confirmed.

Reference Example 27

1'-Benzyl-4,6,7-trimethylspiro[benzofuran-2(3H),4' piperidine]-5-ol

To a solution of (1-benzyl-4-piperidyl)(2,5-dimethoxy-3,4,6-trimethylphenyl)methanol (6.10 g, 15.9 mmol) in acetic acid (30 mL) was added 48% hydrobromic acid (40 mL), and the mixture was heated under reflux for 15 hours in an argon atmosphere. The reaction mixture was cooled to room temperature, made basic with 8N sodium hydroxide solution, and extracted twice with ethyl acetate. The organic layers were combined, washed with an aqueous saturated sodium hydrogencarbonate, dried over magnesium sulfate, filtered, and concentrated under reduced pressure. The residue was subjected to silica gel column chromatography (hexane/ethyl acetate=1/1) to obtain the title compound (4.60 g, yield 86%). This was amorphous.

$^1$H-NMR(CDCl$_3$) δ1.71–2.00 (6H, m), 2.10 (3H, s), 2.11 (3H, s), 2.12 (3H, s), 2.58 (2H, m), 2.87 (2H, s), 3.56 (2H, s), 7.25–7.38 (5H, m), 1H not confirmed.

Example 1

5-Benzyloxy-3-(4-isopropylphenyl)-2,2,4,6,7-pentamethyl-2,3-dihydrobenzofuran

Sodium hydride (60% liquid paraffin dispersion, 68 mg, 1.70 mmol) was added to a solution of 3-(4-isopropylphenyl)-2,2,4,6,7-pentamethyl-2,3-dihydrobenzofuran-5-ol (0.5 g, 1.54 mmol) in N,N-dimethylformamide (20 mL) at 0° C., and the mixture was stirred for 10 minutes at the same temperature. To the reaction mixture was added benzyl bromide (290 mg, 1.70 mmol) and the mixture was stirred for further 30 minutes at room temperature. The reaction mixture was poured Into water (30 mL), and extracted twice with ethyl acetate. The organic layers were combined, washed with water, dried over magnesium sulfate, filtered, and concentrated under reduced pressure. The residue was crystallized from methanol to obtain the title compound (380 mg, yield 60%).

m.p.: 79–81° C.

$^1$H-NMR (CDCl$_3$) δ: 1.01 (3H, s), 1.22 (6H, d, J=6.8 Hz), 1.50 (3H, s), 1.83 (3H, s), 2.16 (3H, s), 2.24 (3H, s), 2.86 (1H, septet, J=6.8 Hz), 4.09 (1H, s), 4.70 (2H, s), 6.70–7.00 (2H, br), 7.09 (2H, d, J=8.4 Hz), 7.30–7.50 (5H, m).

Example 2

5-Benzyloxy-3-[4-(dimethylamino)phenyl]-2,2,4,6,7-pentamethyl-2,3-dihydrobenzofuran Using 3-[(4-(dimethylamino)phenyl]-2,2,4,6,7-pentamethyl-2,3-dihydrobenzofuran-5-ol and benzyl bromide, the title compound was obtained in the same manner as in Example 1.

Yield: 40%.

m.p.: 110–112° C. (from methanol).

$^1$H-NMR (CDCl$_3$) δ: 1.03 (3H, s), 1.48 (3H, s), 1.87 (3H, s), 2.16 (3H, s), 2.23 (3H, s), 2.91 (6H, s), 4.04 (1H, s), 4.70 (2H, s), 6.48–7.16 (4H, m), 7.20–7.48 (5H, m).

Example 3

5-Benzyloxy-2,4,6,7-tetramethyl-2-(4-phenyl-1-piperazinyl)methyl-2,3-dihydrobenzofuran Using 2,4,6,7-tetramethyl-2-(4-phenyl-1-piperazinyl) methyl-2,3-dihydrobenzofuran-5-ol and benzyl bromide, the title compound was obtained in the same manner as in Example 1.

Yield: 48%.

m.p.: 120–121° C. (from methanol).

$^1$H-NMR (CDCl$_3$) δ: 1.47 (3H, s), 2.09 (3H, s), 2.16 (3H, s), 2.20 (3H, s), 2.58–2.92 (7H, m), 3.08–3.22 (5H, m), 4.71 (2H, s), 6.78–6.94 (3H, m), 7.20–7.52 (7H, m).

Example 4

3-(4-Isopropylphenyl)-5-(4-methoxybenzyloxy)-2,2,4,6,7-pentamethyl-2,3-dihydrobenzofuran Using 3-(4-isopropylphenyl)-2,2,4,6,7-pentamethyl-2,3-dihydrobenzofuran-5-ol and 4-methoxybenzyl chloride, the title compound was obtained in the same manner as in Example 1.

Yield: 49%.

m.p.: 95–96° C. (from methanol).

$^1$H-NMR (CDCl$_3$) δ: 1.00 (3H, s), 1.22 (6H, d, 3=7.0 Hz), 1.49 (3H, s), 1.82 (3H, s), 2.16 (3H, s), 2.23 (3H, s), 2.86 (1H, septet, J=7.0 Hz), 3.81 (3H, s), 4.08 (1H, s), 4.63 (2H, s), 6.70–7.18 (6H, m), 7.35 (2H, d, J=8.8 Hz).

Example 5

3-(4-Isopropylphenyl)-5-(4-methoxybenzyloxy)-2,2-dimethyl-2,3-dihydrobenzofuran

Using (4-isopropylphenyl)-2,2-dimethyl-2,3-dihydrobenzofuran-5-ol and 4-methoxybenzyl chloride, the title compound was obtained in the same manner as in Example 1.

Yield: 75%.

m.p.: 124–126° C. (from ethyl acetate-hexane).

$^1$H-NMR (CDCl$_3$) δ: 0.95 (3H, s), 1.25 (6H, d, J=7.0 Hz), 1.57 (3H, s), 2.90 (septet, 1H, J=7.0 Hz), 3.71 (3H, s), 4.30 (1H, s), 4.87 (2H, s), 6.65–7.35 (11H, m).

Example 6

3-[4-(Dimethylamino)phenyl]-5-(4-methoxybenzyloxy)-2,2,4,6,7-pentamethyl-2,3-dihydrobenzofuran Using 3-[4-(dimethylamino)phenyl]-2,2,4,6,7-pentamethyl-2,3-dihydrobenzofuran-5-ol and 4-methoxybenzyl chloride, the title compound was obtained in the same manner as in Example 1.

Yield: 42%.

m.p.: 105–107° C. (from ethanol).

$^1$H-NMR (CDCl$_3$) δ: 1.02 (3H, s), 1.48 (3H, s), 1.84 (3H, s), 2.15 (3H, s), 2.23 (3H, s), 2.92 (6H, s), 3.81 (3H, s), 4.04 (1H, s), 4.58–4.69 (2H, m), 6.54–6.93 (6H, m), 7.30–7.42 (2H, m).

Example 7

5-(4-Methoxybenzyloxy)-3-[4-(4-morpholinyl)phenyl]-2,2,4,6,7-pentamethyl-2,3-dihydrobenzofuran Using 2,2,4,6,7-pentamethyl-3-[4-(4-morpholinyl)phenyl]-2,3-dihydrobenzofuran-5-ol and 4-methoxybenzyl chloride, the title compound was obtained in the same manner as in Example 1.

Yield: 38%.

m.p.: 110–112° C. (ethanol).

$^1$H-NMR (CDCl$_3$) δ: 1.01 (3H, s), 1.48 (3H, s), 1.83 (3H, s), 2.15 (3H, s), 2.23 (3H, s), 3.02–3.26 (4H, m), 3.71–3.99 (7H, m), 4.05 (1H, s), 4.57–4.90 (2H, m), 6.60–7.00 (6H, m), 7.35 (2H, d, J.=6.8 Hz).

Example 8

5-(4-Methoxybenzyloxy)-2,2,4,6,7-pentamethyl-3-[4-(4-methyl-1-piperazinyl)phenyl]-2,3-dihydrobenzofuran Using 2,2,4,6,7-pentamethyl-3-[4-(4-methyl-1-piperazinyl)phenyl]-2,3-dihydrobenzofuran-5-ol and 4-methoxybenzyl chloride, the title compound was obtained in the same manner as In Example 1.

Yield: 42%.

m.p.: 121–122° C. (from ethyl ether-hexane).

$^1$H-NMR (CDCl$_3$) δ: 1.01 (3H, s), 1.48 (3H, s), 1.83 (3H, s), 2.15 (3H, s), 2.23 (3H, s), 2.34 (3H, s), 2.52–2.63 (4H, m), 3.13–3.24 (4H, m), 3.81 (3H, s), 4.05 (1H, s), 4.58–4.67 (2H, m), 6.60–7.07 (6H, m), 7.35 (2H, d, J=8.8 Hz).

Example 9

3-(4-Isopropylphenyl)-2,2,4,6,7-pentamethyl-5-(4-methylthiobenzyloxy)-2,3-dihydrobenzofuran Using 3-(4-isopropylphenyl)-2,2,4,6,7-pentamethyl-2,3-dihydrobenzofuran-5-ol and 4-(bromomethyl)phenyl methyl sulfide, the title compound was obtained in the same manner as in Example 1.

Yield: 70%.

m.p.: 118–120° C. (from ethanol).

$^1$H-NMR (CDCl$_3$) δ: 1.01 (3H, s), 1.22 (6H, d, J=7.0 Hz), 1.49 (3H, s), 1.82 (3H, s), 2.16 (3H, s), 2.22 (3H, s), 2.48 (3H, s), 2.86 (1H, septet, J=7.0 Hz), 4.08 (1H, s), 4.65 (2H, s), 6.80–7.02 (2H, br), 7.08 (2H, d, J=8.0 Hz), 7.25 (2H, d, J=8.4 Hz), 7.36 (2H, d, J=8.4 Hz).

Example 10

3-(4-Isopropylphenyl)-2,2,4,6,7-pentamethyl-5-[4-(methylsulfinyl)benzyloxy]-2,3-dihydrobenzofuran Sodium periodate (0.766 g, 3.58 mmol) was added to a solution of 3-(4-isopropylphenyl)-2,2,4,6,7-pentamethyl-5-(4-methylthiobenzyloxy)-2,3-dihydrobenzofuran (1.50 g, 3.26 mmol) in a mixture of ethanol (80 mL) and water (8 mol), and the mixture was heated under reflux for 2 hours. To the reaction mixture were added ethyl acetate and water to separate it into two layers, and the aqueous layer was extracted with ethyl acetate. The organic layers were combined, washed with water, dried over magnesium sulfate, filtered, and concentrated under reduced pressure. The resulting residue was recrystallized from ethyl acetate-hexane to obtain the title compound (1.23 g, yield 79%).

m.p.: 132–134° C.

$^1$H-NMR (CDCl$_3$) δ: 1.02 (3H, s), 1.22 (6H, d, J=6.8 Hz), 1.50 (3H, s), 1.82 (3H, s), 2.17 (3H, s), 2.23 (3H, s), 2.71, 2.72 (1.51H×2, s×2), 2.86 (1H, septet, J=6.8-Hz), 4.09 (1H, s), 4.76 (2H, s), 6.71–7.15 (4H, m), 7.57–7.69 (4H, m).

Example 11

3-(4-Isopropylphenyl)-2,2,4,6,7-pentamethyl-5-[4-(methylsulfonyl)benzyloxy]-2,3-dihydrobenzofuran Sodium periodate (2.02 g, 9.45 mmol) was added to a solution of 3-(4-isopropylphenyl)-2,2,4,6,7-pentamethyl-5-[(4-methylsulfinyl)benzyloxy]-2,3-dihydrobenzofuran (1.50 g, 3.15 mmol) in a mixture of ethanol (80 mL) and water (8 mol), and the mixture was heated under reflux for 18 hours. To the reaction mixture were added ethyl acetate and water to separate it into two layers, and the aqueous layer was extracted with ethyl acetate. The organic layers were combined, washed with water, dried over magnesium sulfate, filtered, and concentrated under reduced pressure. The resulting residue was recrystallized from ethyl acetate-hexane to obtain the title compound (1.05 g, yield 68%).

m.p.: 161–162° C.

$^1$H-NMR (CDCl$_3$) δ: 1.02 (3H, s), 1.22 (6H, d, J=7.0 Hz), 1.50 (3H, s), 1.82 (3H, s), 2.17 (3H, s), 2.22 (3H, s), 2.87 (1H, septet, J=7.0 Hz), 3.05 (3H, s), 4.09 (1H, s), 4.80 (2H, s), 6.70–7.13 (4H, m), 7.67 (2H, d, J 8.4 Hz), 7.95 (2H, d, J=8.4 Hz).

Example 12

3-(4-Isopropylphenyl)-2,2,4,6,7-pentamethyl-5-(3-phenyl-2-propen-1-yloxy)-2,3-dihydrobenzofuran Using 3-(4-isopropylphenyl)-2,2,4,6,7-pentamethyl-2,3-dihydrobenzofuran-5-ol and 3-bromo-1-phenyl-1-propene, the title compound was obtained in the same manner as in Example 1.

Yield: 71%.

m.p.: 106–107° C. (from methanol).

$^1$H-NMR (CDCl$_2$) δ: 1.00 (3H, s), 1.21 (6H, d, J=7.0 Hz), 1.49 (3H, s), 1.86 (3H, s), 2.16 (3H, s), 2.24 (3H, s), 2.85 (1H, septet, J=7.0 Hz), 4.08 (1H, s), 4.36 (2H, d, J=6.0 Hz), 6.42 (1H, dt, J=15.4, 6.0 Hz), 6.66–7.15 (5H, m), 7.20–7.48 (5H, m).

Example 13

3-(4-Isopropylphenyl)-2,2,4,6,7-pentamethyl-5-(2-quinolylmethoxy)-2,3-dihydrobenzofuran hydrochloride Sodium hydride (60% liquid paraffin dispersion, 136 mg, 3.39 mmol) was added to a solution of 3-(4-isopropylphenyl)-2,2,4,6,7-pentamethyl-2,3-dihydrobenzofuran-5-ol (1.0 g, 3.08 mmol) in N,N-dimethylformamide (30 mL) at 0° C., and the mixture was stirred for 10 minutes at the same temperature. To the reaction mixture was added 2-(chloromethyl)quinoline hydrochloride (730 mg. 3.39 mmol) and the mixture was stirred for 30 minutes at 80° C. The reaction mixture was poured into water (40 mL), and extracted twice with ethyl acetate. The organic layers were combined, washed with eater, dried over magnesium sulfate, filtered, and concentrated under reduced pressure. To the residue was added 4 N HCl-ethanol, and the solvent was removed through distillation. The residue was crystallized from ethanol-hexane to obtain the title compound (1.1 g, yield 71%).

m.p.: 136–139° C.

¹H-NMR (DMSO-d₆) δ: 0.94 (3H, s), 1.18 (6H, d, J=7.0 Hz), 1.45 (3H, s), 1.78 (3H, s), 2.11 (3H, s), 2.22 (3H, s), 2.85 (1H, septet, J=7.0 Hz), 4.19 (1H, s), 4.20–4.90 (1H, br), 5.10 (1H, d, J=15.8 Hz), 5.19 (1H, d, J=15.8 Hz), 6.65–7.05 (2H, br), 7.13 (2H, d, J=8.8 Hz), 7.72–7.85 (1H, m), 7.91–8.02 (2H, m), 8.15–8.30 (2H, m), 8.80 (1H, d, J=8.8 Hz).

Example 14

5-(3,3-Diphenylpropyloxy)-3-(4-isopropylphenyl)-2,2,4,6,7-pentamethyl-2,3-dihydrobenzofuran Using 3-(4-isopropylphenyl)-2,2,4,6,7-pentamethyl-2,3-dihydrobenzofuran-5-ol and 3,3-diphenylpropyl methanesulfonate, the title compound was obtained in the same manner as in Example 1. This was oily.

Yield: 55%.

¹H-NMR (CDCl₃) δ: 0.99 (3H, s), 1.21 (6H, d, J=7.0 Hz), 1.45 (3H, s), 1.71 (3H, s), 2.08 (3H, s), 2.10 (3H, s), 2.48 (1H, d. J=6.6 Hz), 2.55 (1H, d, J=6.6 Hz), 2.76–2.93 (1H, m), 3.60 (2H, t, J=6.6 Hz), 4.07 (1H, s), 4.25 (1H, t, J=8.0 Hz), 6.60–7.00 (2H, br), 7.06 (2H, d, J=7.6 Hz), 7.10–7.34 (10H, m).

Example 15

Methyl 4-[[3-(4-isopropylphenyl)-2,2,4,6,7-pentamethyl-2,3-dihydrobenzofuran-5-yl]oxymethyl]benzoate Using methyl 3-(4-isopropylphenyl)-2,2,4,6,7-pentamethyl-2,3-dihydrobenzofuran-5-ol and methyl 4-(bromomethyl)methylbenzoate, the title compound was obtained in the same manner as in Example 1.

Yield: 82%.

m.p.: 108–110° C. (from methanol).

¹H-NMR (CDCl₃) δ: 1.01 (3H, s), 1.22 (6H, d, J=7.0 Hz), 1.50 (3H, s), 1.82 (3H, s), 2.16 (3H, s), 2.22 (3H, s), 2.86 (1H, septet, J=7.0 Hz), 3.92 (3H, s), 4.09 (1H, s), 4.76 (2H, s), 6.65–7.00 (2H, br), 7.08 (2H, d, J=8.0 Hz), 7.51 (2H, d, J=8.0 Hz), 8.04 (2H, d, J=8.2 Hz).

07 (1H, s), 4.21–4.37 (4H, m), 6.63–6.98 (2H, br), 7.07 (2H, d, J=8.0 Hz).

Example 16

Methyl α-[[3-(4-isopropylphenyl)-2,2,4,6,7-pentamethyl-2,3-dihydrobenzofuran-5-yl]oxy]phenylacetate Using 3-(4-isopropylphenyl)-2,2,4,6,7-pentamethyl-2,3-dihydrobenzofuran-5-ol and methyl α-bromophenylacetate, the title compound was obtained in the same manner as in Example 1. This was oily.

Yield: 82%.

¹H-NMR (CDCl₃) δ: 0.99 (3H, s), 1.21, 1.23 (6H, each d, J=7.0 Hz), 1.47 (3H, s), 1.57, 1.60 (3H, each s), 2.00, 2.04 (3H, each s), 2.09, 2.11 (3H, each s), 2.75–2.98 (1H, m), 3.70, 3.74 (3H, each s), 4.01 (1H, s), 5.07 (1H, s), 6.60–6.95 (2H, br), 7.06 (2H, d, J=8.0 Hz), 7.24–7.50 (5H, m).

Example 17

3-(4-Isopropylphenyl)-2,2,4,6,7-pentamethyl-5-(2-pyridylmethyloxy)-2,3-dihydrobenzofuran Using 3-(4-isopropylphenyl)-2,2,4,6,7-pentamethyl-2,3-dihydrobenzofuran-5-ol and 2-chloromethylpyridine hydrochloride, the title compound was obtained in the same manner as in Example 1.

Yield: 17%.

m.p.: 88–89° C. (from methanol).

¹H-NMR (CDCl₃) δ: 1.02 (3H, s), 1.22 (6H, d, J=7.0 Hz), 1.51 (3H, s), 1.83 (3H, s), 2.17 (3H, s), 2.24 (3H, s), 2.86 (1H, septet, J=7.0 Hz), 4.10 (1H, s), 4.80 (1H, d, J=15.8 Hz), 4.89 (1H, d, J=15.8 Hz), 6.72–7.02 (2H, br), 7.09 (2H, d, J=8.2 Hz), 7.15–7.25 (1H, m), 7.67–7.81 (2H, m), 8.50–8.58 (1H, m).

Example 18

3-(4-Isopropylphenyl)-2,2,4,6,7-pentamethyl-5-(3-pyridylmethyloxy)-2,3-dihydrobenzofuran Using 3-(4-isopropylphenyl)-2,2,4,6,7-pentamethyl-2,3-dihydrobenzofuran-5-ol and 3-chloromethylpyridine hydrochloride, the title compound was obtained in the same manner as in Example 1. This was oily.

Yield; 76%.

¹H-NMR (CDCl₃) δ: 1.02 (3H, s), 1.22 (6H, d, J=7.0 Hz), 1.50 (3H, s), 1.82 (3H, s), 2.16 (3H, s), 2.22 (3H, s), 2.86 (1H, septet, J=7.0 Hz), 4.09 (1H, s), 4.73 (2H, s), 6.63–7.02 (2H, br), 7.09 (2H, d, J=8.2 Hz), 7.24 (1H, dd, J=7.8, 5.0 Hz), 7.78 (1H, d, J=7.6 Hz), 8.56 (1H, d, J=4.0 Hz), 8.60–8.71 (1H, br).

Example 19

3-(4-Isopropylphenyl)-2,2,4,6,7-pentamethyl-5-(4-pyridylmethyloxy)-2,3-dihydrobenzofuran Using 3-(4-isopropylphenyl)-2,2,4,6,7-pentamethyl-2,3-dihydrobenzofuran-5-ol and 4-chloromethylpyridine hydrochloride, the title compound was obtained in the same manner as in Example 1. This was oily.

Yield: 52%.

¹H-NMR (CDCl₃) δ: 1.02 (3H, s), 1.22 (6H, d, J=7.0 Hz), 1.50 (3H, s), 1.82 (3H, s), 2.16 (3H, s), 2.21 (3H, s), 2.78–2.93 (1H, m), 4.08 (1H, s), 4.73 (2H, s), 6.62–7.01 (2H, br), 7.09 (2H, d, J=8.4 Hz), 7.38 (2H, d, J=5.8 Hz), 8.60 (2H, d, J=5.8 Hz).

Example 20

3-(4-Isopropylphenyl)-5-(2,4-dinitrophenyloxy)-2,2,4,6,7-pentamethyl-2,3-dihydrobenzofuran Sodium hydride (60% liquid paraffin dispersion, 270 mg, 6.75 mmol) was added to a solution of 3-(4-isopropylphenyl)-2,2,4,6,7-pentamethyl-2,3-dihydrobenzofuran-5-ol (2.0 g, 6.16 mmol) in N,N-dimethylformamide (30 mL) at 0° C., and the mixture was stirred for 20 minutes at the same temperature. To the reaction mixture was added 1-chloro-2,4-dinitrobenzene (1.37 g, 6.78 mmol) and the mixture was stirred for 20 minutes at room temperature. The reaction mixture was poured into water (50 mL), and extracted twice with ethyl acetate. The organic layers were combined, dried over magnesium sulfate, filtered, and concentrated under reduced pressure. The residue was crystallized from ethyl acetate-hexane to obtain the title compound (1.5 g, yield 50%).

m.p.: 137–139° C.

¹H-NMR (CDCl₃) δ: 1.04 (3H, s), 1.22 (6H, d, J=7.0 Hz), 1.57 (3H, s), 1.66 (3H, s). 2.03 (3H, s), 2.19 (3H, s), 2.86 (1H, septet. J=7.0 Hz), 4.13 (1H, s), 6.62–6.95 (3H, m), 7.11 (2H, d, J=8.0 Hz), 8.26 (1H, dd, J=9.2, 2.6 Hz), 8.75–8.86 (1H, m).

Example 21

5-(2,4-Bisacetylaminophenyloxy)-3-(4-isopropylphenyl)-2,2,4,6,7-pentamethyl-2,3-dihydrobenzofuran 3-(4-Isopropylphenyl)-5-(2,4-dinitrophenyloxy)-2,2,4,6,7-pentamethyl-2,3-dihydrobenzofuran (800 mg, 1.63 mmol) and 10% palladium-carbon (hydrate) (80 mg) were dispersed in ethanol (40 mL), and the mixture was stirred in a hydrogen atmosphere at 60° C. for 4 hours. The reaction mixture, from which was removed the catalyst through filtration, was concentrated under reduced pressure to obtain 5-(2,4-diaminophenoxy)-3-(4-isopropylphenyl)-2,2,4,6,7-pentamethyl-2,3-dihydrobenzofuran (710 mg). Acetyl chloride (0.26 mL, 3.63 mmol) was added to a solution of the thus-obtained compound (710 mg, 1.65 mmol) and triethylamine (290 mg, 1.70 mmol) in chloroform (30 mL) at 0° C., and the mixture was stirred for 1 hour at the same temperature. The reaction mixture was poured into water (30 mL), and extracted twice with ethyl acetate. The organic layers were combined, washed with an aqueous saturated sodium hydrogencarbonate, dried over magnesium sulfate, filtered, and concentrated under reduced pressure. The residue was subjected to silica gel column chromatography (hexane/ethyl acetate=1/5) to obtain the title compound (640 mg, yield 76%). This was amorphous.

$^1$H-NMR (CDCl$_3$) δ: 1.04 (3H, s), 1.22 (6H, d, J=6.8 Hz), 1.52 (3H, s), 1.64 (3H, s), 2.00 (3H, s), 2.12 (3H, s), 2.18 (3H, s), 2.23 (3H, s), 2.86 (1H, septet, J=6.8 Hz), 4.11 (1H, s), 6.30 (1H, d, J=9.2 Hz), 6.60–7.03 (2H, br), 7.05 (2H, d, J=8.4 Hz), 7.54 (1H, dd, J=9.2, 2.6 Hz), 7.69 (1H, br s), 8.02 (1H, s), 8.21 (1H, d, J=2.6 Hz).

Example 22

α-[3-(4-isopropylphenyl)-2,2,4,6,7-pentamethyl-2,3-dihydrobenzofuran-5-yloxy]phenylacetic acid.

An aqueous solution of 2 N sodium hydroxide (2.5 mL) was dropwise added to a solution of methyl α-[3-(4-isopropylphenyl)-2,2,4,6,7-pentamethyl-2,3-dihydrobenzofuran-5-yloxy]phenylacetate (1.20 g, 2.54 mmol) in a mixture of tetrahydrofuran (24 mL) and methanol (6 mL), and the mixture was stirred for 30 minutes at room temperature. The reaction mixture was concentrated under reduced pressure, to which was added 2 N hydrochloric acid. Then, this was extracted twice with ethyl acetate. The organic layers were washed with water, dried over magnesium sulfate, filtered, and concentrated under reduced pressure. The resulting residue was recrystallized from hexane to obtain the title compound (0.31 g, yield 27%), which was a mixture of diastereomers (ratio: 8/1).

m.p.: 163–166° C.

$^1$H-NMR (CDCl$_3$) δ: 0.98 (3H, s), 1.12–1.25 (6H, m), 1.41–1.56 (6H, m), 1.92–2.10 (6H, m), 2.87 (1H, septet, J=6.6 Hz), 3.99 (1H, s), 5.08–5.10 (1H, m), 5.20–6.00 (1H, br), 6.60–7.17 (4H, m), 7.20–7.39 (5H, m).

Example 23

α-[3-(4-isopropylphenyl)-2,2,4,6,7-pentamethyl-2,3-dihydrobenzofuran-5-yloxy]phenylacetic acid The filtrate in Example 22 was concentrated under reduced pressure to obtain the title compound. (0.50 g, yield 43%), which was amorphous and was a mixture of diastereomers (ratio: 1/3).

$^1$H-NMR (CDCl$_3$) δ: 0.98 (3H, s), 1.16–1.26 (6H, m), 1.39–1.56 (6H, m), 1.91–2.10 (6H, m), 2.84 (1H, septet, J=6.8 Hz), 4.00 (1H, m), 5.07–5.10 (1H, s), 5.40–6.30 (1H, br), 6.50–7.14 (4H, m), 7.20–7.40 (5H, m).

Example 24

3-(4-Isopropylphenyl)-2,2,4,6,7-pentamethyl-5-(3-phenyl-1-propyl)oxy-2,3-dihydrobenzofuran 3-(4-Isopropylphenyl)-2,2,4,6,7-pentamethyl-5-(3-phenyl-2-propen-1-yl)oxy-2,3-dihydrobenzofuran (800 mg, 1.82 mmol) and 10% palladium-carbon (hydrate) (80 mg) were suspended in ethanol (20 mL), and the mixture was stirred for 3 hours in a hydrogen atmosphere at room temperature. The catalyst was removed through filtration, and the filtrate was concentrated under reduced pressure. The residue was crystallized from methanol to obtain the title compound (610 mg, yield 76%).

m.p.: 78–80° C.

$^1$H-NMR (CDCl$_3$) δ: 0.99 (3H, s), 1.22 (6H, d, J=6.8 Hz), 1.48 (3H, s), 1.81 (3H, s), 2.02–2.22 (8H, m), 2.76–2.91 (3H, m), 3.68 (2H, t, J=6.4 Hz), 4.07 (1H, s), 6.70–6.92 (2H, br), 7.07 (2H, d, J=8.8 Hz), 7.15–7.32 (5H, m).

Example 25

3-(4-Isopropylphenyl)-2,2,4,6,7-pentamethyl-5-(2-phenylethyl)oxy-2,3-dihydrobenzofuran A solution of 3-(4-isopropylphenyl)-2,2,4,6,7-pentamethyl-2,3-dihydrobenzofuran-5-ol (1.0 g, 3.08 mmol), 2-phenylethanol (414 mg, 3.39 mmol), triphenylphosphine (890 mg, 3.39 mmol) and diethyl azodicarboxylate (590 mg, 3.39 mmol) in tetrahydrofuran (20 mL) was stirred for 30 minutes at room temperature. The reaction mixture was concentrated under reduced pressure, and the residue was subjected to silica gel column chromatography (hexane/ethyl acetate=100/1) to obtain the title compound (150 mg, yield 11%).

m.p.: 72–74° C. (from methanol).

$^1$H-NMR (CDCl$_3$) δ: 0.98 (3H, s), 1.21 (6H, d, J=7.0 Hz), 1.46 (3H, s), 1.72 (3H, s), 2.10 (3H, s), 2.12 (3H, s), 2.83 (1H, septet, J=7.0 Hz), 3.05 (2H, t, J=7.0 Hz), 3.85 (2H, t, J=7.0 Hz), 4.03 (1H, s), 6.65–7.00 (2H, br), 7.06 (2H, d, J=8.0 Hz), 7.15–7.50 (5H, m).

Example 26

3-(4-Isopropylphenyl)-2,4,6,7-tetramethylbenzofuran-5-yl 4-methoxybenzoate

Triethylamine (0.45 mL, 3.21 mmol) was added to a solution of 3-(4-isopropylphenyl)-2,4,6,7-tetramethylbenzofuran-5-ol (0.90 g, 2.92 mmol) and 4-methoxybenzoyl chloride (0.55 g, 3,21 mmol) in chloroform (15 mL) at room temperature, and the mixture was stirred for 3 hours at 60° C. Water (30 mL) was poured into the reaction mixture, which was then extracted twice with ethyl acetate. The organic layers were combined, washed with 1 N hydrochloric acid and saturated sodium hydroxide, dried over magnesium sulfate, filtered, and concentrated under reduced pressure. The residue was crystallized from ethanol to obtain the title compound (0.52 g, yield 79).

m.p.: 113–115° C.

$^1$H-NMR (CDCl$_3$) δ: 1.28 (6H, d, J=6.8 Hz), 1.90 (3H, s), 2.18 (3H, s), 2.33 (3H, s), 2.46 (3H, s), 2.95 (1H, septet, J=6.8 Hz), 3.89 (3H, s), 6.99 (2H, d, J=9.0 Hz), 7.25 (4H, s), 8.20 (2H, d, J=8.8 Hz).

Example 27

3-(4-isopropylphenyl)-5-(4-methoxybenzyloxy)-2,4,6,7-tetramethylbenzofuran

Using 3-(4-isopropylphenyl)-2,4,6,7-tetramethylbenzofuran-5-ol and 4-methoxybenzyl chloride, the title compound was obtained in the same manner as in Example 1. This was oily.

Yield: 64%.

$^1$H-NMR (CDCl$_3$) δ: 1.31 (6H, d, J=6.8 Hz), 2.06 (3H, s), 2.31 (3H, S), 2.34 (3H, s), 2.43 (3H, s), 2.97 (1H, septet, J=6.8 Hz), 3.82 (3H, s), 4.66 (2H, s), 6.91 (2H, d, J=8.8 Hz), 7.26 (4H, s), 7.40 (2H, d, J=8.8 Hz).

Example 28

2,4,6,7-Tetramethyl-3-phenylbenzofuran-5-yl 4-methoxybenzoate

Using 2,4,6,7-tetramethyl-3-phenylbenzofuran-5-ol and 4-methoxybenzoyl chloride, the title compound was obtained in the same manner as in Example 26.

Yield 64%.

m.p.: 152–154° C. (from methanol).

$^1$H-NMR (CDCl$_3$) δ: 1.88 (3H, s), 2.18 (3H, s), 2.32 (3H, s), 2.46 (3H, s), 3.89 (3H, s), 6.99 (2H, d, J=9.2 Hz), 7.29–7.43 (5H, m), 8.20 (2H, d, J=9.2 Hz).

Examples 29

3-(4-Isopropylphenyl)-6-(4-methoxybenzyloxy)-2,2-dimethyl-2,3-dihydrobenzofuran

Sodium hydride (60% liquid paraffin dispersion, 179.0 mg, 4.48 mmol) was added to a solution of 3-(4-isopropylphenyl)-2,2-dimethyl-2,3-dihydrobenzofuran-6-ol (1.12 g, 4.00 mmol) in N,N-dimethylformamide (15 mL) at 0° C., and the mixture was stirred for 30 minutes at the same temperature. To the reaction mixture was added 4-methoxybenzyl chloride (636.8 mg, 4.07 mmol) and the mixture was stirred for further 30 minutes at room temperature. The reaction mixture was poured into water, and extracted twice with ethyl acetate. The organic layers were combined, washed with an aqueous saturated sodium hydrogencarbonate, dried over magnesium sulfate, filtered, and concentrated under reduced pressure. The residue was subjected to silica gel column chromatography (hexane/ethyl acetate=5/1) to obtain the title compound (1.19 g, yield 74%).

m.p.: 86–88° C. (from hexane).

$^1$H-NMR(CDCl$_3$) δ: 0.95 (3H, s), 1.24 (6H, d, J=7.0 Hz), 1.58 (3H, s), 2.89 (1H, septet, J=7.0 Hz), 3.82 (3H, s), 4.27 (1H, s), 4.96 (2H, s), 6.47–6.52 (2H, m), 6.90–6.95 (3H, m), 7.02 (2H, d, J 8.1 Hz), 7.16 (2H, d, J=8.1 Hz), 7.37 (2H, d, J=8.8 Hz).

Example 30

1'-Benzyl-3-(4-isopropylphenyl)-5-(4-methoxybenzyloxy)-4,6,7-trimethylspiro[benzofuran-2(3H),4'-piperidine]

Sodium hydride (60% liquid paraffin dispersion, 81.4 mg, 1.81 mmol) was added to a solution of 1'-benzyl-3-(4-isopropylphenyl)-4,6,7-trimethylspiro[benzofuran-2(3H),4'-piperidine]-5-ol (824.0 mg. 1.81 mmol) in N,N-dimethylformamide (15 mL) at 0° C., and the mixture was stirred for 30 minutes at the same temperature. To the reaction mixture was added 4-methoxybenzyl chloride (319.9 mg, 2.04 mmol) and the mixture was stirred for further 30 minutes at room temperature. The reaction mixture was poured into water, and extracted twice with ethyl acetate. The organic layers were combined, washed with an aqueous saturated sodium hydrogencarbonate, dried over magnesium sulfate, filtered, and concentrated under reduced pressure. The residue was subjected to silica gel column chromatography (hexane/ethyl acetate=3/1) to obtain the title compound (539 mg, yield 52%). This was amorphous.

$^1$H-NMR(CDCl$_3$) δ: 1.20 (6H, d, J=6.8 Hz), 1.27–1.39 (2H, m), 1.81 (3H, s), 1.86–1.96 (2H, m), 2.19 (3H, s), 2.23 (3H, s), 2.35–2.87 (5H, m), 3.52 (2H, s), 3.80 (3H, s), 4.04 (1H, s). 4.62 (2H, s), 6.6–6.9 (4H, m), 7.04–7.08 (2H, m), 7.22–7.36 (7H, m).

Example 31

1'-Benzyl-5-(4-methoxybenzyloxy)-4,6,7-trimethylspiro[benzofuran-2(3H),4'-piperidine]

Sodium hydride (60% liquid paraffin dispersion, 134.6 mg, 3.37 mmol) was added to a solution of 1'-benzyl-4,6,7-trimethylspiro[benzofuran-2(3H),4'-piperidine]-5-ol (1.01 g. 2.98 mmol) in N,N-dimethylformamide (15 mL) at 0° C., and the mixture was stirred for 30 minutes at the same temperature. To the reaction mixture was added 4-methoxybenzyl chloride (584.9 mg, 3.43 mmol) and the mixture was stirred for further 30 minutes at room temperature. The reaction mixture was poured into water, and extracted twice with ethyl acetate. The organic layers were combined, washed with an aqueous saturated sodium hydrogencarbonate, dried over magnesium sulfate, filtered, and concentrated under reduced pressure. The residue was subjected to silica gel column chromatography (hexane/ethyl acetate=2/1) to obtain the title compound (1.15 g, yield 85%).

m.p.: 85–86° C. (from hexane).

$^1$H-NMR(CDCl$_3$) δ: 1.80–2.00 (4H, m), 2.10 (3H, s), 2.15 (3H, s), 2.18 (3H, s), 2.60 (4H, br), 2.87 (2H, s), 3.58 (2H, s), 3.83 (3H, s), 4.62 (2H, s), 6.90–6.95 (2H, m), 7.30–7.43 (7H, m).

Example 32

3-(4-Isopropylphenyl)-5-(4-methoxybenzyloxy)-1',4,6,7-tetramethylspiro[benzofuran-2(3H),4'-piperidine]

Sodium hydride (60% liquid paraffin dispersion, 64.3 mmol, 1.61 mmol) was added to a solution of 3-(4-isopropylphenyl)-1',4,6,7-tetramethylspiro[benzofuran-2(3H),4'-piperidine]-5-ol (509.0 mg, 1.34 mmol) in N,N-dimethylformamide (25 mL) at 0° C., and the mixture was stirred for 30 minutes at the same temperature. To the reaction mixture was added 4-methoxybenzyl chloride (244.0 mg, 1.56 mmol) and the mixture was stirred for further 30 minutes at room temperature. The reaction mixture was poured into water, and extracted twice with ethyl acetate. The organic layers were combined, washed with an aqueous saturated sodium hydrogencarbonate, dried over magnesium sulfate, filtered, and concentrated under reduced pressure. The residue was subjected to silica gel column chromatography (Chromatorex NH DM1020, Fuji Silysia Chemical LTD) (hexane/ethyl acetate=1/1) to obtain the title compound (262 mg, yield 39%). This was amorphous.

$^1$H-NMR(CDCl$_3$) δ: 1.21 (6H, d, J=7.0 Hz), 1.3–1.4 (2H, m), 1.82 (3H, s), 1.99–2.04 (2H, m), 2.19 (3H, s), 2.23 (3H, s), 2.30 (3H, s), 2.37–2.70 (4H, m), 2.82 (1H, septet, J=7.0 Hz), 3.81 (3H, s), 4.05 (1H, s), 4.62 (2H, s), 6.6–6.9 (4H, m), 7.05–7.09 (2H, m), 7.33–7.37 (2H, m).

Example 33

3-(4-Isopropylphenyl)-1',4,6,7-tetramethyl-5-(4-pyridylmethyloxy)spiro[benzofuran-2(3H),4'-piperidine]

Sodium hydride (60% liquid paraffin dispersion, 187.3 mg, 4.98 mmol) was added to a solution of 3-(4- isopropylphenyl)-1',4,6,7-tetramethylspiro[benzofuran-2 (3H),4'-piperidine]-5-ol (817.7 mg, 2.15 mmol) in N,N-dimethylformamide (30 mL) at 0° C., and the mixture was stirred for 30 minutes at the same temperature. To the reaction mixture was added 4-chloromethylpyridine hydrochloride (364.5 mg, 2.22 mmol) and the mixture was stirred for further 30 minutes at room temperature. The reaction mixture was poured into water, and extracted twice with ethyl acetate. The organic layers were combined, washed with an aqueous saturated sodium hydrogencarbonate, dried over magnesium sulfate, filtered, and concentrated under reduced pressure. The residue was subjected to silica gel column chromatography (Chromatorex NH DM1020, Fuji Silysia Chemical LTD) (hexane/ethyl acetate=4/1) to obtain the title compound (575 mg, yield 57%).

m.p.: 96–98° C. (from hexane).

$^1$H-NMR(CDCl$_3$) δ: 1.21 (6H, d, J=7.0 Hz),1.34–1.41 (2H, m), 1.82 (3H, s), 1.92–2.11 (2H, m), 2.19 (3H, s), 2.21 (3H, s), 2.30 (3H, s), 2.37–2.65 (4H, m), 2.85 (1H, septet, J=7.0 Hz), 4.05 (1H, s), 4.72 (2H, s), 6.6–7.1 (4H, m), 7.36–7.39 (2H, m), 8.58–8.61 (2H, m).

The chemical structural formulae of the compounds obtained in these Examples are shown below.

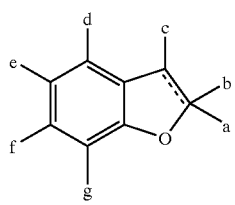

| Ex. No. | a | b | c | d | e | f | g | ----- |
|---|---|---|---|---|---|---|---|---|
| 1 | Me | Me | Me-CH(Me)-C$_6$H$_4$- | Me | C$_6$H$_5$-CH$_2$O- | Me | Me | — |
| 2 | Me | Me | Me$_2$N-C$_6$H$_4$- | Me | C$_6$H$_5$-CH$_2$O- | Me | Me | — |
| 3 | Me | Ph-piperidine-N-CH$_2$- | H | Me | C$_6$H$_5$-CH$_2$O- | Me | Me | — |
| 4 | Me | Me | Me-CH(Me)-C$_6$H$_4$- | Me | MeO-C$_6$H$_4$-CH$_2$O- | Me | Me | — |
| 5 | Me | Me | Me-CH(Me)-C$_6$H$_4$- | H | MeO-C$_6$H$_4$-CH$_2$O- | H | H | — |
| 6 | Me | Me | Me$_2$N-C$_6$H$_4$- | Me | MeO-C$_6$H$_4$-CH$_2$O- | Me | Me | — |
| 7 | Me | Me | morpholino-C$_6$H$_4$- | Me | MeO-C$_6$H$_4$-CH$_2$O- | Me | Me | — |
| 8 | Me | Me | Me-N-piperazine-C$_6$H$_4$- | Me | MeO-C$_6$H$_4$-CH$_2$O- | Me | Me | — |
| 9 | Me | Me | Me-CH(Me)-C$_6$H$_4$- | Me | MeS-C$_6$H$_4$-CH$_2$O- | Me | Me | — |

-continued
| 10 | Me | Me | 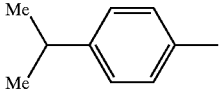 | Me | 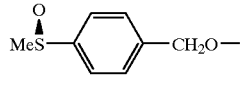 | Me | Me | — |
| 11 | Me | Me | 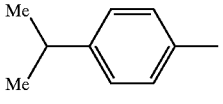 | Me | 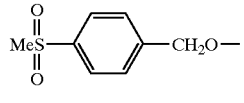 | Me | Me | — |
| 12 | Me | Me | 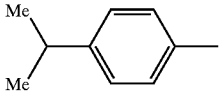 | Me | 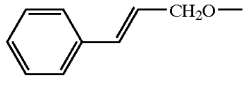 | Me | Me | — |
| 13 | Me | Me | 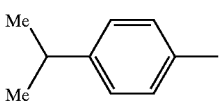 | Me | 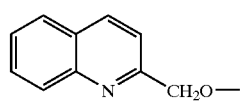 | Me | Me | — |
| 14 | Me | Me | 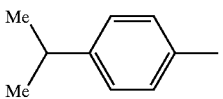 | Me | 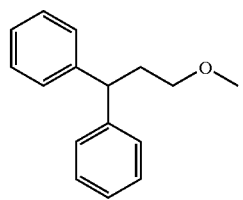 | Me | Me | — |
| 15 | Me | Me | 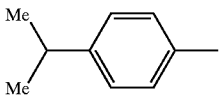 | Me | 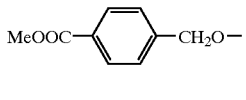 | Me | Me | — |
| 16 | Me | Me | 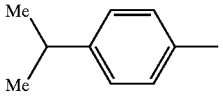 | Me | 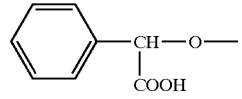 | Me | Me | — |
| 17 | Me | Me | 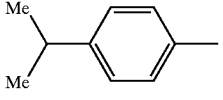 | Me | 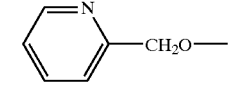 | Me | Me | — |
| 18 | Me | Me | 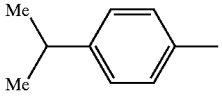 | Me | 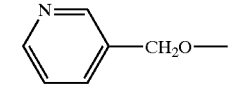 | Me | Me | — |
| 19 | Me | Me | 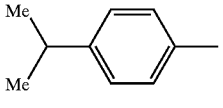 | Me | 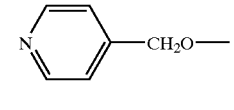 | Me | Me | — |
| 20 | Me | Me | 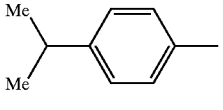 | Me | 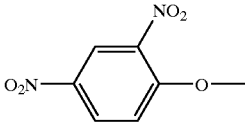 | Me | Me | — |
| 21 | Me | Me | 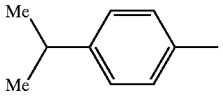 | Me | 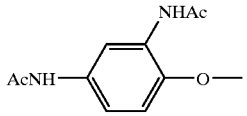 | Me | Me | — |
| 22 | Me | Me | 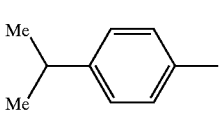 | Me | 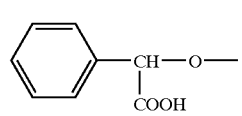 | Me | Me | — |

-continued
| | | | | | | | | |
|---|---|---|---|---|---|---|---|---|
| 23 | Me | Me | 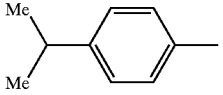 | Me | 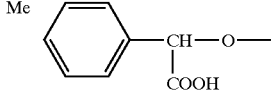 | Me | Me | — |
| 24 | Me | Me | 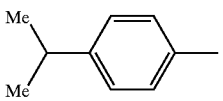 | Me | 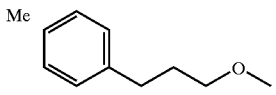 | Me | Me | — |
| 25 | Me | Me | 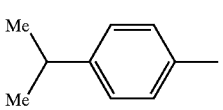 | Me | 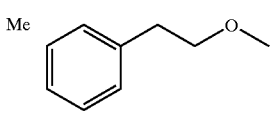 | Me | Me | — |
| 26 | Me | — | 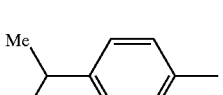 | Me | 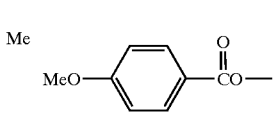 | Me | Me | = |
| 27 | Me | — | 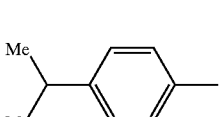 | Me | 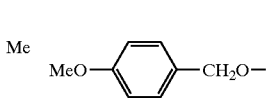 | Me | Me | = |
| 28 | Me | — | 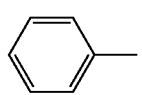 | Me | 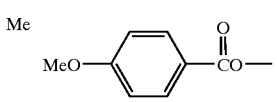 | Me | Me | = |
| 29 | Me | Me | 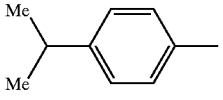 | H | H | 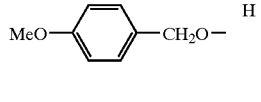 | H | — |
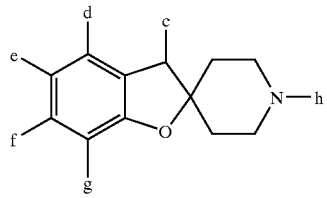
| Ex. No. | c | d | e | f | g | h |
|---|---|---|---|---|---|---|
| 30 | 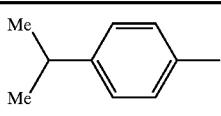 | Me | 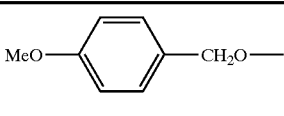 | Me | Me | 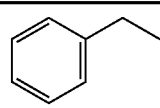 |
| 31 | H | Me | 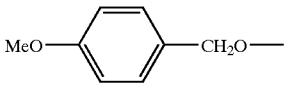 | Me | Me | 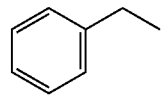 |
| 32 | 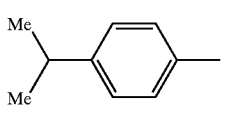 | Me | 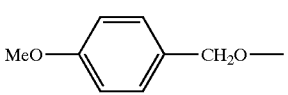 | Me | Me | Me |
| 33 | 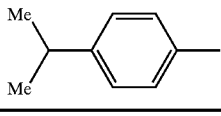 | Me | 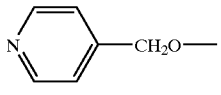 | Me | Me | Me |

Formulation of Example 1

| | | |
|---|---|---|
| (1) | Compound obtained in Example 4 | 50 mg |
| (2) | Lactose | 34 mg |
| (3) | Corn starch | 10.6 mg |
| (4) | Corn starch (paste) | 5 mg |
| (5) | Magnesium stearate | 0.4 mg |
| (6) | Calcium carboxymethyl cellulose | 20 mg |
| | Total | 120 mg |

(1) to (6) were mixed in an ordinary manner, and tabletted into tables using a tabletting machine.

Experimental Example 1

Evaluation of cell protective activity against β-amyloid neurotoxicity in human neuroblastoma SK—N—SH cells.

Method a) Material Used

Human neuroblastoma SK—N—SH cells: obtained from American Type Tissue Culture Collection (ATCC).

DMEM/F-12 medium: obtained from Nikken Biological Medicine Laboratory Co.

$Ca^{++}$ and $Mg^{++}$ free phosphate-buffered saline (PBS(–)): obtained Nikken Biological Medicine Laboratory Co.

N2 supplement™, and EDTA solution: obtained from Gibco BRL Co.

Fetal calf serum, and mixture of penicillin (5000 U/mL) and streptomycin (5 mg/mL): obtained from Bio Whittaker Co.

Recombinant human interferon gamma (rhIFN-γ): obtained from Wako Pure Chemical Co.

Alamar Blue™ reagent: obtained from AccuMed International, Inc.

Culture flasks: manufactured by Falcon Co. Collagen-coated, 96-well multi-plate: manufactured by Iwaki Glass Co.

β-amyloid 25–35: obtained from Bachem AG.

Other reagents: commercially-available special-grade chemicals.

b) Test Method (1) Cultivation of SK—N—SH cells

SK—N—SH cells were sub-cultured in DMEM/F12 medium containing 5% FCS, 0.5% N2 supplement™, 1% of mixture of penicillin (5000 U/mL) and streptomycin (5 mg/mL), under 10 t $CO_2$ and 90% air, using $CO_2$ incubator. At sub-confluent condition, cells were harvested from culture flask with PBS(–) containing 2.5 mM EDTA, and plated at a density of $1.0 \times 10^4$ cells/100 µl of culture medium/well in collagen-coated 96-well multi-plate. The next day, 80 µl of culture medium was substituted with DMEM/F12 medium (containing neither FCS nor N2 supplement) containing 1.25 ng/mL of rhIFN-γ, and after 24 hr cultivation cells were used for cell toxicity assay mentioned below.

(2) Measurement of cell protective activity of test compounds against β-amyloid 25–35-induced neurotoxicity After pretreatment of SK—N—SH cells with rhIFN-γ in collagen-coated 96 well multi-plate, cell toxicity assay was started by addition of β-amyloid 25–35 and test compound. Briefly, 80 µl of culture medium was removed, and 40 µl of β-amyloid 25–35 and 40 µl of test compound were added to cultures at the same time. The final concentrations of β-amyloid 25–35 and test compounds were 10 µM and 1 µM, respectively.

The test compound was dissolved at 10 mM in dimethylsulfoxide (DMSO) and diluted in DMEM/F12 medium.

β-amyloid 25–35 was dissolved at 5 mM in sterile pure water, and stored at –80° C. Immediately before use, the stock solution β-amyloid 25–35 was diluted in DMEM/F12 medium and sonicated.

(3) Evaluation of cell protective activity of test compound

Cell viability was assessed by the reduction of Alamar Blue™ reagents, 3 days after starting of the cell toxicity assay. Briefly, 20 µl of culture medium was substituted with 20 µl of Alamar Blue™ reagents and incubated 4 hours. Absorbances were determined at wavelengths of 570 nm and 600 nm using a plate reader (MTP-32 Micro-plate Reader, manufactured by Corona Co.). Amount of reduced Alamar Blue reagents was determined by subtracting $absorbance_{600}$ from $absorbance_{570}$. The cell protective activity of the test compound was estimated according to the following equation:

Cell protective activity of compound $[(A–B)/(C–B)] \times 100$ (%) 20 where;

A: cell viability of the group treated with both the test compound and β-amyloid B: cell viability of the group treated with β-amyloid only C: cell viability of the control group Results Cell viability of the group treated with both the test compound and β-amyloid was compared with that 30 group treated with β-amyloid only using Dunnett's test.

Cell viability of each group was determined using at least 4 culture well. The data obtained are shown in the following Table.

| Compound of Example | Cell Protecting Activity (%) |
|---|---|
| 1 | 30.7 |
| 2 | 27.9 |
| 3 | 39.4 |
| 7 | 27.3 |
| 12 | 44.8 |
| 14 | 44.2 |
| 25 | 47.0 |

These data verify that compound (I) and compound (Ia) well suppress β-amyloid toxicity.

INDUSTRIAL APPLICABILITY

Compounds (I) and (Ia) have excellent suppressive effects on neurodegeneration and good permeability to the brain, while having low toxicity, and are therefore useful as medicines for preventing and/or treating neurodegenerative diseases.

What is claimed is:

1. A compound of the formula:

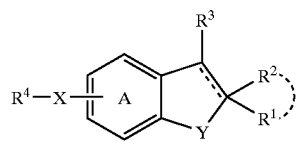

wherein $R^1$ and $R^2$ are each a $C_{1-6}$ alkyl or $R^1$ and $R^2$ form, taken together with the adjacent carbon atom, a piperidine optionally substituted by 1 to 3 substituents selected from the group consisting of $C_{1-6}$ alkyl, $C_{6-14}$ aryl and $C_{7-16}$ aralkyl;

$R^3$ is a phenyl optionally substituted by 1 to 3 substituents selected from the group consisting of halogen atoms, $C_{1-6}$ alkyl, $C_{1-6}$ alkoxy, amino, mono-$C_{1-6}$ alkylamino and di-$C_{1-6}$ alkylamino;

$R^4$ is
 (i) $C_{1-6}$ alkyl substituted by a phenyl or pyridyl, each of which is optionally substituted by 1 to 3 substituents selected from the group consisting of halogen atoms, $C_{1-6}$ alkyl, $C_{1-6}$ alkoxy, hydroxy, amino, mono-$C_{1-6}$ alkylamino, di-$C_{1-6}$ alkylamino and carboxy, or
 (ii) an acyl of the formula: —(C=O)—$R^{5'}$ wherein $R^{5'}$ is a phenyl or phenyl-$C_{1-6}$ alkyl, each of which is optionally substituted by 1 to 3 substituents selected from the group consisting of halogen atoms, $C_{1-6}$ alkyl, $C_{1-6}$ alkoxy, hydroxy, amino, mono-$C_{1-6}$ alkylamino, di-$C_{1-6}$ alkylamino and carboxy;

X is an oxygen atom;
Y is an oxygen atom; and
ring A is a benzene ring which is optionally further substituted by 1 to 3 substituents selected from the group consisting of halogen atoms, halogenated or unhalogenated $C_{1-6}$ alkyl, halogenated or unhalogenated $C_{1-6}$ alkoxy, amino, mono-$C_{1-6}$ alkylamino and di-$C_{1-6}$ alkylamino, provided that when === is a single bond, $R^4$ is not acyl, and salts thereof.

2. A compound of the formula:

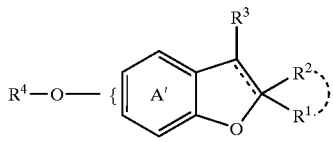

wherein $R^1$ and $R^2$ are each $C_{1-6}$ alkyl or $R^1$ and $R^2$ form, taken together with the adjacent carbon atom, a piperidine substituted by a $C_{1-6}$ alkyl or a $C_{7-16}$ aralkyl;

$R^3$ is a phenyl optionally substituted by 1 to 3 substituents selected from the group consisting of (1) $C_{1-6}$ alkyl, (2) di-$C_{1-6}$ alkylamino and (3) 6-membered saturated cyclic amino optionally substituted by a $C_{1-6}$ alkyl, $R^4$ is
 (i) a phenyl optionally substituted by 1 to 3 substituents selected from the group consisting of nitro and $C_{1-6}$ alkyl-carboxamido,
 (ii) a $C_{1-6}$ alkyl or $C_{2-6}$ alkenyl group substituted by 1 to 3 of phenyl, quinolyl or pyridyl, each of which is optionally substituted by 1 to 3 substituents selected from the group consisting of $C_{1-6}$ alkoxy, $C_{1-6}$ alkylthio, $C_{1-6}$ alkoxy-carbonyl, $C_{1-6}$ alkylsulfonyl and $C_{1-6}$ alkylsulfinyl, which $C_{1-6}$ alkyl or $C_{2-6}$ alkenyl group is optionally further substituted by a phenyl, carboxy or $C_{1-6}$ alkoxy-carbonyl, or
 (iii) an acyl of the formula: —(C=O)—$R^{5''}$
  wherein $R^{5''}$ is phenyl substituted by a $C_{1-6}$ alkoxy; and ring A' is a benzene ring which is optionally further substituted by 1 to 3 $C_{1-6}$ alkyl, provided that when === is a single bond, $R^4$ is not acyl, and salts thereof.

3. 3-(4-isopropylphenyl)-2,4,6,7-tetramethylbenzofuran-5-yl 4-methoxybenzoate, 3-(4 isopropylphenyl)-5-(4-methoxybenzyloxy)-2,4,6,7-tetramethylbenzofuran, 3-(4-isopropylphenyl)-5-(4-methoxybenzyloxy)-1',4,6,7-tetramethylspiro(benzofuran-2(3H), 4'-piperidine), or a salt thereof.

4. A process for producing a compound of claim 1, which comprises reacting a compound of the formula:

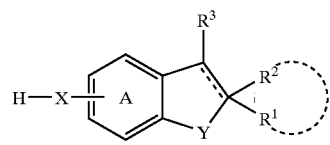

wherein each symbol is as defined in claim 1, or a salt thereof with a compound of the formula: $R^4$-L wherein L represents a leaving group and $R^4$ is as defined in claim 1, or salt thereof.

5. A pharmaceutical composition which comprises a compound of claim 1, and a pharmaceutically acceptable carrier, excipient or diluent.

6. 3-(4-Isopropylphenyl)-5-(4-methoxybenzyloxy)-2,2,4,6,7-pentamethyl-2,3-dihydrobenzofuran.

* * * * *